United States Patent [19]
Cooper et al.

[11] Patent Number: 5,977,062
[45] Date of Patent: *Nov. 2, 1999

[54] GLYCOPEPTIDE ANTIBIOTIC DERIVATIVES

[75] Inventors: Robin D. G. Cooper, Indianapolis; Bret E. Huff, Mooresville; Thalia I. Nicas, Indianapolis; John T. Quatroche, Indianapolis; Michael J. Rodriguez, Indianapolis; Nancy J. Snyder, Charlottesville; Michael A. Staszak, Indianapolis; Richard C. Thompson, Frankfort; Stephen C. Wilkie; Mark J. Zweifel, both of Indianapolis, all of Ind.

[73] Assignee: Eli Lilly and Company, Indianapolis, Ind.

[ * ] Notice: This patent is subject to a terminal disclaimer.

[21] Appl. No.: 09/062,235

[22] Filed: Apr. 17, 1998

Related U.S. Application Data

[63] Continuation of application No. 08/410,155, Mar. 24, 1995, Pat. No. 5,840,684, which is a continuation-in-part of application No. 08/356,413, Dec. 15, 1994, abandoned, which is a continuation-in-part of application No. 08/189,393, Jan. 28, 1994, abandoned.

[51] Int. Cl.$^6$ ................................................. A61K 38/12
[52] U.S. Cl. ........................... 514/8; 514/11; 514/16; 514/17; 530/317; 530/322; 530/329
[58] Field of Search .................... 514/8, 11, 16, 514/17; 530/317, 322, 329

[56] References Cited

U.S. PATENT DOCUMENTS

| | | | |
|---|---|---|---|
| 3,067,099 | 12/1962 | McCormick et al. | 167/65 |
| 3,338,786 | 8/1967 | Kunstmann et al. | 167/65 |
| 4,552,886 | 11/1985 | Krumkalns et al. | 514/342 |
| 4,639,433 | 1/1987 | Hunt et al. | 514/8 |
| 4,643,987 | 2/1987 | Nagarajan et al. | 514/8 |
| 4,698,327 | 10/1987 | Nagarajan et al. | 514/8 |
| 4,725,668 | 2/1988 | Strazzoline et al. | 530/317 |
| 4,882,419 | 11/1989 | Malabarba et al. | 530/317 |
| 4,946,941 | 8/1990 | Kondo et al. | 530/317 |
| 5,071,749 | 12/1991 | Kondo et al. | 530/317 |
| 5,185,320 | 2/1993 | Trani et al. | 514/8 |
| 5,187,082 | 2/1993 | Hamill et al. | 435/71.3 |
| 5,194,424 | 3/1993 | Malabarba et al. | 514/8 |

FOREIGN PATENT DOCUMENTS

| | | |
|---|---|---|
| 0 201 251 | 11/1986 | European Pat. Off. . |
| 0 265 071 | 4/1988 | European Pat. Off. . |
| 0 276 740 | 8/1988 | European Pat. Off. . |
| 0 287 110 | 10/1988 | European Pat. Off. . |
| 0 316 712 | 5/1989 | European Pat. Off. . |
| 0 339 982 | 11/1989 | European Pat. Off. . |
| 0 365 319 | 4/1990 | European Pat. Off. . |
| 0 435 503 | 7/1991 | European Pat. Off. . |
| 0 525 499 | 2/1993 | European Pat. Off. . |

OTHER PUBLICATIONS

U.S. application No. 08/410,155, Cooper et al., filed Mar. 1995.
Chem. Abst. 110:17188 (1989).
Chem. Abst. 53:7317 (1959).
R. Nagarajan, et al., *J. Antibiotics*, vol. XLI, No. 10 (1988), p. 1430.
R. Nagarajan, et al., *J. Antibiotics*, vol. XLII, No. 1 (1989), p. 63.
T. Nicas, et al., *Antimicrob. Agents and Chemoth.*, vol. 33, No. 9 (1989), p. 1477.
R. Nagarajan, *Antimicrob. Agents and Chemoth.*, vol. 35, No. 4 (1991), p. 605.
Chem. Abst. 116:5304 (1992).
R. Nagarajan, *J. Antibiotics*, vol. 46, No. 8 (1993), p. 1181.
A.Y. Pavlov et al.,*J. Antibiotics*, 47(2), pp. 225–232, (1994).
*J. Org. Chem.*, 54, 983–986 (1989).
*J. Antibiotics*, XLI, #10, 1506–1510 (1988).
*J. Antibiotics* 44, #11, 1208–1221 (1991).
*Nature*, 271, 223–225 (Jan. 19, 1978).

*Primary Examiner*—Cecilia J. Tsang
*Assistant Examiner*—Anish Gupta
*Attorney, Agent, or Firm*—Arlene K. Musser

[57] ABSTRACT

The present invention provides glycopeptide antibiotic derivative compounds. These derivative compounds possess antibacterial activity against a wide variety of bacteria, including activity against vancomycin-resistant isolates. Methods of making and using these glycopeptide antibiotic derivative compounds are also provided.

34 Claims, No Drawings

GLYCOPEPTIDE ANTIBIOTIC DERIVATIVES

This application is a continuation of application Ser. No. 08/410,155 filed in Mar. 24, 1995, now U.S. Pat. No. 5,840,684 which is a continuation-in-part of application Ser. No. 08/356,413 filed Dec. 15, 1994, now abandoned, which is a continuation-in-part of application Ser. No. 08/189,393 filed Jan. 28, 1994, now abandoned.

BACKGROUND OF THE INVENTION

New improved antibiotics are continually in demand, particularly for the treatment of human diseases. Increased potency, expanded spectrum of bacterial inhibition, increased in vivo efficacy, and improved pharmaceutical properties are some of the goals for improved antibiotics.

In the search for new antibiotics, structural modification of known antibiotics is attempted whenever possible. The glycopeptide antibiotics have such complex structures that even small changes are difficult. Furthermore, it is difficult to predict the effect these changes will make in the antimicrobial and physiological properties. Processes for modifying known antibiotics and the new active derivatives made by such processes, therefore, continue to be of great importance.

Previously, N-alkyl and N-acyl derivatives of the glycopeptides vancomycin, A51568A, A51568B, M43A and M43D have been prepared (U.S. Pat. Nos. 4,639,433, 4,643,987, and 4,698,327). Several of these compounds exhibited microbiological activity, including activity against vancomycin-resistant isolates. Nicas et al., *Antimicrobial Agents and Chemotherapy,* 33(9):1477–1481 (1989). In addition, European Patent Application Publication No. 0435503, published Jul. 3, 1993, describes certain N-alkyl and N-acyl derivatives of the A82846 glycopeptides, factors A, B, and C.

The formula I compounds of this invention are new members of the glycopeptide group of antibiotics. These new compounds are derivatives of known glycopeptide antibiotics that include vancomycin (U.S. Pat. 3,067,099); A82846A, A82846B, and A82846C (U.S. Pat. 5,312,738, European Patent Publication 256,071 A1); PA-42867 factors A, C, and D (U.S. Pat. 4,946,941 and European Patent Publication 231,111 A2); A83850 (U.S. Pat. No. 5,187,082); avoparcin (U.S. Pat. 338,786 and U.S. Pat. 4,322,343); actinoidin, also known as K288 (*J. Antibiotics* Series A 14:141 (1961); helevecardin (*Chem. Abstracts* 110:17188 (1989) and Japanese Patent Application 86/157,397); galacardin (*Chem. Abstracts* 110:17188 (1989) and Japanese Patent Application 89/221,320); and M47767 (European Patent Publication 339,982). The references listed above which describe these glycopeptides are incorporated herein by reference.

Enterococci are important human pathogens. Infections caused by enterococci are generally difficult to treat. Glycopeptides, such as vancomycin and teicoplanin, have become important therapies in the treatment of infections due to enterococci. However, strains of *Enterococcus faecium* and *E. faecalis* have recently been isolated that are resistant to vancomycin and teicoplanin. Leclercq et al., "Plasmid Mediated Resistance to Vancomycin and Teicoplanin in Enterococcus Faecium," *The New England Journal of Medicine,* 319(3):157–161 (1988), and Uttley et al., "Vancomycin-Resistant Enterococci," *Lancet,* 1:57–58 (1988). The isolates were also found to be resistant to other antibiotics. A recent survey found 7.9% of Enterococci in United States hospitals are now vancomycin resistant. "Nosocomial Enterococci Resistant to Vancomycin" *Morbidity and Mortality Weekly Report* 42 (30):597–598 (1993). In addition to their broad activity against gram-positive organisms, many of the glycopeptide compounds of this invention also exhibit improved antimicrobial activity against vancomycin-resistant isolates.

SUMMARY OF THE INVENTION

The present invention provides compounds of the formula I:

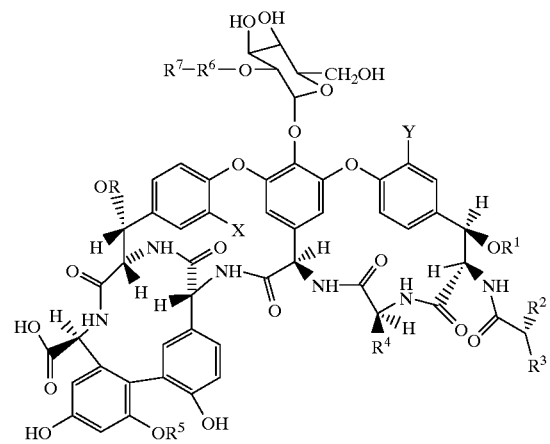

or salt thereof, wherein:

X and Y are each independently hydrogen or chloro;

R is hydrogen, 4-epi-vancosaminyl, actinosaminyl, ristosaminyl, or a group of the formula —$R^a$—$R^{7a}$, wherein $R^a$ is 4-epi-vancosaminyl, actinosaminyl, or ristosaminyl, and $R^{7a}$, defined below, is attached to the amino group of $R^a$;

$R^1$ is hydrogen, or mannose;

$R^2$ is —$NH_2$, —$NHCH_3$, —$N(CH_3)_2$, —$NHR^{7b}$, or —$N(CH_3)R^{7b}$, wherein $R^{7b}$ is defined below;

$R^3$ is —$CH_2CH(CH_3)_2$, [p-OH, m-Cl]phenyl, p-rhamnose-phenyl, [p-rhamnose-galactose]phenyl, [p-galactose-galactose]phenyl, or [p-$CH_3$O-rhamnose]phenyl;

$R^4$ is —$CH_2(CO)NH_2$, benzyl, [p-OH]phenyl, or [p-OH, m-Cl]phenyl;

$R^5$ is hydrogen, or mannose;

$R^6$ is 4-epi-vancosaminyl, L-acosaminyl, L-ristosaminyl, or L-actinosaminyl;

$R^7$, as defined below, is attached to the amino group of $R^6$; and $R^7$, $R^{7a}$, and $R^{7b}$ are each independently selected from the group consisting of hydrogen, ($C_2$–$C_{16}$)alkenyl, ($C_2$–$C_{12}$) alkynyl, ($C_1$–$C_{12}$alkyl)-$R_8$, ($C_1$–$C_{12}$ alkyl)-halo, ($C_2$–$C_6$ alkenyl)-$R_8$, ($C_2$–$C_6$ alkynyl)-$R_8$, and ($C_1$–$C_{12}$ alkyl)-O—$R_8$, provided that $R^7$, $R^{7a}$, and $R^{7b}$ are not all hydrogen, and $R^8$ is selected from the group consisting of:

a) multicyclic arvi unsubstituted or substituted with one or more substituents independently selected from the group consisting of:

(i) hydroxy, (ii) halo, (iii) nitro, (iv) ($C_1$–$C_6$)alkyl, (v) ($C_1$–$C_6$)alkenyl, (vi) ($C_1$–$C_6$)alkynyl, (vii) ($C_1$–$C_6$)alkoxy, (viii) halo-$(C_1-C_6)$alkyl,
(ix) halo-$(C_1-C_6)$alkoxy,
(x) carbo-$(C_1-C_6)$alkoxy,
(xi) carbobenzyloxy,
(xii) carbobenzyloxy substituted with $(C_1-C_6)$alkyl, $(C_1-C_6)$ alkoxy, halo, or nitro,
(xiii) a group of the formula —S(O)$_{n'}$—R$^9$, wherein n' is 0–2 and R$^9$ is $(C_1-C_6)$alkyl, phenyl, or phenyl substituted with $(C_1-C_6)$alkyl, $(C_1-C_6)$alkoxy, halo, or nitro, and
(xiv) a group of the formula —C(O)N(R$^{10}$)$_2$ wherein each R$^{10}$ substituent is independently hydrogen, $(C_{1-C6})$-alkyl, $(C_1-C_6)$-alkoxy, phenyl, or phenyl substituted with $(C_{1-C6})$-alkyl, $(C_1-C_6)$-alkoxy, halo, or nitro;

b) heteroaryl unsubstituted or substituted with one or more substituents independently selected from the group consisting of:
(i) halo,
(ii) $(C_1-C_6)$alkyl,
(iii) $(C_1-C_6)$alkoxy,
(iv) halo-$(C_1-C_6)$alkyl,
(v) halo-$(C_1-C_6)$alkoxy,
(vi) phenyl,
(vii) thiophenyl,
(viii) phenyl substituted with halo, $(C_1-C_6)$ alkyl, $(C_1-C_6)$ alkenyl, $(C_1-C_6)$alkynyl, $(C_1-C_6)$alkoxy, or nitro,
(ix) carbo-$(C_1-C_6)$alkoxy,
(x) carbobenzyloxy,
(xi) carbobenzyloxy substituted with $(C_1-C_6)$alkyl, $(C_1-C_6)$ alkoxy, halo, or nitro,
(xii) a group of the formula —S(O)$_{n'}$—R$^9$, as defined above,
(xiii) a group of the formula —C(O)N(R$^{10}$)$_2$ as defined above, and
(xiv) thienyl;
c) a group of the formula:

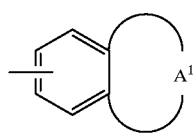

wherein A$^1$ is —OC(A$^2$)$_2$—C(A$^2$)$_2$—O—, —O—C(A$^2$)$_2$—O—, —C(A$^2$)$_2$—O—, or —C(A$^2$)$_2$—C(A$^2$)$_2$—C(A$^2$)$_2$—, and each A$^2$ substituent is independently selected from hydrogen, $(C_1-C_6)$-alkyl, $(C_1-C_6)$ alkoxy, and $(C_4-C_{10})$cycloalkyl;
d) a group of the formula:

wherein p is from 1 to 5; and
R$^{11}$ is independently selected from the group consisting of:
(i) hydrogen,
(ii) nitro,
(iii) hydroxy,
(iv) halo,
(v) $(C_1-C_8)$alkyl,
(vi) $(C_1-C_8)$alkoxy,
(vii) $(C_9-C_{12})$alkyl,
(viii) $(C_2-C_9)$alkynyl,
(ix) $(C_9-C_{12})$alkoxy,
(x) $(C_1-C_3)$alkoxy substituted with $(C_1-C_3)$alkoxy, hydroxy, halo$(C_1-C_3)$alkoxy, or $(C_1-C_4)$alkylthio,
(xi) $(C_2-C_5)$alkenyloxy
(xii) $(C_1-C_{13})$alkynyloxy
(xiii) halo-$(C_1-C_6)$alkyl,
(xiv) halo-$(C_1-C_6)$alkoxy,
(xv) $(C_2-C_6)$alkylthio,
(xvi) $(C_2-C_{10})$alkanoyloxy,
(xvii) carboxy-$(C_2-C_4)$alkenyl,
(xviii) $(C_1-C_3)$alkylsulfonyloxy,
(xix) carboxy-$(C_1-C_3)$alkyl,
(xx) N-[di$(C_1-C_3)$-alkyl]amino-$(C_1-C_3)$alkoxy,
(xxi) cyano-$(C_1-C_6)$alkoxy, and
(xxii) diphenyl-$(C_1-C_6)$alkyl,
with the proviso that when R$^{11}$ is $(C_1-C_8)$alkyl, $(C_1-C_8)$alkoxy, or halo, p must be greater or equal to 2, or when R$^7$ is $(C_1-C_3$ alkyl)–R$^8$ then R$^{11}$ is not hydrogen, $(C_1-C_8)$alkyl, $(C_1-C_8)$alkoxy, or halo;
e) a group of the formula:

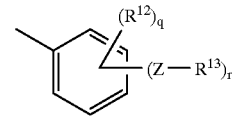

wherein q is 0 to 4;
R$^{12}$ is independently selected from the group consisting of:
(i) halo,
(ii) nitro,
(iii) $(C_1-C_6)$alkyl,
(iv) $(C_1-C_6)$alkoxy,
(v) halo-$(C_1-C_6)$alkyl,
(vi) halo-$(C_1-C_6)$alkoxy, and
(vii) hydroxy, and
(vii) $(C_1-C_6)$thioalkyl;
r is 1 to 5; provided that the sum of q and r is no greater than 5;
Z is selected from the group consisting of:
(i) a single bond,
(ii) divalent $(C_1-C_6)$alkyl unsubstituted or substituted with hydroxy, $(C_1-C_6)$alkyl, or $(C_1-C_6)$alkoxy,
(iii) divalent $(C_2-C_6)$alkenyl,
(iv) divaient $(C_2-C_6)$alkynyl, or
(v) a group of the formula —(C(R$^{14}$)$_2$)$_s$—R$^{15}$—or —R$^{15}$—(C(R$^{14}$)$_2$)$_s$—, wherein s is 0–6; wherein each R$^{14}$ substituent is independently selected from hydrogen, $(C_1-C_6)$-alkyl, or $(C_4-C_{10})$ cycloalkyl; and R$^{15}$ is selected from —O—, —S—, —SO—, —SO$_2$—, —SO$_2$—O—, —C(O)—, —OC(O)—, —C(O)O—, —NH—, —N(C$_1$–C$_6$alkyl)—, and —C(O)NH—, —NHC(O)—, N=N;
R$^{13}$ is independently selected from the group consisting of:

(i) $(C_4-C_{10})$heterocyclyl, (ii) heteroaryl, (iii) $(C_4-C_{10})$cycloalkyl unsubstituted or substituted with $(C_1-C_6)$alkyl, or (iv) phenyl unsubstituted or substituted with 1 to 5 substituents independently selected from: halo, hydroxy, nitro, $(C_1-C_{10})$ alkyl, $(C_1-C_{10})$alkoxy, halo-$(C_1-C_3)$alkoxy, halo-$(C_1-C_3)$ alkyl, $(C_1-C_3)$ alkoxyphenyl, phenyl, phenyl-$(C_1-C_3)$alkyl, $(C_1-C_6)$ alkoxyphenyl, pheny-$(C_1-C_3)$alkynyl, and $(C_1-C_6)$ alkylphenyl;

f) $(C_4-C_{10})$cycloalkyl unsubstituted or substituted with one or more substituents independently selected from the group consisting of:

(i) $(C_1-C_6)$alkyl, (ii) $(C_1-C_6)$alkoxy, (iii) $(C_1-C_6)$alkenyl, (iv) $(C_1-C_6)$alkynyl, (v) $(C_4-C_1)$cycloalkyl, (vi) phenyl, (vii) phenylthio, (viii) phenyl substituted by nitro, halo, $(C_1-C_6)$ alkanoyloxy, or carbocycloalkoxy, and (ix) a group represented by the formula $—Z—R^{13}$ wherein Z and $R^{13}$ are as defined above; and g) a group of the formula:

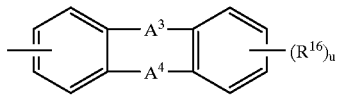

wherein $A^3$ and $A^4$ are each independently selected from (i) a bond, (ii) —O—, (iii) $—S(O)_t—$, wherein t is 0 to 2, (iv) $—C(R^{17})_2—$, wherein each $R^{17}$ substituent is independently selected from hydrogen, $(C_1-C_6)$alkyl, hydroxy, $(C_1-C_6)$alkyl, $(C_1-C_6)$alkoxy, or both $R^{17}$ substituents taken together are O, (v) $—N(R^{18})_2—$, wherein each $R^{18}$ substituent is independently selected from hydrogen; $(C_1-C_6)$alkyl; $(C_1-C_6)$alkenyl; $(C_1-C_6)$alkynyl; $(C_4-C_{10})$cycloalkyl; phenyl; phenyl substituted by nitro, halo, $(C_1-C_6)$alkanoyloxy; or both $R^{18}$ substituents taken together are $(C_4-C_{10})$cycloalkyl;

$R^{16}$ is $R^{12}$ or $R^{13}$ as defined above; and u is 0–4.

Another aspect of the invention relates to compositions for the treatment of susceptible bacterial infections comprising a compound of formula I in combination with an acceptable pharmaceutical carrier. Methods for the treatment of susceptible bacterial infections with compositions of formula I are also a part of this invention.

DETAILED DESCRIPTION OF THE INVENTION

The alkyl substituents recited herein denote substituted or unsubstituted, straight or branched chain hydrocarbons of the length specified. The term "alkenyl" refers to a substituted or unsubstituted, straight or branched alkenyl chain of the length specified. The term "alkynyl" refers to a substituted or unsubstituted, straight or branched alkynyl chain of the length specified.

The alkoxy substituents recited herein represent an alkyl group attached through an oxygen bridge. The term "alkenoxy" represents a alkenyl chain of the specified length attached to an oxygen atom.

The term "multicyclic aryl" means a stable, saturated or unsaturated, substituted or unsubstituted, 9 to 10 membered organic fused bicyclic ring; a stable, saturated or unsaturated, substituted or unsubstituted 12 to 14 membered organic fused tricyclic ring; or a stable, saturated or unsaturated, substituted or unsubstituted 14 to 16 membered organic fused tetracyclic ring. The bicyclic ring may have 0 to 4 substituents, the tricyclic ring may have 0 to 6 substituents, and the tetracyclic ring may have 0 to 8 substituents. Typical multi-cyclic aryls include fluorenyl, napthyl, anthranyl, phenanthranyl, biphenylene and pyrenyl.

The term "heteroaryl" represents a stable, saturated or unsaturated, substituted or unsubstituted, 4 to 7 membered organic monocyclic ring having a hetero atom selected from S, O, and N; a stable, saturated or unsaturated, substituted or unsubstituted, 9 to 10 membered organic fused bicyclic ring having 1 to 2 hetero atoms selected from S, O, and N; or a stable, saturated or unsaturated, substituted or unsubstituted, 12 to 14 membered organic fused tricyclic ring having a hetero atom selected from S, O, and N. The nitrogen and sulfur atoms of these rings are optionally oxidized, and the nitrogen hetero atoms are optionally quarternized. The monocyclic ring may have 0 to 5 substituents. The bicyclic ring may have 0 to 7 substituents, and the tricyclic ring may have 0 to 9 substituents. Typical heteroaryls include quinolyl, piperidyl, thienyl, piperonyl, oxafluorenyl, pyridyl and benzothienyl and the like.

The term "$(c_4-C_{10})$cycloalkyl" embraces substituents having from four to ten carbon atoms, such as cyclobutyl, cyclopentyl, cyclohexyl, and cycloheptyl which may be unsubstituted or substituted with substituents such as alkyl and phenyl. This term also embraces $C_5$ to $C_{10}$ cycloalkenyl groups such as cyclopentenyl and cyclohexenyl. The term "$(C_4-C_{10})$cycloalkyl" also embraces bicyclic and tricyclic cycloalkyls such as bicyclopentyl, bicylohexyl, bicycloheptyl, and adamantyl.

The term "alkanoyloxy" represents an alkanoyl group attached through an oxygen bridge. These substituents may be substituted or unsubstituted, straight, or branched chains of the specified length.

The term "cyano-$(C_1-C_6)$alkoxy" represents a substituted or unsubstituted, straight or branched alkoxy chain having from one to six carbon atoms with a cyano moiety attached to it.

The term "divalent $(C_1-C_6)$alkyl" represents an unsubstituted or substituted, straight or branched divalent alkyl chain having from one to six carbon atoms. Typical divalent $(C_1-C_6)$alkyl groups include methylene, ethylene, propylene, isopropylene, butylene, isobutylene, sec-butylene, t-butylene, pentylene, neo-pentylene, and hexylene. Such divalent $(C_1-C_6)$alkyl groups may be substituted with substituents such as alkyl, alkoxy, and hydroxy.

The term "divalent $(C_2-C_6)$alkenyl" represents a straight or branched divalent alkenyl chain having from two to six carbon atoms. Typical divalent $(C_2-C_6)$alkenyl include ethenyl, 1-propenyl, 2-propenyl, 1-butenyl, 2-butenyl and the like.

The term "divalent $(C_2-C_6)$alkynyl" represents a straight or branched divalent alkynyl chain having from two to six carbon atoms. Typical divalent $(C2-C_6)$alkynyl include ethynylene, 1-propynylene, 2-propynylene, 1-butynylene, 2-butynylene and the like.

The term "halo" represents chloro, fluoro, bromo or iodo.

The term "halo-$(C_1-C_6)$alkyl" represents a straight or branched alkyl chain having from one to six carbon atoms with from 0 to 3 halogen atoms attached to each carbon. Typical halo-$(C_1-C_6)$alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

The term "halo-$(C_1-C_6)$alkoxy" represents a straight or branched alkoxy chain having from one to six carbon atoms with from 0 to 3 halogen atoms attached to each carbon. Typical halo-$(C_1-C_6)$alkoxy groups include chloromethoxy, 2-bromoethoxy, 1-chloroisopropoxy, 3-fluoropropoxy, 2,3-dibromobutoxy, 3-chloroisobutoxy, iodo-t-butoxy, trifluoromethoxy, and the like.

The term "heterocyclyl" embraces saturated groups having three to ten ring members and which heterocyclic ring contains a hetero atom selected from oxygen, sulfur and nitrogen, examples of which are piperazinyl, morpholino, piperdyl, methylpiperdyl, azetidinyl, and aziridinyl.

The invention includes salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, acetic acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The compounds of the present invention are prepared from compounds of the formula:

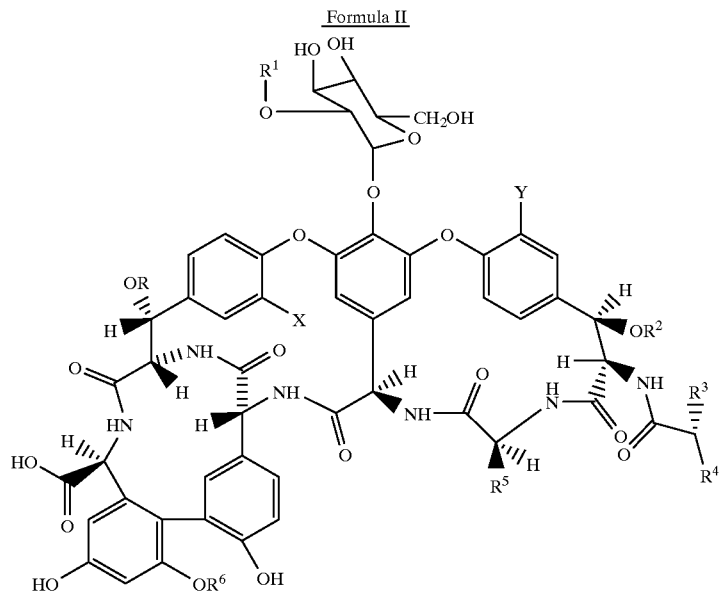

Formula II

The compounds of formula II are defined in Table 1.

TABLE 1

| | | | | Formula II Compounds[a] | | | | |
|---|---|---|---|---|---|---|---|---|
| antibiotic | R | $R^1$ | $R^2$ | $R^3$ | $R^4$ | $R^5$ | $R^6$ | X | Y |
| vancomycin | 4-epi | 4-epi | H | $NHCH_3$ | $CH_2CH(CH_3)_2$ | $CH_2(CO)NH_2$ | H | Cl | Cl |
| A82846A | 4-epi | 4-epi | H | $NHCH_3$ | $CH_2CH(CH_3)_2$ | $CH_2(CO)NH_2$ | H | H | Cl |
| A82846B | 4-epi | 4-epi | H | $NHCH_3$ | $CH_2CH(CH_3)_2$ | $CH_2(CO)NH_2$ | H | Cl | Cl |
| A82846C | 4-epi | 4-epi | H | $NHCH_3$ | $CH_2CH(CH_3)_2$ | $CH_2(CO)NH_2$ | H | H | H |
| PA-42867-A | 4-epi | 4-epi | H | $NHCH_3$ | $CH_2CH(CH_3)_2$ | $CH_2(CO)NH_2$ | H | Cl | H |
| PA-42867-C | 4-epi | 4-epi | H | $NHCH_3$ | $CH_2CH(CH_3)_2$ | $CH_2(CO)NH_2$ | H | H | H |
| PA-42867-D | 4-epi | 4-epi | H | $N(CH_3)_2$ | $CH_2CH(CH_3)_2$ | $CH_2(CO)NH_2$ | H | Cl | H |
| A83850A | H | keto | H | $N(CH_3)_2$ | $CH_2CH(CH_3)_2$ | $CH_2(CO)NH_2$ | H | Cl | Cl |
| A83850B | H | keto | H | $NHCH_3$ | $CH_2CH(CH_3)_2$ | $CH_2(CO)NH_2$ | H | Cl | Cl |
| actinioidin | actin | acos | H | $NH_2$ | p-OH,m-Cl-phenyl | benzyl | man | Cl | H |
| avoparcin | risto | risto | man | $N(CH_3)_2$ | p-rha-phenyl | p-OH-phenyl | H | H | H |
| galacardin | risto | risto | man | $NHCH_3$ | p-gal-gal-phenyl | p-OH-phenyl | H | Cl | H |
| helevecardin | risto | risto | H or man | $NHCH_3$ | p-$CH_3$O-rha-phenyl | p-OH,m-Cl-phenyl | H | Cl | H |
| M47767 | actin | acos | H | $NHCH_3$ | p-OH,m-Cl-phenyl | benzyl | man | Cl | H |

[a]Abbreviations for the formula II compounds are: actin = actinosaminyl; acos = acosaminyl; 4-epi = 4-epi-vancosaminyl; gal = galactosyl; keto = 4-keto-vancosaminyl; man = mannose; rha = rhamnosyl; rha-gal = rhamnosyl-galactosyl; risto = risotsaminyl; van = vancosaminyl.

In a preferred embodiment of the invention, the formula I compounds are prepared from the A82846 antibiotics (A82846A, A82846B, and A82846C) and PA-42867-A. In a more preferred embodiment, the compounds of the present invention are prepared from A82846B ("A82846B derivatives"). A82846B is represented by formula I compounds wherein R is 4-epi-vancosaminyl, $R^1$ is hydrogen, $R^2$ is $NHCH_3$, $R^3$ is $CH_2CH(CH_3)_2$, $R^4$ is $CH_2(CO)NH_2$, $R^5$ is hydrogen, $R^6$ is 4-epi-vancosaminyl and X and Y are Cl. A82846B derivatives of the present invention having substituents at position $R^7$ of formula I are list herein in the manner "$R^7$—A82846B". For example, the compound "phenylbenzyl-A82846B" has a phenylbenzyl substituent at position $R^7$ in formula I.

Preferred formula I compounds include those A82846B derivatives wherein $R^7$ is —($C_1$–$C_{12}$-alkyl)-$R^8$, with —$CH_3$—$R^8$ being more preferred, and $R^8$ is an unsubstituted multicyclic aryl. Of this group, naphthylmethyl-A82846B, acenapthlenyl-methyl-A82846B, and fluorenylmethyl-A82846B are more preferred.

Preferred formula I compounds also include those A82846B derivatives wherein $R^7$ is —($C_1$–$C_{12}$-alkyl)-$R^8$, with —$CH_3$—$R^8$ being more preferred, and $R^8$ is an unsubstituted heteroaryl or a heteroaryl substituted by halophenyl. Of this group, [1-oxa]fluorenylmethyl-A82846B, chlorophenylbenzoxazolemethyl-A82846B, and phenylthienylmethyl-A82846B are more preferred.

Further preferred compounds of formula I include those A82846B derivatives wherein $R^7$ is —($C_1$–$C_{12}$-alkyl)-$R^8$, with —$CH_3$—$R^8$ being more preferred, and $R^8$ is a group of the formula:

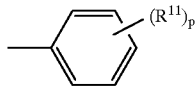

wherein p is 1 and $R^{11}$ is selected from ($C_2$–$C_5$)alkenyloxy, halo-($C_1$–$C_6$)alkoxy, ($C_2$–$C_{10}$)alkanoyloxy, ($C_1$–$C_3$)alkoxy substituted with ($C_1$–$C_4$)alkylthio, and diphenyl-($C_1$–$C_6$) alkyl. Of this group, trifluromethoxybenzyl-A82846B, diphenylmethylbenzyl-A82846B, thiopropylethoxybenzyl-A82846B, acetoxybenzyl-A82846B, nonanoyloxybenzyl-A82846B, and tetrafluoroethoxybenzyl-A82846B are more preferred.

Still further preferred compounds of formula I include those A82846B derivatives wherein $R^7$ is —($C_1$–$C_{12}$-alkyl)-$R^8$, with —$CH_3$—$R^8$ being more preferred, and $R^8$ is a group of the formula:

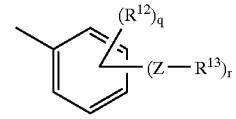

wherein q is 1 to 5; r is 1; Z is selected from a single bond, divalent ($C_1$–$C_6$)alkyl, divalent ($C_2$–$C_6$)alkenyl, and —$R^{15}$—$(C(R^{14})_2)_s$—, wherein $R^{15}$ is selected from —O—, —S—, —$SO_2$—, and —OC(O)—, each $R^{14}$ substituent is hydrogen, and s is 0 or 1; and $R^{13}$ is selected from: ($C_4$–$C_{10}$)cycloalkyl; phenyl; and phenyl substituted by nitro, halo, ($C_1$–$C_{10}$)alkyl, ($C_1$–$C_{10}$)alkoxy, or halo($C_1$–$C_3$)alkyl. Of this group, chlorophenylbenzyl-A82846B, phenylbenzyl-A82840B, benzylbenzyl-A82846B, methylphenylbenzyl-A82846B, pentylphenylbenzyl-A82846B, methoxyphenylbenzyl-A82346B, pentoxyphenylbenzyl-A82846B, nitrophenoxybenzyl-A82846B, fluorophenylbenzyl-A82846B, phenylethynylbenzyl-A82846B, phenoxybenzyl-A82846B, benzyloxybenzyl-A82846B, nitrophenylbenzyl-A82846B, chlorophenoxybenzyl-A82846B, chlorobenzyloxybenzyl-A82846B, butylphenoxybenzyl-A82846B, trifluoromethylphenoxybenzyl-A82846B, dichlorophenoxybenzyl-A82846B, nitrobenzyloxybenzyl-A82846B, benzoyloxybenzyl-A82846B, cyclohexyloxybenzyl-A82846B, cyclohexanoyloxybenzyl-A82846B, thiophenylbenzyl-A82846B, chlorophenylsulfonylbenzyl-A82846B, and cyclohexylbenzyl-A82846B, cyclohexylethoxybenzyl- A82846B chlorophenoxynitro-benzyl-A82846B benzylmethoxybenzyl-A82846B, chlorophenoxynitro-benzyl-A82846B, and phenoxymethoxybenzyl-A82846B, benzoyloxy-dimethoxybenzyl-A82846B, cyclohexanoyloxy-dimethylbenzyl-A82846B, trifluoromethylphenylbenzyl-A82846B, butylphenylthiobenzyl-A82846B, and bromophenylbenzyl-A82846B more preferred.

Still further preferred compounds of formula I include A82846B derivatives wherein $R^7$ is —($C_1$–$C_{12}$-alkyl)-$R^8$, with —$CH_3$—$R^8$ being more preferred, and $R^8$ is ($C_4$–$C_{10}$) cycloalkyl substituted with ($C_4$–$C_{10}$)cycloalkyl. Of this group of compounds, more preferred is cyclohexyl-cyclohexylmethyl-A82246B and butyl- cyclohexylmethyl-A82846B.

Formula I compounds that are prepared from A83850A or A83850B can be prepared from the reduced forms of these compounds. The reduced forms of compounds A83850A or A83850B are produced according to the method described in U.S. Pat. No. 5,187,082, which is incorporated herein by reference.

The compounds of this invention are prepared by reacting a formula II compound with an aldehyde to form an intermediate Schiff's base, which is subsequently reduced with a metal borohydride to give the desired N-alkyl amine.

In the first method of making the compounds of this invention, hereinafter Method A (described in Examples 1 and 2), the reaction for the formation of the Schiff's base is carried out under an inert atmosphere, such as nitrogen or argon, in a polar solvent, such as dimechylformamide (DMF) or methanol (MeOH), or a mixture of polar solvents, such as a mixture of dimethylformamide and methanol, at a temperature of about 25° C. to about 100° C. The reaction is preferably carried out at a temperature from about 60° C. to about 70° C. for 30 minutes to 2 hours in a mixture of dimethylformamide and methanol, or in methanol. The intermediate Schiff's base is then reduced, preferably without isolation, to produce the corresponding N-alkyl derivative(s). The reduction of the Schiff's base can be effected using a chemical reducing agent such as a metal borohydride, for example, sodium borohydride or sodium cyanoborohydride. The reduction reaction can be carried out in a polar organic solvent, such as dimethylformamide, methanol, or a mixture of polar solvents, such as a mixture of dimethylformamide and methanol. The reduction reaction can be carried out at a temperature of about 25° C. to about 100° C. for 1 to 5 hours. The reduction reaction is preferably carried out using an excess of sodium cyanoborohydride in a mixture of dimethylformamide and methanol or in methanol at about 60° C. to about 70° C. for 1 to 2 hours. Method A is preferable for benzylic aldehydes.

In a second method of making compounds of this invention, hereinafter Method B (described in Example 3), the formation of the Schiff's base is carried out under an inert atmosphere, such as nitrogen or argon, in the presence of the reducing agent, sodium cyanoborohydride, in a polar solvent, such as dimethylformamide, methanol, or a mixture of polar solvents, such as a mixture of dimethylformamide and methanol, at a temperature of about 25° C. to about 100° C. for 1 to 5 hours. The reaction is preferably carried out at a temperature from about 60° C. to about 70° C. for 1 to 2 hours in a mixture of dimethylformamide and methanol. Method B is preferable for non-benzylic aldehydes.

In a third method of making compounds of this invention, hereinafter Method C (described in Example 4), the formation of the Schiff's base is carried out a) under an inert atmosphere, such as nitrogen or argon, b) in the presence of the reducing agent, such as a metal borohydride, with sodium cyanoborohydride being most preferred, or a homogenous or heterogeneous catalytic hydrogenation agent(s), such as Crabtree's catalyst, Wilkinson's catalyst, palladium on carbon, platinum on carbon, or rhodium on carbon, c) in a polar solvent, such as dimethylformamide, methanol, or a mixture of polar solvents, such as a mixture of dimethylformamide and methanol, and d) at a temperature of about 25° C. to about 100° C. The reaction is preferably carried out at a temperature from about 60° C. to about 70° C. in methanol. The reaction is allowed to continue for about 20 to about 28 hours, at which time the reaction mixture is adjusted to about pH 7.5 to about pH 10, with a pH of about 9.0 being preferred. The pH adjustment halts the reaction. Because the product is marginally soluble in polar solvents, the solvent of the reaction can be exchanged to an alcohol such as ethanol, butanol, or isopropanol, with isopropanol being preferred, to allow for precipitation of the product. Method C is a preferred method of this invention in view of the increased product yield provided by this method. Another advantage of this reaction scheme is the increased ratio of preferred product (products substituted at the amino group of the sugar denoted as $R^1$ in Formula II compounds) to other products (products that are substituted at the amino groups of substitutents denoted as R and/or $R^3$ of the Formula II compounds). By allowing the reaction to proceed for an extended period of time, such as 20 to 28 hours, products that are monosubstituted at positions denoted as R and $R^3$ in the Formula II compounds are converted to disubstituted forms, making the preferred monosubstituted derivative easier to isolate.

The products of the reaction, obtained from either Method A, B, or C can be purified by preparative reverse-phase HPLC utilizing Waters C18 Nova-Pak columns with ultraviolet light (UV; 235 nm or 280 nm) detection. A 30 minute gradient solvent system consisting of 95% aqueous buffer/5% $CH_3CN$ at time=0 minutes to 20% aqueous buffer/80% $CH_3CN$ at time=30 minutes is typically used, where the aqueous buffer is either TEAP (0.5% aqueous triethylamine adjusted to pH=3 with phosphoric acid) or TFA (0.1% trifluoroacetic acid overall concentration).

HPLC analysis of the reaction mixtures and final purified products can be accomplished utilizing a Waters C18 MicroBonda-Pak column (typically 3.9×300 mm steel) or Waters Nova-pak C18 RCM column (8×100 mm) with UV (235 nm or 280 nm) detection. A 30 minute gradient solvent system consisting of 95% aqueous buffer/5% $CH_3CN$ at time=0 minute to 20% aqueous buffer/80% $CH_3CN$ at time=30 minutes is typically used, where the aqueous buffer is either TEAP (0.5% aqueous triethylamine adjusted to pH=3 with phosphoric acid) or TFA (0.1% trifluoroacetic acid overall concentration).

The ratio of the aldehyde to the formula II compound and the reaction conditions determines the products of the reaction. The monosubstituted derivatives are those derivatives where a hydrogen atom of the amino group at position $R^1$ in formula II is replaced by one of the substituents listed above for formula I. When using Methods A or B, described above, the formation of monosubstituted derivatives substituted at the amino group of the amino sugar at position $R^1$ in the formula II compounds is favored by using a slight excess of aldehyde, a shorter reaction time, and a lower temperature. As noted above, Method C favors the formation of the monosubstituted derivative. The monosubstituted derivative is preferred. A large excess of the aldehyde favors the formation of disubstituted and trisubstituted derivatives of the formula II compounds. The disubstituted derivatives are the derivatives where a hydrogen atom at two of the locations selected from the amino group at position $R^3$, and the amino group of the amino sugars designated as R or $R^1$ in formula II, are replaced by the reduced aldehyde moiety. The trisubstituted derivatives are the derivatives where a hydrogen atom at three of the locations selected from the amino group at position $R^3$, and the amino group of the amino sugars designated as R or $R^1$ in formula II, are replaced by the reduced aldehyde moiety.

A further object of this invention are those compounds that are monosubstituted at the amino group of the amino sugar at position R of formula II, when such an amino sugar is present at this position, or at the amino group at position $R^3$ of formula II. Further, the disubstituted and trisubstituted derivatives referred to above are also objects of this invention. These derivatives are useful in the treatment of bacterial infections. Methods A, B, and C (described above, and in the Examples) can be used to produce the monosubstituted, disubstituted and trisubstituted derivatives.

Preferably, Method D, described in Example 5, is used to produce those derivatives that are monosubstituted at the amino group at position $R^3$ of formula II. Method D is also preferred for The synthesis of disubstituted derivatives substituted at the amino group of the amino sugar designated as $R^1$ in the formula II compounds, and at the amino group at position $R^3$ in the formula II compounds.

Preferably, Method E, as described in Example 5, is used to produce those disubstituted derivatives that are substituted at the amino groups of the amino sugars designated as $R^1$ and R in the formula II compounds. Method E is also preferably used to produce the trisubstituted derivatives. The trisubstituted compounds can be formed when there is an amino sugar at the position designated as R in the formula II compounds.

Examples of compounds that have been prepared and are illustrative of the formula I compounds are listed in Tables 2A, 2B, and 2C. Table 2A lists compounds prepared by reacting an aldehyde with the glycopeptide A82846B. Table 2A lists the sidechain substitutions on the amino group of the 4-epi-vancosaminyl sugar of the 4-epi-vancosaminyl-O-glycosyl disaccharide of the A82346B compound. All of the compounds listed are monosubstituted derivatives.

Table 2B lists those compounds that were prepared by reacting an aldehyde with a variety of alycopeptide antibiotics other than A82846B. The compounds of Table 2B are monosubstituted at the amino group of the amino sugar designated as $R^1$ in formula II with the sidechain listed. All of the compounds listed are monosubstituted derivatives.

Table 2C lists exemplary compounds prepared by reacting an aldehyde with the glycopeptide A82846B. The compounds listed in Table 2C are substituted with the sidechain listed at the postions listed. The substituent positions listed are those refered to in formula II.

TABLE 2A

| COMPOUND NO. | SIDECHAIN |
| --- | --- |
| 1 | 2-napthylmethyl |
| 2 | 4-phenylbenxyl |
| 3 | 1-napthylmethyl |
| 4 | 4-phenoxybenzyl |
| 5 | 4-benzyloxybenzyl |
| 6 | 4-trifluoromethoxybenzyl |
| 7 | 4-allyloxylbenzyl |
| 8 | 4-nonyloxybenzyl |
| 9 | 2-methoxy-1-napthylmethyl |

TABLE 2A-continued

| COMPOUND NO. | SIDECHAIN |
| --- | --- |
| 10 | 4-dodecyloxybenzyl |
| 11 | 9-phenanthranylmethyl |
| 12 | 4-decyloxybenzyl |
| 13 | 9-anthranylmethyl |
| 14 | 4-[phenylethynyl]4-phenylbenzyl |
| 15 | 4-methoxy-1-napthylmethyl |
| 16 | 1-pyrenylmethyl |
| 17 | 9-[10-methyl]anthranylmethyl |
| 18 | 9-[10-chloro]anthranylmethyl |
| 19 | 2-benzthienylmethyl |
| 20 | 4-[4-hydroxyphenyl]benzyl |
| 21 | 4-[4-octylphenyl]benzyl |
| 22 | 4-[4-pentylphenyl]benzyl |
| 23 | 4-[4-octyloxyphenyl]benzyl |
| 24 | 3-pyridylmethyl |
| 25 | 5-nitro-1-naphthylmethyl |
| 26 | 4-pyridylmethyl |
| 27 | 4-quinolylmethyl |
| 28 | 3-quinolylmethyl |
| 29 | 4-stilbenzyl |
| 30 | 2-quinolylmethyl |
| 31 | 2-pyridylmethyl |
| 32 | 2-fluorenylmethyl |
| 33 | 4-phenoxyphenethyl |
| 34 | 4-[4-pentylcyclohexyl]benzyl |
| 35 | 4-benzylphenethyl |
| 36 | 4-[4-biphenyl]benzyl |
| 37 | 4-trifluoromethylbenzyl |
| 38 | trans-cinnamyl |
| 39 | 4-[1-oxa]fluorenylmethyl |
| 40 | 4-[4-pentoxyphenyl]benzyl |
| 41 | 4-thiomethylbenzyl |
| 42 | 2,3-[2-methyl-3-[4-t-butylphenyl]]propenyl |
| 43 | 9-(1-methyl)-acridinylmethyl |
| 44 | 2-hydroxy-1-naphthylmethyl |
| 45 | 4-[2-phenyl-6-methoxy]quinoylmethyl |
| 46 | 4-diphenylmethylbenzyl |
| 47 | 3,4 cyclohexenylmethyl |
| 48 | 3,4-methylenedioxylbenzyl |
| 49 | 3-phenoxybenzyl |
| 50 | 4-benzylbenzyl |
| 51 | 3-benzyloxy-6-methoxy benzyl |
| 52 | 4-benzyloxy-3-methoxybenzyl |
| 53 | 3,4-dibenzyloxybenzyl |
| 54 | 4-[4-methoxyphenyl]benzyl |
| 55 | 4-[3-cyanopropoxy]benzyl |
| 56 | 3,4-ethylenedioxybenzyl |
| 57 | 4-[4-nitrophenoxy]benzyl |
| 58 | 2,3-methylenedioxybenzyl |
| 59 | 2-benzyloxyphenethyl |
| 60 | 2-ethoxy-1-naphthylmethyl |
| 61 | 2-benzylfurylmethyl |
| 62 | 3-phenoxyphenethyl |
| 63 | 4-phenoxyphenethyl |
| 64 | 4[4-nitrophenyl]benzyl |
| 65 | 6-methoxy-2-naphthylmethyl |
| 66 | 3-methyl-5-thienylmethyl |
| 67 | 5-phenyl-2-thienylmethyl |
| 68 | 4-benzyloxyphenethyl |
| 69 | 3-benzyloxyphenethyl |
| 70 | 4-[2-nitrophenoxy]benzyl |
| 71 | 5-[4-methoxyphenyl]-2-thienylmethyl |
| 72 | 4-difluormethoxybenzyl |
| 73 | 2,3,4,5,6-pentamethylbenzyl |
| 74 | 5-iodo-2-thienylmethyl |
| 75 | 4-[2-[2-chloroethoxy]ethoxy]benzyl |
| 76 | 3,4-dimethylbenzyl |
| 77 | 3-acetoxybenzyl |
| 78 | 4-nitrobenzyl |
| 79 | 4-phenylethynylbenzyl |
| 80 | 4-[2-chloro-6-fluorobenzyloxy]benzyl |
| 81 | 4-[3,4-dichlorophenoxy]benzyl |
| 82 | 5-[2,3-dihydrobenzfuryl]methyl |
| 83 | 4-[2-(N,N-diethylamino)ethoxy]benzyl |
| 84 | 2-bicyclo[2.1.2]heptylmethyl |
| 85 | 2-hydroxy-5-phenylbenzyl |
| 86 | 3-[4-chlorophenoxy]benzyl |

TABLE 2A-continued

| COMPOUND NO. | SIDECHAIN |
|---|---|
| 87 | 4-[3-chlorophenoxy]-3-nitrobenzyl |
| 88 | 4-[2-chlorophenoxy]-3-nitrobenzyl |
| 89 | 3,5-dimethylbenzyl |
| 90 | 4-[4-ethylphenyl]benzyl |
| 91 | 3-phenylbenzyl |
| 92 | 4-[3-fluorophenyl]benzyl |
| 93 | 4-[4-chlorobenzyloxy]benzyl |
| 94 | 4-[4-chlorophenoxy]-3-nitrobenzyl |
| 95 | 4-[4-methylphenoxy]benzyl |
| 96 | 4-[4-t-butylphenoxy]benzyl |
| 97 | 4-[4-methylphenyl]benzyl |
| 98 | 4-[4-methoxyphenoxy]benzyl |
| 99 | 4-[4-acetoxy-3-methoxybenzyl |
| 100 | 4-[(2-phenyl)ethyl]benzyl |
| 101 | 3-[5-phenyl]pyridinylmethyl |
| 102 | 4-[2-nitrophenyl]benzyl |
| 103 | 2-[1-hydroxy]fluorenylmethyl |
| 104 | 4-benzyl-3-methoxybenzyl |
| 105 | 4-[cyclohexylmethoxy]-3-ethoxybenzyl |
| 106 | 3-[3,3'-dichlorophenoxy]benzyl |
| 107 | 4-[4-propylphenyl]benzyl |
| 108 | 4-thiophenylbenzyl |
| 109 | 4-[alpha-hydroxybenzyl]benzyl |
| 110 | 2,2-dinitro-4-thiophenebenzyl |
| 111 | 3-[3-trifluoromethylphenoxy]benzyl |
| 112 | 4-[t-butylethynyl]benzyl |
| 113 | 4-phenoxy-3-methoxy-benzyl |
| 114 | 4-[3-tribluoromethylphenoxy]-3-nitrobenyl |
| 115 | 2-phenylthiobenzyl |
| 116 | 2-[4-chlorphenyl]-6-benzoxazolemethyl |
| 117 | 4-[alpha-methoxybenzyl]benzyl |
| 118 | 4-cyclohexylbenzyl |
| 119 | 3-[3,4-dichlorophenoxy]benzyl |
| 120 | acenaphthlenylmethyl |
| 121 | 4-[1,1,2,2-tetrafluoroethoxy]benzyl |
| 122 | 4-benzoyloxy-3,3'-dimethoxybenzyl |
| 123 | 3-[cyclohexylmethoxy]benzyl |
| 124 | 4-cyclohexyloxybenzyl |
| 125 | 3-[2-quinoylmethoxy]benzyl |
| 126 | 4-[alpha-ethoxybenzyl]benzyl |
| 127 | 4-[cyclohexylethoxy]benzyl |
| 128 | 4-[alpha-propoxybenzyl]benzyl |
| 129 | 4-[4-methyl-1-piperidino]benzyl |
| 130 | 2-thiophene-1,2-cyclohexenylmethyl |
| 131 | 4-[4-nitrobenzylocy]benzyl |
| 132 | 3-[4-trifluoroimethylphenoxy]benzyl |
| 133 | 3-benzoyl-2,4-dichlorobenzyl |
| 134 | 4-[2-(2-thiopropyl)ethoxy]benzyl |
| 135 | 4-[2-methyl-1-piperidino]benzyl |
| 136 | 4-hydroxybenzyl |
| 137 | 4-[2-pyridyl]benzyl |
| 138 | 4-acetoxybenzyl |
| 139 | 5,6-benzonorbornylmethyl |
| 140 | 3-phenylcyclopentylmethyl |
| 141 | 1-adamantylmethyl |
| 142 | 3-[cyclohexylmethoxy]-4-methoxybenzyl |
| 143 | 2-[2-glucosyl]benzyl |
| 144 | 4-[4-pentoxybiphenyl]benzyl |
| 145 | 3,4-dihydroxybenzyl |
| 146 | 4-[4-methylpiperazino]benzyl |
| 147 | 4-morpholinobenzyl |
| 148 | 4-[4-chlorophenylsulfonyl]benzyl |
| 149 | 4-methylsulfonyloxybenzyl |
| 150 | 4-benzoyloxybenzyl |
| 151 | 5-phenyl-3-pyridinylmethyl |
| 152 | 4-[N,N-bis(2-chloroethyl)amino]benzyl |
| 153 | 3-cyclohexyloxybenzyl |
| 154 | 4-[2-t-butoxyethoxy]benzyl |
| 155 | 3,3'-dichloro-4-hydroxy-benzyl |
| 156 | 1,2,3,4-tetrahydro-9-anthranylmethyl |
| 157 | 4-cyclohexanolyloxybenzyl |
| 158 | 4-nonanoyloxybenzyl |
| 159 | 4-[phenylsulfinyl]benzyl |
| 160 | 4-anilinobenzyl |
| 161 | cyclohexylmethyl |
| 162 | 3-benzoyloxybenzyl |
| 163 | 3-nonanoyloxybenzyl |
| 164 | 4-[cyclohexyl]cyclohexylmethyl |
| 165 | 3-cyclohexanoyloxybenzyl |
| 166 | 4-[cyclohexanoyloxy]-3,3'-[dimethoxy]benzyl |
| 167 | 4-[nonanoyloxy]-3,3'-[dimethoxy]benzyl |
| 168 | 1,2,3,4-tetrahydro-6-naphthylmethyl |
| 169 | 2-hydroxybenzyl |
| 170 | [2-[6,6-dimethyl-bicyclo[3.1.1]hept-2-enyl]methyl |
| 171 | 1-cyclohexenyl-4-isopropylmethyl |
| 172 | 4-[4-methoxyphenyl]butyl |
| 173 | 4-[[2,3,4,5,6-pentamethyl]phenylsulfonylocy]benzyl |
| 174 | 4-[1-pyrrolidinosulfonyl]benzyl |
| 175 | 3-[4-methoxyphenyl]propyl |
| 176 | 8-phenyloctyl |
| 177 | 4-[2,3-dihydroxypropoxy]benzyl |
| 178 | 4-[N-methylanilino]benzyl |
| 179 | 2-[2-napthyl]ethyl |
| 189 | 6-methyl-2-naphthylmethyl |
| 190 | cis-bicyclo[3.3.0]octane-2-methyl |
| 191 | 2-tridecynyl |
| 192 | 4-butyl-2-cyclohexylmethyl |
| 193 | 4-[(4-fluorobenzoyl)amino]benzyl |
| 194 | 4-[(3-fluorobenzoyl)amino]benzyl |
| 195 | 8-phenoxyoctyl |
| 196 | 6-phenylhexyl |
| 197 | 10-phenyldecyl |
| 198 | 8-bromooctyl |
| 199 | 11-tridecynyl |
| 200 | 8-[4-methoxyphenoxy]octyl |
| 201 | 8-[4-phenylphenoxy]octyl |
| 202 | 8-[4-phenoxyphenoxy]octyl |
| 203 | 3-[3-trifluoromethylphenoxy]benzyl |
| 204 | 10-undecenyl |
| 205 | 4-cyclohexylbutyl |
| 206 | 4-phenyl-2-fluorobenzyl |
| 207 | 7-hexadecynyl |
| 208 | 3-[cyclopentyl]propyl |
| 209 | 4-[2-methylphenyl]benzyl |
| 210 | 4-[pheylazo]benzyl |
| 211 | 4-[4-fluorophenyl]benzyl |
| 212 | 3-nitro-4-[4-nitrophenyl]benzyl |
| 213 | 3-nitro-4-[2-nitrophenyl]benzyl |
| 214 | 9-decenyl |
| 215 | 4-[3,4-dimethoxyphenyl]benzyl |
| 216 | 4-[4-trifluromethylphenyl]benzyl |
| 217 | 5-hexenyl |
| 218 | 4-[2-thienyl]benzyl |
| 219 | 4-[6-phenylhexylocy]benzyl |
| 220 | 9,10-dihydro-2-phenantrene methyl |
| 221 | 4-[3,4-dimethylphenyl]benzyl |
| 222 | 4-[4-methyphenyl]-2-methylbenzyl |
| 223 | 4-[3-phenylpropyloxy]benzyl |
| 224 | 4-[3-methylphenyl]benzyl |
| 225 | 4-[4-methylphenyl]-3-methylbenzyl |
| 226 | 4-[4-pentenyloxy]benzyl |
| 227 | 4-[1-heptynyl]benzyl |
| 228 | 3-[4-t-butyl-phenylthio]benzyl |
| 229 | 4-[4-chlorophenyl]benzyl |
| 230 | 4-[4-bromophenyl]benzyl |
| 231 | 40[4-cyanophenyl]benyl |
| 232 | 4-[1-nonyl]benzyl |
| 233 | 4-[11-tridecynyloxy]benzyl |
| 234 | 12-phenyldodecyl |
| 235 | 6-phenyl-5-hexynyl |
| 236 | 11-phenyl-10-undecynyl |
| 237 | 4-[2-methylphenyl]-3-methylbenzyl |
| 238 | 3-[2'-thienyl]-2-thienylmethyl |
| 239 | 4-[benzyloxymethyl]cyclohexylmethyl |
| 240 | 4-[4-chlorophenoxy]benzyl |
| 241 | 4-[benzyl]cyclohexylmethyl |
| 242 | 4-benzoylbenzyl |
| 243 | 4-[phenoxymethyl]benzyl |
| 244 | 4-[4-chlorobenzyl]benzyl |

TABLE 2B

| COMPOUND NO. | GLYCOPEPTIDE CORE | SIDECHAIN |
|---|---|---|
| 180 | vancomycin | 1-napthylmethyl |
| 181 | vancomycin | 4-phenylbenzyl |
| 182 | A82846A | 4-phenylbenzyl |
| 183 | A82846C | 4-phenylbenzyl |
| 184 | A82846C | 4-phenoxybenzyl |
| 185 | PA-42867 A | 4-phenylbenzyl |
| 186 | reduced A838450A | 4-phenylbenzyl |
| 187 | alpha-avoparcin | 4-phenylbenzyl |
| 188 | beta-avoparcin | 4-phenylbenzyl |

TABLE 2C

| COMPOUND NO. | SIDECHAIN | R | R1 | R3 |
|---|---|---|---|---|
| 245 | 4-nitrobenzyl | x | x | |
| 246 | 8-benzyloctyl | | x | x |
| 247 | 4-phenoxybenzyl | | x | x |
| 248 | 4-phenylbenxyl | x | x | |
| 249 | 4-phenylbenxyl | x | x | x |
| 250 | 4-phenylbenxyl | | | x |
| 251 | 4-phenylbenxyl | | x | x |
| 252 | 4-[4-chlorophenyl]benzyl | | | x |
| 253 | 4-[4-chlorophenyl]benzyl | | x | x |
| 254 | 4-[4-chlorophenyl]benzyl | x | x | |
| 255 | 4-[4-chlorophenyl]benzyl | x | x | x |
| 256 | 4-hydroxybenzyl | | x | x |
| 257 | 4-hydroxybenzyl | | | x |
| 258 | 1,2,3,4-tetrahydro-6-naphthylmethyl | | x | x |
| 259 | 1,2,3,4-tetrahydro-6-naphthylmethyl | | | x |
| 260 | 4-[N-methylanilino]benzyl | | x | x |
| 261 | 3,3,'-dichloro-4-hydroxy-benzyl | | x | x |
| 262 | 1,2,3,4-tetrahydro-9-anthranylmethyl | | x | x |

TABLE 2C-continued

| COMPOUND NO. | SIDECHAIN | R | R1 | R3 |
|---|---|---|---|---|
| 263 | 4-[4-nitrophenyl]benzyl | | x | x |
| 264 | 2-hydroxybenzyl | | x | x |
| 265 | 3,4-methylenedioxylbenzyl | | x | x |
| 266 | 3-benzyloxy-6-methoxy benzyl | | x | x |
| 267 | 4-[4-nitrophenoxy]benzyl | | x | x |
| 268 | 4-benzyloxy-3-methoxybenzyl | | x | x |
| 269 | 2,3-methylenedioxybenzyl | | x | x |
| 270 | 4-benzylbenzyl | | x | x |
| 271 | 3-phenoxybenzyl | | x | x |
| 272 | 4-trifluoromethylbenzyl | x | x | |
| 273 | 4-[1-oxa]fluorenylmethyl | | x | x |
| 274 | 4-pyridylmethyl | | x | x |
| 275 | 3-quinolylmethyl | x | x | |
| 276 | 2-benzthienylmethyl | | x | x |
| 277 | 4-[2-phenyl-6-methoxy]quinoylmethyl | | x | x |
| 278 | 4-thiomethylbenzyl | x | x | |
| 279 | 2-fluorenylmethyl | x | x | |
| 280 | 3-pyridylmethyl | | x | x |
| 281 | 2-pyridylmethyl | | x | x |
| 282 | 2-methoxy-1-napthylmethyl | | x | x |
| 283 | 9-[10-methyl]anthranylmethyl | x | x | |
| 284 | 9-anthranylmethyl | | x | x |
| 285 | 2-quinolylmethyl | | x | x |
| 286 | 5-nitro-1-naphthylmethyl | x | | x |
| 287 | 3,4 cyclohexenylmethyl | | x | x |
| 288 | 4-[2-t-butoxyethoxy]benzyl | x | x | |

The formula I compounds have in vitro and in vivo activity against Gram-positive pathogenic bacteria. The minimal inhibitory concentrations (MIC) at which the formula I compounds inhibit certain bacteria are given in Table 3. The MIC's were determined using a standard broth micro-dilution assay.

TABLE 3

In Vitro Activity of Formula I Compounds
MIC (mcg/ml)/Compound

| Organism | vancomycin | A82846A | A82846B | A82846C | 1 | 2 | 3 | 4 | 5 | 6 |
|---|---|---|---|---|---|---|---|---|---|---|
| Staphylococcus aureus 446 | 0.5 | 0.25 | 0.25 | 0.5 | ≦.06 | ≦.06 | ≦.06 | ≦.06 | 1 | 0.5 |
| Staphylococcus aureus 489 | 0.125 | 0.5 | ≦.06 | ≦.06 | ≦.06 | 0.25 | ≦.06 | 0.5 | 0.5 | 0.25 |
| Staphylococcus aureus 447 | 0.5 | 0.25 | 0.25 | 0.5 | ≦.06 | ≦.06 | ≦.06 | 0.25 | 0.5 | 0.5 |
| Staphylococcus aureus X400 | 0.5 | 0.125 | 0.125 | 0.25 | ≦.06 | 1 | ≦.06 | ≦.06 | 1 | 1 |
| Staphylococcus aureus X778 | 0.5 | 0.125 | 0.125 | 0.5 | 0.125 | ≦.06 | ≦.06 | ≦.06 | 0.5 | 0.25 |
| Staphylococcus aureus 491 | 1 | 0.25 | 0.25 | 0.1 | 2 | ≦.06 | 0.5 | ≦.06 | 0.5 | 0.125 |
| Staphylococcus aureus S13E | 0.5 | 0.125 | 0.125 | 0.25 | 0.125 | ≦.06 | ≦.06 | ≦.06 | 1 | 0.25 |
| Staphylococcus aureus SA1199 | 0.5 | 0.125 | 0.125 | 0.25 | ≦.06 | 0.5 | 0.125 | ≦.06 | 1 | 0.25 |
| Staphylococcus aureus SA1199A | 0.125 | ≦.06 | ≦.06 | 0.125 | ≦.06 | ≦.06 | ≦.06 | ≦.06 | ≦.06 | ≦.06 |
| Staphylococcus aureus SA1199B | 0.5 | ≦.06 | 0.125 | ≦.06 | | ≦.06 | ≦.06 | ≦.06 | ≦.06 | |
| Staphylococcus haemolyticus 105 | 16 | 0.5 | 1 | 1 | 4 | 2 | 4 | 0.5 | 2 | 0.5 |
| Staphylococcus haemolyticus 415 | 8 | 1 | 4 | 2 | 4 | 1 | 8 | 0.5 | 1 | 0.5 |
| Staphylococcus epidermidis 270 | 16 | 0.25 | 0.25 | 0.125 | 8 | 8 | 8 | ≦.06 | 0.25 | 0.125 |
| Entercoccus faecium 180 | >64 | 16 | 8 | 16 | 0.5 | 0.25 | 0.5 | 0.125 | ≦.06 | 0.125 |
| Entercoccus faecium 180-1 | 0.5 | 0.125 | 0.125 | 0.125 | ≦.06 | ≦.06 | ≦.06 | ≦.06 | ≦.06 | ≦.06 |
| Entercoccus faecalis 2041 | 2 | 0.125 | 0.25 | 0.5 | 0.125 | ≦.06 | ≦.06 | ≦.06 | ≦.06 | |
| Entercoccus faecalis 276 | 1 | 0.125 | 0.125 | 0.5 | ≦.06 | 0.5 | ≦.06 | ≦.06 | ≦.06 | ≦.06 |
| Entercoccus gallinarum 245 | 4 | 0.125 | 0.25 | 0.5 | 4 | ≦.06 | ≦.06 | ≦.06 | ≦.06 | ≦.06 |
| Haemophilus influenzae RD | >64 | >64 | >64 | >64 | >64 | | | | | >64 |
| Escherichia coli EC14 | >64 | >64 | >64 | >64 | >64 | >64 | >64 | >64 | >64 | >64 |
| Streptococcus pyogenes C203 | 0.5 | | | 0.125 | ≦.06 | ≦.06 | ≦.06 | ≦.06 | ≦.06 | ≦.06 |
| Streptococcus pneumoniae P1 | 0.25 | | | | ≦.06 | ≦.06 | ≦.06 | ≦.06 | ≦.06 | ≦.06 |

| Organism | 7 | 8 | 9 | 10 | 1 | 12 | 13 | 14 | 15 | 16 | 17 |
|---|---|---|---|---|---|---|---|---|---|---|---|
| Staphylococcus aureus 446 | 8 | 2 | 2 | 16 | 4 | 32 | 2 | 4 | 1 | 4 | 2 |
| Staphylococcus aureus 489 | 2 | 4 | 0.5 | >64 | 1 | 8 | 1 | 2 | ≦0.06 | 0.5 | 1 |
| Staphylococcus aureus 447 | 4 | 8 | 4 | >64 | 4 | 32 | 8 | 8 | 2 | 4 | 8 |
| Staphylococcus aureus X400 | 1 | 8 | 0.5 | >64 | 0.5 | 8 | 1 | 4 | 0.25 | 0.5 | 0.5 |

TABLE 3-continued

In Vitro Activity of Formula I Compounds
MIC (mcg/ml)/Compound

| Organism | | | | | | | | | | | |
|---|---|---|---|---|---|---|---|---|---|---|---|
| Staphylococcus aureus X778 | 0.25 | 8 | 0.25 | 16 | 0.25 | 8 | 2 | 4 | 0.25 | 2 | 0.5 |
| Staphylococcus aureus 491 | 2 | 4 | 0.5 | 16 | 1 | 4 | 2 | 1 | 0.25 | 1 | 2 |
| Staphylococcus aureus S13E | 2 | 8 | 0.5 | 8 | 0.5 | 8 | 0.25 | 4 | 0.5 | 1 | 1 |
| Staphylococcus aureus SA1199 | 4 | 2 | 0.25 | 8 | 2 | 8 | 0.5 | 8 | 0.25 | 2 | 4 |
| Staphylococcus aureus SA1199A | ≦0.06 | 2 | ≦0.06 | 4 | ≦0.06 | 8 | ≦0.06 | 0.5 | ≦0.06 | ≦0.06 | ≦0.06 |
| Staphylococcus aureus SA1199B | 1 | | 0.25 | 8 | 2 | | 4 | 8 | 0.25 | 1 | 1 |
| Staphylococcus haemolyticus 105 | 8 | 8 | 4 | >64 | 4 | 16 | 8 | 4 | 0.5 | 8 | 8 |
| Staphylococcus haemolyticus 415 | 16 | 8 | 4 | >64 | 2 | 32 | 1 | 8 | 2 | 4 | 8 |
| Staphylococcus epidermidis 270 | 4 | 4 | 16 | >64 | 2 | 0.125 | 8 | 4 | 1 | 2 | 4 |
| Entercoccus faecium 180 | 2 | 1 | 1 | 8 | 1 | 4 | 2 | 1 | 0.5 | 1 | 2 |
| Entercoccus faecium 180-1 | ≦0.06 | 0.5 | ≦0.06 | 4 | ≦0.06 | 4 | ≦0.06 | 1 | ≦0.06 | 0.125 | ≦0.06 |
| Entercoccus faecalis 2041 | 0.125 | 4 | 0.25 | 16 | 0.5 | 16 | 0.125 | 2 | ≦0.06 | 0.5 | 0.25 |
| Entercoccus faecalis 276 | 1 | 4 | 0.26 | 18 | 1 | 4 | 0.5 | 4 | ≦0.06 | 2 | 0.5 |
| Entercoccus gallinarum 245 | 0.5 | 8 | 0.25 | 8 | ≦0.06 | 32 | 0.25 | 0.25 | ≦0.06 | 1 | 0.5 |
| Haemophilus influenzae RD | 16 | >64 | ≦0.06 | | | 64 | 32 | | | | 32 |
| Escherichia coli EC14 | >64 | >6 | >64 | >64 | >64 | >64 | >64 | >64 | >64 | >64 | >64 |
| Streptococcus pyogenes C203 | ≦0.06 | ≦0.06 | ≦0.06 | 0.5 | ≦0.06 | 0.25 | ≦0.06 | ≦0.06 | ≦0.06 | ≦0.06 | ≦0.06 |
| Streptococcus pneumoniae P1 | ≦0.06 | ≦0.06 | ≦0.06 | 0.0125 | ≦0.06 | ≦0.06 | ≦0.06 | ≦0.06 | ≦0.06 | ≦0.06 | ≦0.06 |

| Organism | 18 | 19 | 20 | 21 | 22 | 23 | 24 | 25 | 26 | 27 | 28 |
|---|---|---|---|---|---|---|---|---|---|---|---|
| Staphylococcus aureus 446 | 2 | 0.5 | 0.5 | >64 | 16 | 38 | 0.5 | 0.5 | 0.25 | 2 | 0.25 |
| Staphylococcus aureus 489 | 1 | 0.25 | 0.5 | 32 | 8 | >64 | ≦0.06 | ≦0.06 | ≦0.06 | ≦0.06 | ≦0.06 |
| Staphylococcus aureus 447 | 8 | 1 | 4 | >64 | 16 | 16 | 1 | 0.25 | 2 | 8 | 1 |
| Staphylococcus aureus X400 | 1 | 0.25 | 0.5 | 32 | 8 | 16 | 0.22 | ≦0.06 | 0.25 | 0.5 | ≦0.06 |
| Staphylococcus aureus X778 | 0.5 | 0.25 | 0.25 | 32 | 8 | 16 | 0.125 | ≦0.06 | 0.125 | 0.5 | ≦0.06 |
| Staphylococcus aureus 491 | 2 | 2 | 1 | 64 | 8 | 16 | 0.5 | 0.125 | 0.5 | 1 | 0.25 |
| Staphylococcus aureus S13E | 1 | ≦0.06 | ≦0.06 | 64 | 16 | 16 | ≦0.06 | ≦0.06 | 0.25 | 0.125 | ≦0.06 |
| Staphylococcus aureus SA1199 | 2 | 0.5 | 2 | 64 | 16 | 16 | 0.5 | ≦0.06 | 1 | 0.5 | 0.125 |
| Staphylococcus aureus SA1199A | ≦0.06 | ≦0.06 | ≦0.06 | 16 | 4 | 16 | ≦0.06 | ≦0.06 | ≦0.06 | ≦0.06 | ≦0.06 |
| Staphylococcus aureus SA1199B | 2 | 1 | 0.5 | 64 | 16 | 16 | 2 | 0.125 | 0.5 | 1 | 0.125 |
| Staphylococcus haemolyticus 105 | 16 | 4 | 8 | >64 | 16 | 4 | 4 | 1 | 4 | 16 | 4 |
| Staphylococcus haemolyticus 415 | 8 | 8 | 4 | 64 | 16 | 16 | ≦0.06 | 32 | 8 | 8 | 8 |
| Staphylococcus epidermidis 270 | 8 | 2 | 2 | 32 | 4 | 64 | 1 | 0.5 | 1 | 4 | 1 |
| Entercoccus faecium 180 | 2 | 1 | 1 | 8 | 1 | >64 | 4 | 0.5 | 4 | 8 | 1 |
| Entercoccus faecium 180-1 | ≦0.06 | ≦0.06 | ≦0.06 | 8 | 1 | 32 | ≦0.06 | ≦0.06 | 0.25 | 0.5 | ≦0.06 |
| Entercoccus faecalis 2041 | 0.25 | ≦0.06 | ≦0.06 | 32 | 2 | 32 | ≦0.06 | 0.25 | 0.25 | 0.125 | 0.25 |
| Entercoccus faecalis 276 | 1 | ≦0.06 | 0.25 | 64 | 4 | 32 | 0.25 | 0.25 | ≦0.06 | 0.5 | ≦0.06 |
| Entercoccus gallinarum 245 | 1 | ≦0.06 | 0.25 | 8 | 1 | 8 | 0.25 | ≦0.06 | 0.125 | 0.5 | 0.25 |
| Haemophilus influenzae RD | 16 | 32 | 8 | >64 | 65 | >64 | >64 | 32 | >64 | >64 | >64 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | 2 | 1 | 1 | ≦0.06 | ≦0.06 | ≦0.06 | ≦0.06 | |
| Streptococcus pneumoniae P1 | ≦0.06 | ≦0.06 | ≦0.06 | 0.5 | 0.25 | 0.5 | ≦0.06 | ≦0.06 | ≦0.06 | ≦0.06 | |

| Organism | 29 | 30 | 31 | 32 | 33 | 34 | 35 | 36 | 37 | 38 | 39 |
|---|---|---|---|---|---|---|---|---|---|---|---|
| Staphylococcus aureus 446 | 1 | 1 | 0.5 | 1 | 4 | 32 | 0.5 | 8 | 0.5 | 0.5 | 0.125 |
| Staphylococcus aureus 489 | 1 | 0.125 | ≦0.06 | 1 | ≦0.06 | 8 | ≦0.06 | 2 | 0.125 | ≦0.06 | ≦0.06 |
| Staphylococcus aureus 447 | 0.25 | 2 0.5 | 0.5 | 0.125 | 8 | 0.125 | 2 | 0.125 | 0.125 | 0.25 | |
| Staphylococcus aureus X400 | 0.25 | ≦0.06 | 0.125 | 0.5 | 0.25 | 32 | 0.25 | 4 | 0.25 | 1 | ≦0.06 |
| Staphylococcus aureus X778 | ≦0.06 | ≦0.06 | 0.125 | 0.5 | 0.5 | 16 | ≦0.06 | 2 | ≦0.06 | 0.5 | ≦0.06 |
| Staphylococcus aureus 491 | 0.25 | 0.5 | 0.5 | 0.25 | 0.125 | 8 | 0.125 | 1 | 0.25 | 0.5 | 0.25 |
| Staphylococcus aureus S13E | 1 | 0.125 | 0.25 | 1 | ≦0.06 | 16 | ≦0.06 | 2 | ≦0.06 | ≦0.06 | ≦0.06 |
| Staphylococcus aureus SA1199 | 0.25 | 0.5 | 0.25 | 1 | 1 | 16 | 0.25 | 4 | 0.25 | 1 | ≦0.06 |
| Staphylococcus aureus SA1199A | ≦0.06 | ≦0.06 | ≦0.06 | ≦0.06 | ≦0.06 | 2 | ≦0.06 | ≦0.06 | ≦0.06 | ≦0.06 | ≦0.06 |
| Staphylococcus aureus SA1199B | 0.25 | 0.125 | 0.25 | 0.125 | 0.125 | 16 | 0.25 | 4 | ≦0.06 | 0.125 | ≦0.06 |
| Staphylococcus haemolyticus 105 | 4 | 4 | 4 4 | 2 | 32 | 2 | 4 | 0.25 | 1 | 2 | |
| Staphylococcus haemolyticus 415 | 1 | 16 | 1 | 6 4 | 8 | >64 | 4 | 8 | 1 | 1 | 4 |
| Staphylococcus epidermidis 270 | 0.5 | 2 | 1 | 1 | 2 16 | 1 | 2 | 0.25 | 0.5 | 0.25 | |
| Entercoccus faecium 180 | 0.25 | 2 | 4 0.25 | 2 4 | 1 | 0.25 | 0.125 | ≦0.06 | 0.5 | | |
| Entercoccus faecium 180-1 | ≦0.06 | ≦0.06 | ≦0.06 | ≦0.06 | ≦0.06 | 2 | ≦0.06 | ≦0.06 | ≦0.06 | ≦0.06 | ≦0.06 |
| Entercoccus faecalis 2041 | 0.25 | ≦0.06 | 0.25 | 0.25 | ≦0.06 | 8 | ≦0.06 | 1 | 0.125 | ≦0.06 | ≦0.06 |
| Entercoccus faecalis 276 | 0.25 | 0.25 | 0.25 | 0.125 | ≦0.06 | 16 | ≦0.06 | 2 | 1 | 0.5 | ≦0.06 |
| Entercoccus gallinarum 245 | 0.25 | ≦0.06 | 0.25 | 0.25 | 0.25 | 4 | ≦0.06 | 0.25 | 0.125 | 0.125 | ≦0.06 |
| Haemophilus influenzae RD | 64 | >64 | >64 | >64 | | | | | >64 | >64 | |
| Escherichia coli EC14 | 64 | >64 | >64 | 32 >64 | >64 | >64 | >64 | >64 | >64 | >64 | |
| Streptococcus pyogenes C203 | | | | | | | | | ≦0.06 | ≦0.06 | ≦0.06 |
| Streptococcus pneumoniae P1 | | | | | | | | | ≦0.06 | ≦0.06 | ≦0.06 |

| Organism | 40 | 41 | 42 | 43 | 44 | 45 | 46 | 47 | 48 | 49 | 50 |
|---|---|---|---|---|---|---|---|---|---|---|---|
| Staphylococcus aureus 446 | 4 | 2 | 1 | 0.5 | 0.25 | 1 | 1 | 0.125 | 0.125 | 0.5 | 0.5 |
| Staphylococcus aureus 489 | 4 | ≦0.06 | 0.5 | ≦0.06 | ≦0.06 | 0.5 | 1 | ≦0.06 | ≦0.06 | ≦0.06 | ≦0.06 |
| Staphylococcus aureus 447 | 2 | 0.25 | 0.5 | 2 | 1 | 16 | 2 | 2 | 2 | 1 | 0.5 |
| Staphylococcus aureus X400 | 4 | ≦0.06 | 1 | 0.25 | ≦0.06 | 0.25 | 2 | ≦0.06 | ≦0.06 | 0.125 | 0.125 |
| Staphylococcus aureus X778 | 4 | 0.125 | 1 | ≦0.06 | ≦0.06 | 0.25 | 2 | ≦0.06 | ≦0.06 | ≦0.06 | 0.125 |

TABLE 3-continued

In Vitro Activity of Formula I Compounds
MIC (mcg/ml)/Compound

| Organism | | | | | | | | | | | |
|---|---|---|---|---|---|---|---|---|---|---|---|
| Staphylococcus aureus 491 | 4 | 0.5 | 0.5 | 1 | 0.125 | 1 | 2 | 0.5 | 0.25 | 0.125 | 0.5 |
| Staphylococcus aureus S13E | 4 | ≦0.06 | 0.5 | 0.25 | 0.25 | 0.5 | 2 | ≦0.06 | ≦0.06 | ≦0.06 | 0.125 |
| Staphylococcus aureus SA1199 | 4 | ≦0.06 | 1 | 0.5 | 0.25 | 2 | 2 | 0.5 | 0.25 | 2 | 1 |
| Staphylococcus aureus SA1199A | 0.5 | ≦0.06 | ≦0.06 | ≦0.06 | ≦0.06 | ≦0.06 | 0.5 | 0.25 | ≦0.06 | ≦0.06 | ≦0.06 |
| Staphylococcus aureus SA1199B | 8 | 0.25 | 2 | 0.5 | 0.25 | 1 | 2 | 0.25 | 1 | 1 | 2 |
| Staphylococcus haemolyticus 105 | 2 | 2 | 2 | 4 | 2 | 16 | 2 | 4 | 2 | 1 | 0.5 |
| Staphylococcus haemolyticus 415 | 2 | 4 | 1 | 8 | 4 | 8 | 2 | 16 | 8 | 1 | 1 |
| Staphylococcus epidermidis 270 | 1 | 0.25 | 0.5 | 2 | 0.5 | 8 | 2 | 1 | 1 | 1 | 0.5 |
| Entercoccus faecium 180 | 1 | 0.25 | 0.25 | 4 | 8 | 1 | 0.5 | 2 | 1 | 0.25 | 0.25 |
| Entercoccus faecium 180-1 | 2 | ≦0.06 | ≦0.06 | ≦0.06 | ≦0.06 | ≦0.06 | ≦0.06 | ≦0.06 | ≦0.06 | ≦0.06 | ≦0.06 |
| Entercoccus faecalis 2041 | 1 | ≦0.06 | 0.125 | 0.5 | ≦0.06 | 0.125 | 1 | ≦0.06 | ≦0.06 | ≦0.06 | ≦0.06 |
| Entercoccus faecalis 276 | 2 | ≦0.06 | 8 | 0.5 | 0.125 | 0.25 | 0.5 | ≦0.06 | ≦0.06 | 0.25 | 0.25 |
| Entercoccus gallinarum 245 | 11 | ≦0.06 | 1 | 0.5 | 0.5 | 0.5 | 0.25 | 16 | 1 | 1 | 1 |
| Haemophilus influenzae RD | | | | | >64 | >64 | >64 | >64 | >64 | >64 | >64 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | | | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | | ≦0.06 | ≦0.06 | ≦0.06 | ≦0.06 | ≦0.06 | ≦0.06 |

| Organism | 51 | 52 | 53 | 54 | 55 | 56 | 57 | 58 | 59 | 60 | 61 |
|---|---|---|---|---|---|---|---|---|---|---|---|
| Staphylococcus aureus 446 | 0.25 | ≦0.06 | 2 | 1 | 0.5 | 0.5 | 0.25 | 0.25 | 0.5 | 1 | 0.5 |
| Staphylococcus aureus 489 | ≦0.06 | 0.5 | 2 | ≦0.06 | 1 | 1 | 0.5 | ≦0.06 | 0.125 | 0.5 | 1 |
| Staphylococcus aureus 447 | 0.5 | ≦0.06 | 4 | 0.25 | 4 | 2 | 0.5 | 1 | 1 | 2 | 2 |
| Staphylococcus aureus X400 | ≦0.06 | ≦0.06 | 4 | ≦0.06 | ≦0.06 | ≦0.06 | 0.125 | ≦0.06 | 0.25 | 0.5 | ≦0.06 |
| Staphylococcus aureus X778 | 0.5 | 0.5 | 2 | ≦0.06 | 0.5 | 0.125 | ≦0.06 | ≦0.06 | ≦0.06 | 0.25 | 0.125 |
| Staphylococcus aureus 491 | 0.25 | | 2 | | 0.5 | 0.5 | | 0.125 | | 1 | 0.5 |
| Staphylococcus aureus S13E | 0.5 | 0.5 | 2 | 0.5 | 0.5 | 0.125 | ≦0.06 | ≦0.06 | 0.125 | 0.25 | 0.125 |
| Staphylococcus aureus SA1199 | 0.5 | 2 2 | 0.5 | 0.5 | 0.5 | 1 | 1 | ≦0.06 | 0.5 | 0.25 | |
| Staphylococcus aureus SA1199A | ≦0.06 | ≦0.06 | 1 | ≦0.06 | ≦0.06 | ≦0.06 | ≦0.06 | ≦0.06 | ≦0.06 | ≦0.06 | ≦0.06 |
| Staphylococcus aureus SA1199B | 1 | 2 2 | 1 | 0.5 | 0.5 | 0.125 | 0.125 | 0.5 | 0.5 | 0.25 | |
| Staphylococcus haemolyticus 105 | 0.5 | 0.5 | 2 | 2 | 4 | 4 | 8 | 4 | 8 | >64 | 64 |
| Staphylococcus haemolyticus 415 | 1 | 1 | 2 | 1 | 1 | 6 16 | 1 | 8 | 8 | 16 | 8 |
| Staphylococcus epidermidis 270 | 0.5 | 0.5 | 2 | 0.25 | 1 | 1 | 0.5 | 4 | 1 | 2 | 1 |
| Entercoccus faecium 180 | 0.5 | 2 | 1 | 1 | 2 | 2 | 0.5 | 8 | 8 | 4 | 2 |
| Entercoccus faecium 180-1 | ≦0.06 | ≦0.06 | 2 | ≦0.06 | ≦0.06 | ≦0.06 | ≦0.06 | 0.25 | ≦0.06 | ≦0.06 | ≦0.06 |
| Entercoccus faecalis 2041 | ≦0.06 | 0.5 | 1 | ≦0.06 | 0.125 | 0.25 | ≦0.06 | 0.5 | 0.5 | 0.25 | ≦0.06 |
| Entercoccus faecalis 276 | ≦0.06 | 0.125 | 8 | 1 | 0.5 | 0.25 | 0.5 | 0.5 | 0.125 | 0.5 | 0.25 |
| Entercoccus gallinarum 245 | 1 | 1 | 2 | 0.5 | 16 | 16 | 2 | 0.5 | 1 | 16 | 8 |
| Haemophilus influenzae RD | >64 | >64 | >64 | | >64 | >64 | >64 | >64 | >64 | >64 | >64 |
| Escherichia coli EC14 | >64 | >64 | >64 | >64 | >64 | >64 | >64 | >64 | >64 | >64 | >64 |
| Streptococcus pyogenes C203 | | ≦0.06 | ≦0.06 | ≦0.06 | ≦0.06 | ≦0.06 | ≦0.06 | ≦0.06 | ≦0.06 | | |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |

| Organism | 62 | 63 | 64 | 65 | 66 | 67 | 68 | 69 | 70 | 71 | 72 |
|---|---|---|---|---|---|---|---|---|---|---|---|
| Staphylococcus aureus 446 | 2 | 0.5 | 0.25 | 2 | 0.25 | 0.25 | 0.125 | 1 | 0.125 | 4 | 2 |
| Staphylococcus aureus 489 | 2 | 8 | 0.25 | 0.125 | 1 | ≦0.06 | 0.125 | 0.25 | ≦0.06 | 0.25 | ≦0.06 |
| Staphylococcus aureus 447 | 0.5 | 1 | 0.5 | 1 | 1 | 1 | 0.25 | 1 | 0.5 | 4 | 1 |
| Staphylococcus aureus X400 | ≦0.06 | ≦0.06 | 0.125 | 0.125 | 0.125 | 1 | ≦0.06 | 0.5 | ≦0.06 | 1 | 0.125 |
| Staphylococcus aureus X778 | 0.5 | 0.125 | 2 | 0.5 | ≦0.06 | 0.25 | ≦0.06 | 0.125 | ≦0.06 | 2 | 0.25 |
| Staphylococcus aureus 491 | 0.125 | 0.5 | 0.125 | 0.5 | 0.25 | 1 | 0.125 | 1 | 0.5 | 2 | 0.25 |
| Staphylococcus aureus S13E | 0.5 | 0.125 | 2 | 0.5 | ≦0.06 | 0.25 | ≦0.06 | 0.25 | ≦0.06 | 1 | ≦0.06 |
| Staphylococcus aureus SA1199 | 0.25 | 0.25 | 1 | 0.5 | 0.25 | 1 | ≦0.06 | 1 | ≦0.06 | 1 | 1 |
| Staphylococcus aureus SA1199A | ≦0.06 | 0.125 | ≦0.06 | ≦0.06 | ≦0.06 | ≦0.06 | ≦0.06 | ≦0.06 | ≦0.06 | 0.25 | ≦0.06 |
| Staphylococcus aureus SA1199B | 1 | 0.5 | 0.125 | 2 | 0.25 | 1 | 0.5 | 2 | ≦0.06 | 4 | ≦0.06 |
| Staphylococcus haemolyticus 105 | 2 | 4 | 64 | 64 | 64 | 64 | 2 | 4 | 2 | 16 | 1 |
| Staphylococcus haemolyticus 415 | 4 | 8 | 2 | 4 | 8 | 2 | 4 | 8 | 2 | 8 | 4 |
| Staphylococcus epidermidis 270 | 1 | 1 | 0.5 | 1 | 1 | 0.5 | 2 | 2 | 0.25 | 2 | 0.25 |
| Entercoccus faecium 180 | 4 | 16 | 0.125 | 0.5 | 2 | 0.25 | 2 | 4 | 0.5 | 4 | 0.5 |
| Entercoccus faecium 180-1 | ≦0.06 | ≦0.06 | ≦0.06 | ≦0.06 | ≦0.06 | ≦0.06 | ≦0.06 | ≦0.06 | ≦0.06 | 0.25 | ≦0.06 |
| Entercoccus faecalis 2041 | ≦0.06 | 0.25 | ≦0.06 | ≦0.06 | ≦0.06 | ≦0.06 | ≦0.06 | 0.25 | ≦0.06 | 1 | ≦0.06 |
| Entercoccus faecalis 276 | 0.5 | 0.5 | 0.5 | 0.5 | ≦0.06 | ≦0.06 | ≦0.06 | 0.5 | ≦0.06 | 2 | ≦0.06 |
| Entercoccus gallinarum 245 | 4 | 8 | 2 | 4 | 8 | 2 | 4 | 8 | 2 | 8 | 4 |
| Haemophilus influenzae RD | >64 | >64 | >64 | >64 | >64 | >64 | >64 | >64 | 16 | >64 | 32 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | | | | | | | | | |
| Streptococcus pneumoniae P1 | ≦0.06 | ≦0.06 | ≦0.06 | ≦0.06 | ≦0.06 | ≦0.06 | | | | | |

| Organism | 73 | 74 | 75 | 76 | 77 | 78 | 79 | 80 | 81 | 82 | 83 |
|---|---|---|---|---|---|---|---|---|---|---|---|
| Staphylococcus aureus 446 | 0.25 | 4 | 2 | 0.25 | ≦0.06 | 2 | 2 | 4 | 2 | 2 | 1 |
| Staphylococcus aureus 489 | 0.25 | ≦0.06 | ≦0.06 | ≦0.06 | ≦0.06 | ≦0.06 | 2 | 2 | 2 | 0.25 | 0.25 |
| Staphylococcus aureus 447 | 0.25 | 1 | 1 | 0.05 | 1 | ≦0.06 | 2 | 2 | 2 | 4 | 2 |
| Staphylococcus aureus X400 | 0.5 | ≦0.06 | ≦0.06 | 0.25 | ≦0.06 | ≦0.06 | 0.25 | 4 | 1 | 0.25 | 2 |
| Staphylococcus aureus X778 | 1 | ≦0.06 | ≦0.06 | 0.25 | ≦0.06 | ≦0.06 | 2 | 0.5 | 1 | 0.5 | 0.5 |
| Staphylococcus aureus 491 | 0.25 | 0.125 | 0.25 | 0.25 | | | 0.25 | 4 | 1 | 1 | 0.5 |

TABLE 3-continued

In Vitro Activity of Formula I Compounds
MIC (mcg/ml)/Compound

| Organism | | | | | | | | | | | |
|---|---|---|---|---|---|---|---|---|---|---|---|
| Staphylococcus aureus S13E | | 0 | 0 | | 0.125 | | 4 | 1 | 0.5 | ≦0.06 | 0.125 |
| Staphylococcus aureus SA1199 | 0.5 | ≦0.06 | 2 | ≦0.06 | ≦0.06 | 0.125 | 1 | 2 | 2 | 0.25 | 2 |
| Staphylococcus aureus SA1199A | 0.25 | ≦0.06 | ≦0.06 | 0.125 | ≦0.06 | ≦0.06 | 0.125 | 1 | 0.5 | 0.5 | 0.25 |
| Staphylococcus aureus SA1199B | ≦0.06 | 1 | 0.5 | 0.25 | 0.125 | ≦0.06 | 1 | 1 | 1 | 1 | 1 |
| Staphylococcus haemolyticus 105 | 0.5 | 4 | 2 | 2 | 2 | 2 | 4 | 4 | 1 | 8 | 2 |
| Staphylococcus haemolyticus 415 | 2 4 | 4 | 4 | 8 | 16 | 4 | 4 | 4 | 8 | 4 | |
| Staphylococcus epidermidis 270 | 0.125 | 0.5 | 0.5 | 0.25 | 0.5 | 0.5 | 0.5 | 1 | 1 | 4 | 2 |
| Enterococcus faecium 180 | 0.5 | 0.5 | 0.5 | 0.5 | 8 | 1 | ≦0.06 | 0.125 | ≦0.06 | 2 | 8 |
| Enterococcus faecium 180-1 | ≦0.06 | ≦0.06 | ≦0.06 | ≦0.06 | 0.125 | ≦0.06 | ≦0.06 | ≦0.06 | 0.125 | 0.125 | 0.125 |
| Enterococcus faecalis 2041 | 0.125 | ≦0.06 | ≦0.06 | ≦0.06 | 0.25 | ≦0.06 | ≦0.06 | ≦0.06 | ≦0.06 | 0.5 | 0.5 |
| Enterococcus faecalis 276 | 0.25 | | ≦0.06 | ≦0.06 | 0.25 | 0.125 | ≦0.06 | ≦0.06 | ≦0.06 | ≦0.06 | |
| Enterococcus gallinarum 245 | 2 | ≦0.06 | 4 | 4 | 0.25 | 0.125 | ≦0.06 | 0.25 | 0.125 | 2 | 0.5 |
| Haemophilus influenzae RD | 0.25 | 0.5 | 2 | >64 | 64 | | 16 | 16 | 16 | 64 | >64 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |

| Organism | 84 | 85 | 86 | 87 | 88 | 89 | 90 | 91 | 92 | 93 | 94 |
|---|---|---|---|---|---|---|---|---|---|---|---|
| Staphylococcus aureus 446 | 0.5 | 0.125 | 1 | 1 | 0.25 | 0.5 | 2 | 0.5 | 2 | 2 | 1 |
| Staphylococcus aureus 489 | ≦0.06 | 0.25 | 1 | 0.5 | 0.5 | 0.25 | 2 | ≦0.06 | ≦0.06 | 0.25 | 2 |
| Staphylococcus aureus 447 | 4 | 0.125 | 0.5 | 0.5 | 0.25 | 1 | 1 | 0.5 | 0.5 | 0.25 | 0.5 |
| Staphylococcus aureus X400 | ≦0.06 | 0.25 | 1 | 1 | ≦0.06 | 0.25 | 1 | 0.5 | 0.5 | ≦0.06 | 1 |
| Staphylococcus aureus X778 | ≦0.06 | 0.25 | 1 | 2 | 0.5 | 0.25 | 1 | ≦0.06 | 0.25 | 1 | 0.5 |
| Staphylococcus aureus 491 | 1 | 0.125 | 1 | 2 | 0.5 | 1 | 2 | 1 | 1 | 0.25 | 0.5 |
| Staphylococcus aureus S13E | 0.125 | 0.5 | 1 | 0.5 | 1 | 0.25 | 1 | ≦0.06 | 0.125 | 1 | 2 |
| Staphylococcus aureus SA1199 | 0.25 | 0.5 | 0.5 | 2 1 | 0.5 | 2 | ≦0.06 | 1 | 2 | 0.5 | |
| Staphylococcus aureus SA1199A | ≦0.06 | ≦0.06 | ≦0.06 | ≦0.06 | ≦0.06 | ≦0.06 | 0.5 | ≦0.06 | ≦0.06 | ≦0.06 | ≦0.06 |
| Staphylococcus aureus SA1199B | 0.5 | 1 | 1 | 1 | 0.5 | 1 | 1 | 0.5 | 0.5 | 1 | 2 |
| Staphylococcus haemolyticus 105 | 8 | 1 | 1 | 1 | 1 | 1 | 2 | 2 | 2 | 1 | 2 |
| Staphylococcus haemolyticus 415 | 16 | 2 1 | 2 2 2 | 2 | 2 | 2 | 2 | 1 | 2 | | |
| Staphylococcus epidermidis 270 | 1 | 0.5 | 1 | 1 | 1 | 1 | 1 | 0.5 | 1 | 1 | 1 |
| Enterococcus faecium 180 | 4 | ≦0.06 | ≦0.06 | ≦0.06 | 0.125 | ≦0.06 | 0.25 | 0.5 | 0.125 | ≦0.06 | 0.25 |
| Enterococcus faecium 180-1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Enterococcus faecalis 2041 | ≦0.06 | ≦0.06 | ≦0.06 | ≦0.06 | ≦0.06 | ≦0.06 | 0.125 | ≦0.06 | 0.125 | ≦0.06 | ≦0.06 |
| Enterococcus faecalis 276 | | 0.125 | ≦0.06 | ≦0.06 | ≦0.06 | ≦0.06 | 2 | ≦0.06 | 0.125 | 0.25 | 0.125 |
| Enterococcus gallinarum 245 | 0.25 | 2 1 | 2 ≦0.06 | ≦0.06 | 2 | 2 | 2 1 | 2 | | | |
| Haemophilus influenzae RD | | | | | | | >64 | | | | |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |

| Organism | 95 | 96 | 97 | 98 | 99 | 100 | 101 | 102 | 103 | 104 | 105 |
|---|---|---|---|---|---|---|---|---|---|---|---|
| Staphylococcus aureus 446 | 0.5 | 1 | 1 | 0.5 | 0.5 | 1 | 0.5 | 1 | 0.5 | ≦0.06 | 0.25 |
| Staphylococcus aureus 489 | 2 | 1 | 0.25 | ≦0.06 | 0.25 | 0.5 | ≦0.06 | ≦0.06 | ≦0.06 | ≦0.06 | 0.5 |
| Staphylococcus aureus 447 | 0.5 | 1 | 1 | 0.25 | 2 | 0.5 | 1 | 1 | 1 | 0.25 | 0.5 |
| Staphylococcus aureus X400 | 1 | 2 | 1 | ≦0.06 | 0.125 | 1 | ≦0.06 | ≦0.06 | ≦0.06 | ≦0.06 | 0.5 |
| Staphylococcus aureus X778 | 1 | 1 | 0.25 | ≦0.06 | 0.5 | 1 | 0.25 | ≦0.06 | 0.5 | ≦0.06 | 0.5 |
| Staphylococcus aureus 491 | 1 | 1 | 0.5 | 0.25 | 1 | ≦0.06 | 0.5 | 1 | 1 | ≦0.06 | 0.25 |
| Staphylococcus aureus S13E | 2 | 1 | >64 | 0.5 | 0.5 | 1 | 0.25 | 1 | 1 | ≦0.06 | 0.5 |
| Staphylococcus aureus SA1199 | 0.5 | 2 | 2 | 0.5 | 0.5 | 0.5 | 0.25 | 0.125 | 1 | 2 | 1 |
| Staphylococcus aureus SA1199A | ≦0.06 | ≦0.06 | ≦0.06 | ≦0.06 | 0.5 | 0.125 | 0.5 | ≦0.06 | ≦0.06 | ≦0.06 | 0.25 |
| Staphylococcus aureus SA1199B | 1 | 1 | 1 | 1 | 0.5 | 0.5 | 1 | 1 | 2 | 0.125 | 0.5 |
| Staphylococcus haemolyticus 105 | 1 | 2 | 2 | 1 | 8 | 1 | 1 | 2 | 4 | 2 | 1 |
| Staphylococcus haemolyticus 415 | 1 | 2 | 2 | 1 | 32 | 2 | 8 | 4 | 8 | 2 | 1 |
| Staphylococcus epidermidis 270 | 1 | 2 | 1 | ≦0.06 | 1 | 0.5 | 0.5 | 1 | 1 | 0.25 | 0.25 |
| Enterococcus faecium 180 | 0.5 | 0.5 | | | | | | | | ≦0.06 | 0.25 |
| Enterococcus faecium 180-1 | ≦0.06 | 0.25 | ≦0.06 | ≦0.06 | ≦0.06 | ≦0.06 | ≦0.06 | ≦0.06 | ≦0.06 | ≦0.06 | ≦0.06 |
| Enterococcus faecalis 2041 | ≦0.06 | 1 | ≦0.06 | ≦0.06 | 0.25 | ≦0.06 | ≦0.06 | ≦0.06 | ≦0.06 | ≦0.06 | 0.25 |
| Enterococcus faecalis 276 | 0.125 | 0.5 | ≦0.06 | 0.125 | 0.25 | 0.25 | 0.125 | 0.25 | 0.25 | ≦0.06 | 0.25 |
| Enterococcus gallinarum 245 | 1 | 2 | 2 | 1 | 32 | 2 | 8 | 4 | 8 | 2 | 1 |
| Haemophilus influenzae RD | | | | | >64 | >64 | >64 | | | 32 | >64 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | 0.125 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | 0.25 | ≦0.06 | ≦0.06 | ≦0.06 | ≦0.06 | ≦0.06 | ≦0.06 |

| Organism | 106 | 107 | 108 | 109 | 110 | 111 | 112 | 113 | 114 | 115 | 116 |
|---|---|---|---|---|---|---|---|---|---|---|---|
| Staphylococcus aureus 446 | 2 | 2 | 2 | 1 | 0.5 | 2 | 2 | ≦0.06 | 0.5 | 0.125 | 0.5 |
| Staphylococcus aureus 489 | 2 | 1 | 0.25 | ≦0.06 | 1 | 1 | 0.25 | 0.125 | 1 | 0.125 | 1 |
| Staphylococcus aureus 447 | 0.25 | 1 | 0.5 | 1 | 1 | 1 | 1 | 0.25 | 0.5 | 0.5 | 1 |
| Staphylococcus aureus X400 | 1 | 1 | 2 | ≦0.06 | 1 | 1 | 1 | 0.125 | 2 | 1 | 1 |
| Staphylococcus aureus X778 | 1 | 0.5 | 0.125 | ≦0.06 | 0.5 | 2 | 1 | 1 | 2 | 1 | 2 |
| Staphylococcus aureus 491 | 0.5 | 1 | 0.25 | 0.25 | 0.25 | 2 | 1 | 0.25 | 1 | 0.5 | 0.5 |
| Staphylococcus aureus S13E | 1 | 2 | 1 | 0.25 | 1 | 1 | 1 | ≦0.06 | 2 | 0.25 | 1 |

TABLE 3-continued

In Vitro Activity of Formula I Compounds
MIC (mcg/ml)/Compound

| Organism | | | | | | | | | | |
|---|---|---|---|---|---|---|---|---|---|---|
| Staphylococcus aureus SA1199 | 1 | 1 | 2 | ≦0.06 | 0.25 | 2 | 2 | 1 | 2 | 0.125 | 4 |
| Staphylococcus aureus SA1199A | ≦0.06 | ≦0.06 | ≦0.06 | ≦0.06 | ≦0.06 | 0.5 | 0.125 | ≦0.06 | ≦0.06 | ≦0.06 | ≦0.06 |
| Staphylococcus aureus SA1199B | 2 | 2 | 2 | 0.5 | 0.5 | 1 | 0.5 | ≦0.06 | 1 | 0.25 | 0.5 |
| Staphylococcus haemolyticus 105 | 1 | 2 | 2 | 1 | 4 | 1 | 2 | 4 | 2 | 1 | 2 |
| Staphylococcus haemolyticus 415 | 1 | 2 | 1 | 4 2 | 4 | 2 | 1 | 2 | 2 | 4 | |
| Staphylococcus epidermidis 270 | 0.25 | 0.5 | 0.125 | 0.25 | 2 | 1 | 1 | 0.25 | 1 | 0.5 | 1 |
| Entercoccus faecium 180 | ≦0.06 | 0.125 | 0.125 | 0.25 | 0.25 | ≦0.06 | ≦0.06 | ≦0.06 | ≦0.06 | 1 | ≦0.06 |
| Entercoccus faecium 180-1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Entercoccus faecalis 2041 | 0.125 | 0.5 | ≦0.06 | ≦0.06 | ≦0.06 | ≦0.06 | ≦0.06 | ≦0.06 | 0.25 | ≦0.06 | ≦0.06 |
| Entercoccus faecalis 276 | 0.5 | 1 | 0.5 | ≦0.06 | 0.5 | 0.5 | 0.5 | 0.25 | 1 | 0.125 | 0.25 |
| Entercoccus gallinarum 245 | 1 | 2 | ≦0.06 | ≦0.06 | 2 | 4 | 2 1 | 2 | 2 | 4 | |
| Haemophilus influenzae RD | >64 | >64 | >64 | 32 >64 | >64 | >64 | >64 | >64 | >64 | >64 | |
| Escherichia coli EC14 | >64 | >64 | >64 | | >64 | >64 | >64 | >64 | >64 | >64 | >64 |
| Streptococcus pyogenes C203 | ≦0.06 | ≦0.06 | ≦0.06 | | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | | ≦0.06 | ≦0.06 | ≦0.06 | ≦0.06 | ≦0.06 | ≦0.06 | ≦0.06 |

| Organism | 117 | 118 | 119 | 120 | 121 | 122 | 123 | 124 | 125 | 126 | 127 |
|---|---|---|---|---|---|---|---|---|---|---|---|
| Staphylococcus aureus 446 | 0.5 | 1 | 2 | 2 | 2 | 1 | 2 | 4 | 4 | 2 | 1 |
| Staphylococcus aureus 489 | 0.125 | 0.25 | 0.5 | 2 | 1 | ≦0.06 | 2 | 0.25 | 2 | 0.25 | 2 |
| Staphylococcus aureus 447 | 0.5 | 0.25 | 2 | 1 | 0.5 | 0.25 | 1 | 0.25 | 2 | 1 | 2 |
| Staphylococcus aureus X400 | ≦0.06 | 0.25 | 1 | 0.25 | 0.125 | ≦0.06 | 1 | 1 | 1 | 1 | 2 |
| Staphylococcus aureus X778 | 0.25 | 0.5 | 2 | 0.125 | 0.5 | ≦0.06 | 1 | 0.5 | 2 | 0.5 | 1 |
| Staphylococcus aureus 491 | 0.5 | ≦0.06 | ≦0.06 | ≦0.06 | ≦0.06 | ≦0.06 | ≦0.06 | 0.125 | 1 | 0.25 | 1 |
| Staphylococcus aureus S13E | ≦0.06 | 0.25 | 0.25 | ≦0.06 | ≦0.06 | ≦0.06 | ≦0.06 | ≦0.06 | 1 | 0.5 | 2 |
| Staphylococcus aureus SA1199 | ≦0.06 | 2 | 2 | 1 | 1 | ≦0.06 | 2 | 1 | 0.5 | 0.125 | 2 |
| Staphylococcus aureus SA1199A | ≦0.06 | ≦0.06 | 0.25 | ≦0.06 | ≦0.06 | ≦0.06 | 0.125 | ≦0.06 | 0.25 | 0.25 | 0.25 |
| Staphylococcus aureus SA1199B | 0.5 | ≦0.06 | 0.5 | 0.125 | 0.25 | ≦0.06 | 0.5 | ≦0.06 | 2 | 1 | 2 |
| Staphylococcus haemolyticus 105 | 1 | 1 | 2 | 2 | 2 | 1 | 2 | 2 | 4 | 0.5 | 2 |
| Staphylococcus haemolyticus 415 | 2 | 1 | 2 | 2 | 2 | 1 | 1 | 1 | 2 | 2 | 4 |
| Staphylococcus epidermidis 270 | 0.5 | 1 | 2 | 2 | 1 | ≦0.06 | 1 | 0.25 | 1 | 1 | ≦0.06 |
| Entercoccus faecium 180 | 1 | 0.125 | 0.125 | ≦0.06 | ≦0.06 | ≦0.06 | 0.25 | ≦0.06 | 1 | 1 | ≦0.06 |
| Entercoccus faecium 180-1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Entercoccus faecalis 2041 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Entercoccus faecalis 276 | 0.25 | ≦0.06 | 0.125 | ≦0.06 | ≦0.06 | ≦0.06 | 0.25 | ≦0.06 | 2 | 1 | ≦0.06 |
| Entercoccus gallinarum 245 | 2 | 1 | 2 | 2 | 2 | 1 | 1 | 1 | 12 | 2 | 4 |
| Haemophilus influenzae RD | | 16 | 16 | 16 | 16 | 16 | 16 | 16 | 16 | | >64 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |

| Organism | 128 | 129 | 130 | 131 | 132 | 133 | 134 | 135 | 136 | 137 | 138 |
|---|---|---|---|---|---|---|---|---|---|---|---|
| Staphylococcus aureus 446 | 4 | 2 | 1 | 2 | 1 | 2 | 2 | 1 | ≦0.06 | 0.25 | 0.125 |
| Staphylococcus aureus 489 | 1 | ≦0.06 | 0.5 | 1 | 1 | 1 | 0.5 | 0.125 | ≦0.06 | ≦0.06 | ≦0.06 |
| Staphylococcus aureus 447 | 1 | 1 | 1 | 1 | 2 | 1 | 1 | 1 | 2 | 4 | 2 |
| Staphylococcus aureus X400 | 1 | 0.25 | 0.5 | 1 | 1 | 0.5 | 0.25 | ≦0.06 | ≦0.06 | ≦0.06 | ≦0.06 |
| Staphylococcus aureus X778 | 1 | 0.25 | 1 | 0.5 | 2 | 2 | 1 | 1 | ≦0.06 | ≦0.06 | 0.25 |
| Staphylococcus aureus 491 | 2 | 0.5 | 0.5 | 0.125 | 0.5 | 0.25 | 0.5 | 0.25 | 0.25 | 0.25 | 0.125 |
| Staphylococcus aureus S13E | 1 | 0.25 | 0.5 | 1 | 2 | 1 | 2 | 1 | ≦0.06 | ≦0.06 | ≦0.06 |
| Staphylococcus aureus SA1199 | 0.5 | 0.25 | 1 | 0.25 | 1 | 0.25 | 0.25 | 1 | ≦0.06 | ≦0.06 | ≦0.06 |
| Staphylococcus aureus SA1199A | 0.5 | ≦0.06 | ≦0.06 | ≦0.06 | 0.25 | 0.25 | 0.25 | ≦0.06 | ≦0.06 | ≦0.06 | ≦0.06 |
| Staphylococcus aureus SA1199B | 2 | 0.25 | 2 | 1 | 2 | 2 | 2 | 0.25 | ≦0.06 | ≦0.06 | 0.5 |
| Staphylococcus haemolyticus 105 | 1 | 4 | 1 | 1 | 1 | 2 | 2 | 0.5 | 2 | 2 | 4 |
| Staphylococcus haemolyticus 415 | 2 4 | 2 | 2 | 2 | 2 | 4 | 2 | 4 | 8 | 8 | |
| Staphylococcus epidermidis 270 | 1 | 1 | 1 | 1 | 2 | 1 | 2 | 0.5 | 1 | 0.5 | 2 |
| Entercoccus faecium 180 | 1 | 4 | 1 | ≦0.06 | 0.25 | 1 | 0.5 | 1 | 2 | 0.125 | 4 |
| Entercoccus faecium 180-1 | 0.125 | ≦0.06 | ≦0.06 | ≦0.06 | ≦0.06 | ≦0.06 | ≦0.06 | ≦0.06 | ≦0.06 | ≦0.06 | ≦0.06 |
| Entercoccus faecalis 2041 | 0.5 | ≦0.06 | 0.125 | ≦0.06 | 1 | 0.25 | 0.25 | 0.125 | ≦0.06 | ≦0.06 | ≦0.06 |
| Entercoccus faecalis 276 | 1 | 0.125 | 1 | 0.25 | 1 | 1 | 1 | 0.5 | ≦0.06 | ≦0.06 | ≦0.06 |
| Entercoccus gallinarum 245 | 2 | 0.125 | 2 | 2 | 2 | 2 | 4 | 2 | 4 | 8 | 0.125 |
| Haemophilus influenzae RD | | >64 | | | | | | | | | |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |

| Organism | 139 | 140 | 141 | 142 | 143 | 144 | 145 | 146 | 147 | 148 | 149 |
|---|---|---|---|---|---|---|---|---|---|---|---|
| Staphylococcus aureus 446 | 0.5 | 0.125 | 2 | 2 | 0.05 | 16 | 0.5 | 0.5 | 0.5 | 1 | 0.5 |
| Staphylococcus aureus 489 | 0.25 | ≦0.06 | 0.25 | 0.5 | ≦0.06 | 4 | ≦0.06 | 0.25 | | 0.25 | ≦0.06 |
| Staphylococcus aureus 447 | 1 | 0.25 | 1 | 2 | 4 | 16 | 1 | 2 | 0.125 | 1 | 4 |
| Staphylococcus aureus X400 | 0.25 | ≦0.06 | 0.25 | 1 | 0.125 | 8 | 0.25 | 0.5 | 4 | ≦0.06 | ≦0.06 |
| Staphylococcus aureus X778 | 0.125 | 0.25 | 0.5 | 1 | ≦0.06 | 8 | 0.125 | ≦0.06 | 0.25 | 2 | 0.5 |
| Staphylococcus aureus 491 | 0.5 | 0.25 | 0.5 | 0.5 | 0.5 | 8 | 0.5 | 1 | ≦0.06 | 0.125 | 0.5 |
| Staphylococcus aureus S13E | ≦0.06 | ≦0.06 | 0.25 | 2 | 0.125 | 8 | 0.125 | 0.5 | 1 | 1 | 0.25 |
| Staphylococcus aureus SA1199 | 0.125 | ≦0.06 | 0.25 | 1 | 0.125 | 8 | 0.25 | ≦0.06 | 0.5 | 2 | 0.25 |

TABLE 3-continued

In Vitro Activity of Formula I Compounds
MIC (mcg/ml)/Compound

| Organism | | | | | | | | | | |
|---|---|---|---|---|---|---|---|---|---|---|
| Staphylococcus aureus SA1199A | ≤0.06 | ≤0.06 | ≤0.06 | ≤0.06 | ≤0.06 | 2 | ≤0.06 | ≤0.06 | 0.25 | ≤0.06 | ≤0.06 |
| Staphylococcus aureus SA1199B | 2 | ≤0.06 | 2 | 2 | 0.25 | 8 | ≤0.06 | ≤0.06 | ≤0.06 | 0.5 | 1 |
| Staphylococcus haemolyticus 105 | 4 | 2 | 1 | 1 | 8 | 64 | 2 | 2 | 1 | 1 | 4 |
| Staphylococcus haemolyticus 415 | 8 | 8 | 4 | 1 | 32 | >64 | 8 | 4 | 8 2 | 16 | |
| Staphylococcus epidermidis 270 | 1 | 0.25 | 1 | 0.25 | 1 | 16 | 1 | 2 | 16 | 0.5 | 1 |
| Entercoccus faecium 180 | 2 1 | 0.5 | 0.5 | 4 | 8 | 4 | 8 | 2 | 0.25 | 1 | |
| Entercoccus faecium 180-1 | ≤0.06 | ≤0.06 | ≤0.06 | ≤0.06 | ≤0.06 | 4 | ≤0.06 | ≤0.06 | 2 | ≤0.06 | ≤0.06 |
| Entercoccus faecalis 2041 | ≤0.06 | ≤0.06 | ≤0.06 | ≤0.06 | 0.125 | 8 | 0.25 | 0.5 | ≤0.06 | ≤0.06 | ≤0.06 |
| Entercoccus faecalis 276 | 1 | 0.5 | 0.5 | 1 | 0.25 | 8 | 0.125 | 1 | 0.125 | ≤0.06 | ≤0.06 |
| Entercoccus gallinarum 245 | 8 | 8 | 4 | 1 | 32 | 4 | 0.25 | 0.5 | 0.125 | 2 | 16 |
| Haemophilus influenzae RD | | | | | | | | >64 | | | |
| Escherichia coli EC14 | >64 | >64 | >64 | >64 | >64 | >64 | >64 | >64 | >64 | >64 | >64 |
| Streptococcus pyogenes C203 | ≤0.06 | ≤0.06 | ≤0.06 | ≤0.06 | ≤0.06 | 0.5 | ≤0.06 | ≤0.06 | ≤0.06 | ≤0.06 | ≤0.06 |
| Streptococcus pneumoniae P1 | ≤0.06 | ≤0.06 | ≤0.06 | ≤0.06 | ≤0.06 | ≤0.06 | ≤0.06 | ≤0.06 | ≤0.06 | ≤0.06 | ≤0.06 |

| Organism | 150 | 151 | 152 | 153 | 154 | 155 | 156 | 157 | 158 | 159 | 160 |
|---|---|---|---|---|---|---|---|---|---|---|---|
| Staphylococcus aureus 446 | 1 | 2 | 2 | 0.5 | 2 | 2 | 2 | 0.5 | 2 | 0.5 | 2 |
| Staphylococcus aureus 489 | 0.5 | ≤0.06 | 0.5 | 1 | 1 | 0.5 | 1 | 0.5 | 2 | 0.25 | 0.21 |
| Staphylococcus aureus 447 | 0.5 | 1 | 8 | 0.5 | 2 | 8 | 1 | 0.25 | 4 | 4 | 1 |
| Staphylococcus aureus X400 | ≤0.06 | ≤0.06 | 1 | 0.5 | 2 | 1 | 2 | 0.5 | 4 | 4 | 4 |
| Staphylococcus aureus X778 | 2 | 1 | 0.5 | 0.5 | 0.5 | ≤0.06 | 1 | 0.25 | 4 | 2 | 4 |
| Staphylococcus aureus 491 | ≤0.06 | 0.5 | 1 | 0.125 | 0.5 | 1 | 1 | ≤0.06 | 1 | 2 | 0.125 |
| Staphylococcus aureus S13E | 0.25 | 0.25 | 0.5 | 0.125 | 0.25 | 1 | 1 | 0.25 | 2 | 1 | 1 |
| Staphylococcus aureus SA1199 | 1 | 0.125 | 1 | 0.5 | 2 | 1 | 1 | 1 | 4 | 0.125 | 0.25 |
| Staphylococcus aureus SA1199A | ≤0.06 | ≤0.06 | 0.25 | ≤0.06 | 0.125 | ≤0.06 | ≤0.06 | ≤0.06 | 1 | ≤0.06 | 0.125 |
| Staphylococcus aureus SA1199B | 0.5 | 0.25 | 0.5 | 0.25 | 0.25 | 1 | 0.5 | 1 | 4 | ≤0.06 | ≤0.06 |
| Staphylococcus haemolyticus 105 | 1 | 1 | 16 | 2 | 4 | 16 | 4 | 1 | 4 | 16 | 8 |
| Staphylococcus haemolyticus 415 | 2 | 4 | 16 | 1 | 4 | 16 | 2 | 1 | 8 | 8 | 8 |
| Staphylococcus epidermidis 270 | 0.25 | 0.5 | 4 | 0.25 | 0.5 | 1 | 1 | 0.25 | 4 | 0.5 | 1 |
| Entercoccus faecium 180 | 0.25 | 0.25 | 4 | 0.125 | 1 | 4 1 | ≤0.06 | 0.25 | 2 | 0.5 | |
| Entercoccus faecium 180-1 | ≤0.06 | ≤0.06 | 0.125 | ≤0.06 | ≤0.06 | ≤0.06 | ≤0.06 | ≤0.06 | 0.25 | ≤0.06 | ≤0.06 |
| Entercoccus faecalis 2041 | ≤0.06 | ≤0.06 | 0.125 | ≤0.06 | 0.125 | 0.125 | 0.5 | ≤0.06 | 1 | 0.125 | ≤0.06 |
| Entercoccus faecalis 276 | 1 | ≤0.06 | 0.25 | 0.5 | 0.5 | 0.25 | 2 | ≤0.06 | 2 | 0.125 | 2 |
| Entercoccus gallinarum 245 | 2 | 4 | 16 | 1 | 4 | 16 | 2 | 1 | 8 | 8 | 8 |
| Haemophilus influenzae RD | | | | | | 16 | 2 | | | | |
| Escherichia coli EC14 | >64 | >64 | >64 | >64 | >64 | >64 | >64 | >64 | >64 | >64 | >64 |
| Streptococcus pyogenes C203 | ≤0.06 | ≤0.06 | ≤0.06 | ≤0.06 | ≤0.06 | ≤0.06 | ≤0.06 | ≤0.06 | ≤0.06 | ≤0.06 | ≤0.06 |
| Streptococcus pneumoniae P1 | ≤0.06 | ≤0.06 | ≤0.06 | ≤0.06 | ≤0.06 | ≤0.06 | ≤0.06 | ≤0.06 | ≤0.06 | ≤0.06 | ≤0.06 |

| Organism | 161 | 162 | 163 | 164 | 165 | 166 | 167 | 168 | 169 | 170 | 171 |
|---|---|---|---|---|---|---|---|---|---|---|---|
| Staphylococcus aureus 446 | 0.5 | 0.5 | 1 | 2 | 1 | 2 | 1 | ≤0.06 | 0.25 | 2 | 1 |
| Staphylococcus aureus 489 | ≤0.06 | 0.25 | 8 | 2 | 2 | 2 | 16 | 0.125 | ≤0.06 | 0.25 | 0.5 |
| Staphylococcus aureus 447 | 1 | ≤0.06 | 0.5 | 2 | 0.5 | 2 | 4 | ≤0.06 | 2 | 0.5 | 1 |
| Staphylococcus aureus X400 | 0.5 | ≤0.06 | 0.5 | 0.5 | 0.5 | 1 | 1 | ≤0.06 | ≤0.06 | 0.5 | ≤0.06 |
| Staphylococcus aureus X778 | 0.5 | ≤0.06 | 2 | 1 | 0.125 | 1 | 16 | 0.5 | ≤0.06 | 1 | ≤0.06 |
| Staphylococcus aureus 491 | 0.5 | 0.25 | ≤0.06 | 1 | 0.5 | 0.5 | 2 | 0.5 | 0.25 | 0.5 | 0.25 |
| Staphylococcus aureus S13E | 0.125 | ≤0.06 | 1 | 4 | ≤0.06 | 4 | 4 | ≤0.06 | ≤0.06 | 0.25 | ≤0.06 |
| Staphylococcus aureus SA1199 | 0.25 | ≤0.06 | 2 | 2 | 0.25 | 2 | 2 | 0.5 | ≤0.06 | 1 | 0.25 |
| Staphylococcus aureus SA1199A | ≤0.06 | ≤0.06 | 0.5 | 0.5 | ≤0.06 | 0.125 | 4 | ≤0.06 | ≤0.06 | ≤0.06 | ≤0.06 |
| Staphylococcus aureus SA1199B | 0.25 | ≤0.06 | 1 | 2 | 1 | 2 | 4 | 1 | 0.125 | 0.25 | 0.25 |
| Staphylococcus haemolyticus 105 | 4 | 0.25 | 8 | 2 | 4 | 2 | 32 | 0.5 | 2 | 4 | 4 |
| Staphylococcus haemolyticus 415 | 8 | 2 | 8 | 2 | 4 | 2 | 16 | 2 | 4 | 4 | 8 |
| Staphylococcus epidermidis 270 | 1 | ≤0.06 | 4 | 1 | 1 | 0.5 | 8 | 0.125 | 0.25 | 1 | 1 |
| Entercoccus faecium 180 | 2 | ≤0.06 | 1 | 0.5 | 0.5 | 0.25 | 2 | 0.25 | 1 | 2 | 1 |
| Entercoccus faecium 180-1 | ≤0.06 | ≤0.06 | ≤0.06 | ≤0.06 | ≤0.06 | ≤0.06 | ≤0.06 | ≤0.06 | ≤0.06 | ≤0.06 | ≤0.06 |
| Entercoccus faecalis 2041 | ≤0.06 | ≤0.06 | 1 | 1 | ≤0.06 | ≤0.06 | 8 | ≤0.06 | ≤0.06 | ≤0.06 | ≤0.06 |
| Entercoccus faecalis 276 | 0.125 | ≤0.06 | 1 | 1 | 0.5 | 0.5 | 4 | 0.125 | ≤0.06 | 0.5 | 0.125 |
| Entercoccus gallinarum 245 | 8 | 2 | 8 | 2 | 4 | 2 | 16 | 2 | 4 | 4 | 8 |
| Haemophilus influenzae RD | | | | | | | | | | >64 | >64 |
| Escherichia coli EC14 | >64 | >64 | >64 | >64 | >64 | >64 | >64 | >64 | >64 | >64 | >64 |
| Streptococcus pyogenes C203 | ≤0.06 | ≤0.06 | ≤0.06 | ≤0.06 | ≤0.06 | ≤0.06 | 0.25 | ≤0.06 | ≤0.06 | ≤0.06 | ≤0.06 |
| Streptococcus pneumoniae P1 | ≤0.06 | ≤0.06 | ≤0.06 | ≤0.06 | ≤0.06 | ≤0.06 | ≤0.06 | ≤0.06 | ≤0.06 | ≤0.06 | ≤0.06 |

| Organism | 172 | 173 | 174 | 175 | 176 | 177 | 178 | 179 | 180 | 181 | 182 |
|---|---|---|---|---|---|---|---|---|---|---|---|
| Staphylococcus aureus 446 | 4 | 4 | 0.5 | 1 | 2 | 0.5 | 1 | 0.125 | 0.125 | ≤0.06 | 2 |
| Staphylococcus aureus 489 | 0.5 | 2 | ≤0.06 | 0.25 | 0.5 | ≤0.06 | 0.125 | ≤0.06 | ≤0.06 | ≤0.06 | 2 |
| Staphylococcus aureus 447 | 0.5 | 4 | 4 | 1 | 1 | 4 | 0.5 | 0.25 | 0.125 | ≤0.06 | 0.25 |
| Staphylococcus aureus X400 | 0.5 | 4 | ≤0.06 | 0.125 | 1 | ≤0.06 | 0.125 | ≤0.06 | ≤0.06 | ≤0.06 | 1 |
| Staphylococcus aureus X778 | 2 | 4 | ≤0.06 | 0.5 | 1 | 2 | 1 | ≤0.06 | ≤0.06 | ≤0.06 | 2 |
| Staphylococcus aureus 491 | 0.5 | 2 | 1 | 0.5 | 2 | 0.5 | 0.125 | 0.125 | 0.5 | | 1 |
| Staphylococcus aureus S13E | ≤0.06 | 4 | ≤0.06 | 0.25 | 2 | 0.25 | 0.5 | 0.25 | ≤0.06 | ≤0.06 | 0.25 |
| Staphylococcus aureus SA1199 | 1 | 2 | ≤0.06 | ≤0.06 | 2 | 0.25 | 1 | 1 | 0.125 | ≤0.06 | 2 |
| Staphylococcus aureus SA1199A | ≤0.06 | 0.5 | ≤0.06 | 0.5 | >64 | 0.5 | ≤0.06 | ≤0.06 | ≤0.06 | ≤0.06 | ≤0.06 |

TABLE 3-continued

In Vitro Activity of Formula I Compounds
MIC (mcg/ml)/Compound

| Organism | | | | | | | | | | |
|---|---|---|---|---|---|---|---|---|---|---|
| Staphylococcus aureus SA1199B | ≦0.06 | 4 | 0.125 | ≦0.06 | 1 | 0.25 | 1 | 0.125 | ≦0.06 | ≦0.06 | 4 |
| Staphylococcus haemolyticus 105 | 0.25 | 2 | 4 | 2 | 4 | 4 | 1 | 0.5 | 2 | 0.25 | 2 |
| Staphylococcus haemolyticus 415 | 2 | 4 | 16 | 4 | 2 | 16 | 2 | 1 | 2 | 1 | 4 |
| Staphylococcus epidermidis 270 | 0.5 | 2 | 2 | 0.5 | 0.5 | 1 | 0.25 | 0.25 | 0.125 | 0.125 | 0.25 |
| Entercoccus faecium 180 | 0.5 | 0.5 | 2 | 1 | 2 | 4 | 0.25 | ≦0.06 | 8 | 4 | 2 |
| Entercoccus faecium 180-1 | ≦0.06 | 0.5 | ≦0.06 | ≦0.06 | ≦0.06 | ≦0.06 | ≦0.06 | ≦0.06 | 0.125 | ≦0.06 | ≦0.06 |
| Entercoccus faecalis 2041 | ≦0.06 | 0.5 | ≦0.06 | ≦0.06 | 0.125 | 0.25 | ≦0.06 | ≦0.06 | 0.25 | 0.125 | 1 |
| Entercoccus faecalis 276 | 0.125 | 2 | ≦0.06 | ≦0.06 | 2 | 0.25 | 0.5 | ≦0.06 | 2 | 2 | 1 |
| Entercoccus gallinarum 245 | 2 | 4 | 16 | 4 | 2 | 16 | 2 | 1 | 0.25 | ≦0.06 | 1 |
| Haemophilus influenzae RD | 32 | >64 | >64 | 16 | 8 | >64 | 4 | 4 | | 32 | >64 |
| Escherichia coli EC14 | >64 | >64 | >64 | >64 | >64 | >64 | >64 | >64 | >64 | >64 | >64 |
| Streptococcus pyogenes C203 | ≦0.06 | ≦0.06 | ≦0.06 | 0.5 | 0.25 | 16 | ≦0.06 | ≦0.06 | ≦0.06 | ≦0.06 | ≦0.06 |
| Streptococcus pneumoniae P1 | ≦0.06 | ≦0.06 | ≦0.06 | 0.5 | 0.25 | 8 | ≦0.06 | ≦0.06 | ≦0.06 | ≦0.06 | ≦0.06 |

| Organism | 183 | 184 | 185 | 186 | 189 | 190 | 191 | 192 | 193 | 194 | 195 |
|---|---|---|---|---|---|---|---|---|---|---|---|
| Staphylococcus aureus 446 | ≦0.06 | 2 | ≦.06 | ≦.06 | 0.5 | 0.25 | 2 | 0.5 | 0.5 | ≦0.06 | 0.5 |
| Staphylococcus aureus 489 | ≦0.06 | ≦.06 | ≦.06 | ≦.06 | 1 | 0.125 | 2 | 1 | 0.125 | 0.125 | 1 |
| Staphylococcus aureus 447 | ≦0.06 | ≦.06 | ≦.06 | ≦.06 | 0.5 | 1 | 2 | 2 | ≦0.06 | 0.5 | 1 |
| Staphylococcus aureus X400 | ≦0.06 | 0.5 | ≦.06 | ≦.06 | 0.125 | ≦0.06 | 1 | 1 | 0.25 | ≦0.06 | 2 |
| Staphylococcus aureus X778 | ≦0.06 | 0.5 | ≦.06 | ≦.06 | 0.25 | 0.125 | 2 | 1 | ≦0.06 | 0.5 | 0.5 |
| Staphylococcus aureus 491 | 0.125 | 0.5 | ≦.06 | ≦.06 | ≦0.06 | 0.125 | 1 | 0.5 | ≦0.06 | ≦0.06 | 0.5 |
| Staphylococcus aureus S13E | ≦0.06 | 1 | ≦.06 | ≦.06 | 0.5 | 0.125 | 2 | 1 | ≦0.06 | ≦0.06 | 2 |
| Staphylococcus aureus SA1199 | ≦0.06 | 0.125 | ≦.06 | ≦.06 | 0.5 | 0.25 | 2 | 2 | 0.125 | 0.5 | 0.5 |
| Staphylococcus aureus SA1199A | ≦0.06 | ≦.06 | ≦.06 | ≦.06 | ≦0.06 | ≦0.06 | 0.5 | 0.25 | ≦0.06 | ≦0.06 | ≦0.06 |
| Staphylococcus aureus SA1199B | ≦0.06 | 1 | ≦.06 | ≦.06 | 1 | 0.5 | 2 | 0.5 | 0.125 | 0.125 | 1 |
| Staphylococcus haemolyticus 105 | ≦0.06 | 0.25 | ≦.06 | 0.5 | 1 | 8 | 2 | 1 | 035 | 1 | 1 |
| Staphylococcus haemolyticus 415 | ≦0.06 | ≦.06 | ≦.06 | 1 | 1 | 8 | 8 | 2 | 1 | 2 | 4 |
| Staphylococcus epidermidis 270 | ≦0.06 | 4 | ≦.06 | 0.125 | 0.25 | 2 | 2 | 1 | 0.25 | 0.5 | 0.25 |
| Entercoccus faecium 180 | 2 | 8 | 0.125 | 2 | 0.125 | 8 | 4 | 0.25 | ≦0.06 | ≦0.06 | 0.5 |
| Entercoccus faecium 180-1 | ≦0.06 | ≦.06 | ≦.06 | ≦.06 | ≦0.06 | ≦0.06 | 0.25 | 0.125 | ≦0.06 | ≦0.06 | ≦0.06 |
| Entercoccus faecalis 2041 | ≦0.06 | 1 | ≦.06 | ≦.06 | ≦0.06 | ≦0.06 | 1 | 0.125 | ≦0.06 | ≦0.06 | ≦0.06 |
| Entercoccus faecalis 276 | 0.125 | 0.5 | ≦.06 | ≦.06 | 0.25 | 0.125 | 4 | 0.5 | ≦0.06 | 0.125 | 0.25 |
| Entercoccus gallinarum 245 | 0.5 | 4 | ≦.06 | 2 | 1 | 8 | 8 | 2 | 1 | 2 | 4 |
| Haemophilus influenzae RD | >64 | 64 | 8 | | 32 | >64 | >64 | >64 | >64 | >64 | 32 |
| Escherichia coli EC14 | >64 | >64 | >64 | >64 | >64 | >64 | >64 | >64 | >64 | >64 | >64 |
| Streptococcus pyogenes C203 | ≦0.06 | | ≦.06 | ≦.06 | ≦0.06 | ≦0.06 | ≦0.06 | ≦0.06 | ≦0.06 | ≦0.06 | ≦0.06 |
| Streptococcus pneumoniae P1 | ≦0.06 | | ≦.06 | ≦.06 | ≦0.06 | ≦0.06 | ≦0.06 | ≦0.06 | ≦0.06 | ≦0.06 | ≦0.06 |

| Organism | 196 | 197 | 198 | 199 | 200 | 201 | 202 | 203 | 204 | 205 |
|---|---|---|---|---|---|---|---|---|---|---|
| Staphylococcus aureus 446 | 0.5 | 1 | 1 | 0.5 | 1 | 4 | 4 | 0.5 | 0.125 | 2 |
| Staphylococcus aureus 489 | 1 | 2 | 0.125 | 2 | 0.25 | 8 | 4 | 0.5 | 0.25 | 0.5 |
| Staphylococcus aureus 447 | 0.5 | 2 | 0.125 | 1 | 0.5 | 16 | 8 | 1 | ≦0.06 | 0.5 |
| Staphylococcus aureus X400 | 0.5 | 2 | 0.5 | 2 | 1 | 4 | 4 | 1 | 0.125 | 0.5 |
| Staphylococcus aureus X778 | 1 | 2 | 0.125 | 1 | 0.5 | 4 | 4 | 1 | 0.5 | 0.5 |
| Staphylococcus aureus 491 | 0.25 | 1 | ≦0.06 | 0.5 | 0.125 | 4 | 8 | 1 | ≦0.06 | 0.5 |
| Staphylococcus aureus S13E | 1 | 2 | 0.125 | 0.5 | 0.5 | 8 | 4 | 2 | 0.5 | 0.5 |
| Staphylococcus aureus SA1199 | 0.5 | 2 | 0.5 | 1 | 1 | 8 | 8 | 2 | 0.125 | 1 |
| Staphylococcus aureus SA1199A | ≦0.06 | 1 | ≦0.06 | 0.125 | ≦0.06 | 2 | 2 | 0.5 | | ≦0.06 |
| Staphylococcus aureus SA1199B | 0.5 | 2 | 0.5 | 1 | 1 | 16 | 8 | 1 | 0.25 | 0.5 |
| Staphylococcus haemolyticus 105 | 0.5 | 1 | 0.5 | 2 | 1 | 8 | 4 | 1 | 0.5 | 1 |
| Staphylococcus haemolyticus 415 | 1 | 4 | 1 | 4 | 2 | 8 | 8 | 2 | 0.25 | 1 |
| Staphylococcus epidermidis 270 | 0.25 | 0.5 | 0.25 | 0.5 | 0.25 | 4 | 4 | 0.5 | 0.5 | 0.125 |
| Entercoccus faecium 180 | 0.5 | 0.5 | ≦0.06 | 0.5 | 0.25 | 0.5 | 0.5 | 0.125 | 0.25 | 0.5 |
| Entercoccus faecium 180-1 | ≦0.06 | 0.25 | ≦0.06 | ≦0.06 | ≦0.06 | 0.5 | 0.5 | ≦0.06 | 0.125 | ≦0.06 |
| Entercoccus faecalis 2041 | ≦0.06 | 0.25 | ≦0.06 | ≦0.06 | ≦0.06 | 1 | 1 | 0.25 | ≦0.06 | 0.25 |
| Entercoccus faecalis 276 | 0.25 | 1 | 0.25 | 1 | 0.5 | 4 | 4 | 0.5 | ≦0.06 | 0.5 |
| Entercoccus gallinarum 245 | 1 | 4 | 1 | 4 | 2 | 8 | 8 | 2 | 0.25 | 1 |
| Haemophilus influenzae RD | 32 | 32 | 32 | 32 | 32 | 32 | 32 | 16 | 2 | 16 |
| Escherichia coli EC14 | >64 | >64 | >64 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 |

| Organism | 206 | 207 | 208 | 209 | 210 | 211 | 212 | 213 | 214 | 215 |
|---|---|---|---|---|---|---|---|---|---|---|
| Staphylococcus aureus 446 | 0.5 | 8 | 1 | 1 | 2 | 1 | ≦0.06 | ≦0.06 | 1 | 0.5 |
| Staphylococcus aureus 489 | 1 | 4 | 0.5 | 1 | 1 | 0.25 | ≦0.06 | ≦0.06 | 1 | 2 |
| Staphylococcus aureus 447 | 0.5 | 8 | 1 | 1 | 0.5 | 0.5 | 0.25 | 0.25 | 2 | 0.5 |
| Staphylococcus aureus X400 | 0.5 | 8 | 0.25 | 1 | ≦0.06 | 0.5 | ≦0.06 | ≦0.06 | 0.5 | 0.5 |
| Staphylococcus aureus X778 | 0.5 | 8 | 0.125 | 1 1 | 1 | ≦0.06 | ≦0.06 | 1 | ≦0.06 | |
| Staphylococcus aureus 491 | ≦0.06 | 1 | 0.5 | 0.25 | ≦0.06 | 0.25 | ≦0.06 | ≦0.06 | 1 | 0.25 |
| Staphylococcus aureus S13E | 1 | 8 | 0.25 | 0.5 | ≦0.06 | 0.5 | ≦0.06 | ≦0.06 | 1 | 2 |
| Staphylococcus aureus SA1199 | 0.5 | 8 | 0.5 | 0.25 | 0.5 | 0.5 | ≦0.06 | ≦0.06 | 0.5 | ≦0.06 |
| Staphylococcus aureus SA1199A | ≦0.06 | 4 | ≦0.06 | ≦0.06 | ≦0.06 | 0.125 | ≦0.06 | ≦0.06 | 0.5 | 0.5 |
| Staphylococcus aureus SA1199B | 1 | 16 | 0.5 | 0.5 | 0.125 | 1 | ≦0.06 | ≦0.06 | 1 | 1 |

TABLE 3-continued

In Vitro Activity of Formula I Compounds
MIC (mcg/ml)/Compound

| Organism | | | | | | | | | | |
|---|---|---|---|---|---|---|---|---|---|---|
| Staphylococcus haemolyticus 105 | 0.5 | 8 | 0.25 | 0.5 | 1 | 0.5 | 1 | 0.5 | 1 | 2 |
| Staphylococcus haemolyticus 415 | 1 | 1 | 2 | 1 | 1 | 0.5 | 1 | 2 | 2 | 1 |
| Staphylococcus epidermidis 270 | 0.25 | 8 | 0.5 | 0.125 | 0.25 | 0.5 | ≦0.06 | 0.5 | ≦0.06 | 0.125 |
| Entercoccus faecium 180 | ≦0.06 | 1 | 0.25 | ≦0.06 | ≦0.06 | ≦0.06 | ≦0.06 | 0.125 | 0.25 | ≦0.06 |
| Entercoccus faecium 180-1 | ≦0.06 | ≦0.06 | ≦0.06 | ≦0.06 | ≦0.06 | ≦0.06 | ≦0.06 | ≦0.06 | ≦0.06 | ≦0.06 |
| Entercoccus faecalis 2041 | 0.25 | 0.125 | ≦0.06 | ≦0.06 | ≦0.06 | ≦0.06 | ≦0.06 | ≦0.06 | 0.125 | 0.25 |
| Entercoccus faecalis 276 | ≦0.06 | 0.25 | 0.125 | 0.25 | ≦0.06 | ≦0.06 | ≦0.06 | ≦0.06 | 0.25 | 2 |
| Entercoccus gallinarum 245 | 1 | 1 | 2 | 1 | 1 | ≦0.06 | 1 | 2 | 2 | 64 |
| Haemophilus influenzae RD | | | 32 | 16 | >64 | >64 | >64 | 32 | 32 | >64 |
| Escherichia coli EC14 | >64 | >64 | >64 | >64 | >64 | >64 | >64 | >64 | >64 | >64 |
| Streptococcus pyogenes C203 | | | ≦0.06 | ≦0.06 | ≦0.06 | ≦0.06 | | | | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 |

| Organism | 216 | 217 | 218 | 219 | 220 | 221 | 222 | 223 | 224 | 225 |
|---|---|---|---|---|---|---|---|---|---|---|
| Staphylococcus aureus 446 | 1 | 0.25 | 4 | 8 | 1 | 1 | | 0.25 | 0.5 | 1 |
| Staphylococcus aureus 489 | 1 | ≦0.06 | 1 | 8 | 0.5 | 0.25 | 0.125 | 1 | 0.25 | 2 |
| Staphylococcus aureus 447 | 1 | 1 | 1 | 8 | 0.5 | 0.5 | 0.5 | 0.5 | 0.5 | 1 |
| Staphylococcus aureus X400 | 1 | ≦0.06 | 0.25 | 8 | 0.5 | 0.5 | 0.125 | 1 | 0.125 | 1 |
| Staphylococcus aureus X778 | 0.25 | ≦0.06 | 1 | 8 | 0.5 | 0.5 | ≦0.06 | 1 | 0.125 | 0.5 |
| Staphylococcus aureus 491 | 1 | 0.25 | 0.5 | 4 | ≦0.06 | 0.125 | 0.125 | 0.125 | 0.125 | 1 |
| Staphylococcus aureus S13E | 1 | ≦0.06 | 32 | 8 | 0.5 | 0.5 | ≦0.06 | 0.5 | 0.25 | 1 |
| Staphylococcus aureus SA1199 | ≦0.06 | ≦0.06 | 4 | 4 | 1 | 1 | 1 | 2 | 0.25 | 1 |
| Staphylococcus aureus SA1199A | 1 | ≦0.06 | ≦0.06 | 1 | ≦0.06 | ≦0.06 | 0.125 | ≦0.06 | ≦0.06 | 0.25 |
| Staphylococcus aureus SA1199B | 0.5 | 0.125 | 0.25 | 8 | 0.5 | 1 | 0.125 | 1 | 0.5 | 2 |
| Staphylococcus haemolyticus 105 | 0.5 | 2 | 0.5 | 2 | 0.5 | 1 | 1 | 1 | 1 | 0.5 |
| Staphylococcus haemolyticus 415 | 0.25 | 8 | 4 | 2 | 0.5 | 2 | 1 | 1 | 0.5 | 4 |
| Staphylococcus epidermidis 270 | 0.125 | 0.5 | 1 | 4 | 1 | 0.125 | 0.5 | 0.5 | 0.25 | 1 |
| Entercoccus faecium 180 | ≦0.06 | 2 | ≦0.06 | 1 | 0.125 | ≦0.06 | ≦0.06 | ≦0.06 | ≦0.06 | ≦0.06 |
| Entercoccus faecium 180-1 | ≦0.06 | ≦0.06 | ≦0.06 | 1 | ≦0.06 | ≦0.06 | ≦0.06 | ≦0.06 | ≦0.06 | ≦0.06 |
| Entercoccus faecalis 2041 | 0.25 | ≦0.06 | 0.25 | 2 | ≦0.06 | 0.25 | ≦0.06 | ≦0.06 | ≦0.06 | 0.125 |
| Entercoccus faecalis 276 | 0.5 | ≦0.06 | ≦0.06 | 2 | 0.125 | 2 | ≦0.06 | 0.125 | ≦0.06 | 0.25 |
| Entercoccus gallinarum 245 | 64 | 8 | ≦0.06 | 2 | 0.5 | 32 | 1 | 1 | 0.5 | 4 |
| Haemophilus influenzae RD | >64 | >64 | >64 | 32 | >64 | >64 | 32 | >64 | 32 | >64 |
| Escherichia coli EC14 | >64 | >64 | >64 | >64 | >64 | ≦0.06 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | |

| Organism | 226 | 227 | 228 | 229 | 230 | 231 | 232 | 233 | 234 | 235 |
|---|---|---|---|---|---|---|---|---|---|---|
| Staphylococcus aureus 446 | 1 | 2 | 4 | 1 | 0.25 | 0.25 | 4 | 4 | 4 | 0.5 |
| Staphylococcus aureus 489 | 0.5 | 2 | 2 | 1 | 0.25 | ≦0.06 | 8 | 4 | 4 | 0.5 |
| Staphylococcus aureus 447 | 0.5 | 2 | 4 | 2 | 0.5 | 0.25 | 16 | 16 | 8 | 0.25 |
| Staphylococcus aureus X400 | 0.25 | 1 | 1 | 1 | 0.5 | ≦0.06 | 8 | 8 | 8 | 0.125 |
| Staphylococcus aureus X778 | 0.25 | 4 | 4 | 1 | 0.25 | ≦0.06 | 8 | 8 | 4 | 0.5 |
| Staphylococcus aureus 491 | 0.25 | 2 | 1 | 0.5 | 0.125 | ≦0.06 | 4 | 8 | 8 | 0.125 |
| Staphylococcus aureus S13E | 0.5 | 4 | 8 | 1 | 0.5 | ≦0.06 | 8 | 8 | 8 | 0.125 |
| Staphylococcus aureus SA1199 | 1 | 4 | 4 | 1 | 0.25 | ≦0.06 | 16 | 32 | 8 | 0.25 |
| Staphylococcus aureus SA1199A | 0.125 | 0.6 | ≦0.06 | ≦0.06 | ≦0.06 | ≦0.06 | 2 | 4 | 2 | ≦0.06 |
| Staphylococcus aureus SA1199B | 1 | 4 | 4 | 1 | 0.25 | ≦0.06 | 32 | 16 | 8 | 0.5 |
| Staphylococcus haemolyticus 105 | 2 | 2 | 2 | 1 | 1 | ≦0.06 | 2 | >64 | 8 | 0.5 |
| Staphylococcus haemolyticus 415 | 1 | 4 | 4 | 2 | 2 | 0.5 | 32 | >64 | 16 | 1 |
| Staphylococcus epidermidis 270 | 1 | 2 | 2 | 0.5 | 0.5 | 0.125 | 8 | 8 | 4 | 0.5 |
| Entercoccus faecium 180 | ≦0.06 | 0.25 | 1 | ≦0.06 | ≦0.06 | ≦0.06 | 0.5 | 2 | 1 | 0.5 |
| Entercoccus faecium 180-1 | ≦0.06 | ≦0.06 | ≦0.06 | ≦0.06 | ≦0.06 | ≦0.06 | 1 | 2 | 1 | ≦0.06 |
| Entercoccus faecalis 2041 | ≦0.06 | 0.25 | 0.25 | ≦0.06 | ≦0.06 | ≦0.06 | 2 | 2 | 0.5 | ≦0.06 |
| Entercoccus faecalis 276 | 0.25 | 0.5 | 1 | 0.25 | ≦0.06 | ≦0.06 | 8 | 8 | 4 | 0.125 |
| Entercoccus gallinarum 245 | 1 | 4 | 4 | 2 | 2 | 0.5 | 32 | >64 | 16 | 1 |
| Haemophilus influenzae RD | 32 | >64 | >64 | 2 | 32 | 32 | 16 | >64 | >64 | 8 |
| Escherichia coli EC14 | >64 | >64 | >64 | >64 | >64 | >64 | >64 | >64 | >64 | >64 |
| Streptococcus pyogenes C203 | ≦0.06 | ≦0.06 | 0.125 | ≦0.06 | ≦0.06 | ≦0.06 | ≦0.06 | | | ≦0.06 |
| Streptococcus pneumoniae P1 | ≦0.06 | ≦0.06 | ≦0.06 | ≦0.06 | ≦0.06 | ≦0.06 | ≦0.06 | 0.5 | 0.25 | ≦0.06 |

| Organism | 236 | 237 | 238 | 239 | 240 | 241 |
|---|---|---|---|---|---|---|
| Staphylococcus aureus 446 | 1 | 2 | 1 | 1 | 1 | 0.5 |
| Staphylococcus aureus 489 | 4 | 0.5 | 0.5 | 0.5 | 1 | 0.5 |
| Staphylococcus aureus 447 | 4 | 1 | 0.5 | 0.5 | 0.5 | 1 |
| Staphylococcus aureus X400 | 2 | 1 | 1 | 0.25 | 0.25 | 0.5 |
| Staphylococcus aureus X778 | 2 | 0.5 | 0.5 | 0.25 | 0.5 | 1 |
| Staphylococcus aureus 491 | 4 | 0.25 | 0.25 | 0.25 | 0.25 | 0.25 |
| Staphylococcus aureus S13E | 4 | 0.25 | 0.125 | 0.5 | 0.5 | 0.25 |
| Staphylococcus aureus SA1199 | 4 | 1 | 0.5 | 0.5 | 0.5 | 1 |
| Staphylococcus aureus SA1199A | 2 | ≦0.06 | ≦0.06 | ≦0.06 | ≦0.06 | ≦0.06 |
| Staphylococcus aureus SA1199B | 4 | 0.25 | 0.5 | 0.5 | 0.25 | 1 |
| Staphylococcus haemolyticus 105 | 4 | 1 | 0.5 | 1 | 1 | 1 |

TABLE 3-continued

In Vitro Activity of Formula I Compounds
MIC (mcg/ml)/Compound

| Organism | | | | | | |
|---|---|---|---|---|---|---|
| Staphylococcus haemolyticus 415 | 4 | 1 | 2 | 1 | 2 | 1 |
| Staphylococcus epidermidis 270 | 2 | 0.5 | 0.5 | 0.25 | 0.25 | 0.5 |
| Entercoccus faecium 180 | 1 | 0.25 | 0.125 | ≦0.06 | ≦0.06 | ≦0.06 |
| Entercoccus faecium 180-1 | 1 | ≦0.06 | ≦0.06 | ≦0.06 | ≦0.06 | ≦0.06 |
| Entercoccus faecalis 2041 | 1 | 0.125 | ≦0.06 | ≦0.06 | ≦0.06 | ≦0.06 |
| Entercoccus faecalis 276 | 2 | 1 | ≦0.06 | 0.25 | 0.5 | ≦0.06 |
| Entercoccus gallinarum 245 | 4 | 1 | ≦0.06 | 1 | 2 | ≦0.06 |
| Haemophilus influenzae RD | 32 | 8 | >64 | >64 | >64 | >64 |
| Escherichia coli EC14 | >64 | >64 | >64 | >64 | >64 | >64 |
| Streptococcus pyogenes C203 | ≦0.06 | ≦0.06 | ≦0.06 | | | ≦0.06 |
| Streptococcus pneumoniae P1 | ≦0.06 | ≦0.06 | ≦0.06 | ≦0.06 | ≦0.06 | ≦0.06 |

| Organism | 245 | 247 | 248 | 249 | 250 | 251 | 252 | 253 | 254 | 255 | 257 |
|---|---|---|---|---|---|---|---|---|---|---|---|
| Staphylococcus aureus 446 | ≦0.06 | 0.5 | 2 | 64 | 0.25 | 0.25 | 0.125 | 64 | 32 | 64 | ≦0.06 |
| Staphylococcus aureus 489 | ≦0.06 | 0.25 | 2 | >64 | ≦0.06 | ≦0.06 | ≦0.06 | 16 | 16 | >64 | ≦0.06 |
| Staphylococcus aureus 447 | ≦0.06 | 1 4 | >64 | 0.125 | 0.125 | ≦0.06 | 16 | 16 | >64 | 0.25 | |
| Staphylococcus aureus X400 | ≦0.06 | 0.5 | 4 | >64 | ≦0.06 | ≦0.06 | 0.125 | 32 | 8 | >64 | ≦0.06 |
| Staphylococcus aureus X778 | ≦0.06 | 0.5 | 4 | >64 | ≦0.06 | ≦0.06 | ≦0.06 | 16 | 4 | >64 | ≦0.06 |
| Staphylococcus aureus 491 | 0.5 | 0.5 | 1 | 32 | ≦0.06 | ≦0.06 | ≦0.06 | 2 | 1 | >64 | ≦0.06 |
| Staphylococcus aureus S13E | | 0.5 | 0.5 | >64 | ≦0.06 | ≦0.06 | 0.125 | 32 | 32 | >64 | ≦0.06 |
| Staphylococcus aureus SA1199 | 0.25 | 1 1 | >64 | ≦0.06 | ≦0.06 | 0.125 | 32 | 8 | >64 | ≦0.06 | |
| Staphylococcus aureus SA1199A | ≦0.06 | ≦0.06 | 1 | 8 | ≦0.06 | ≦0.06 | ≦0.06 | 1 | 0.5 | 16 | ≦0.06 |
| Staphylococcus aureus SA1199B | ≦0.06 | 0.5 | 8 | >64 | ≦0.06 | ≦0.06 | ≦0.06 | 32 | 16 | >64 | ≦0.06 |
| Staphylococcus haemolyticus 105 | 1 | 1 | 2 | >64 | 2 | 2 | 0.5 | 16 | 16 | >64 | 2 |
| Staphylococcus haemolyticus 415 | 8 | 2 | 4 | >64 | 4 | 4 | 1 | 16 | 16 | >64 | 8 |
| Staphylococcus epidermidis 270 | 0.5 | 1 | 0.5 | 32 | 0.25 | 0.25 | 0.125 | 8 | 8 | >64 | 0.25 |
| Entercoccus faecium 180 | 2 | 0.5 | 0.25 | 16 | 2 | 2 | 0.5 | 0.5 | 0.25 | >64 | 4 |
| Entercoccus faecium 180-1 | ≦0.06 | ≦0.06 | ≦0.06 | 4 | ≦0.06 | ≦0.06 | ≦0.06 | 0.5 | 0.25 | 16 | ≦0.06 |
| Entercoccus faecalis 2041 | ≦0.06 | 0.125 1 | >64 | ≦0.06 | ≦0.06 | ≦0.06 | 4 | 4 | 16 | ≦0.06 | |
| Entercoccus faecalis 276 | ≦0.06 | 0.25 | 2 | >64 | ≦0.06 | ≦0.06 | ≦0.06 | 16 | 8 | >64 | ≦0.06 |
| Entercoccus gallinarum 245 | ≦0.06 | 0.125 4 | >64 | 4 | 4 | 1 | 16 | 16 | >64 | ≦0.06 | |
| Haemophilus influenzae RD | >64 | >64 | >64 | >64 | >64 | >64 | >64 | >64 | >64 | >64 | >64 |
| Escherichia coli EC14 | 0.5 | >64 | >64 | >64 | >64 | >64 | >64 | >64 | >64 | >64 | >64 |
| Streptococcus pyogenes C203 | 2 | ≦0.06 | ≦0.06 | 0.5 | ≦0.06 | ≦0.06 | ≦0.06 | 0.25 | 0.5 | 16 | ≦0.06 |
| Streptococcus pneumoniae P1 | 1 | ≦0.06 | ≦0.06 | 1 | ≦0.06 | ≦0.06 | ≦0.06 | 0.125 | ≦0.06 | 1 | ≦0.06 |

| Organism | 258 | 260 | 262 | 263 | 265 | 266 | 267 | 268 | 269 | 270 | 271 |
|---|---|---|---|---|---|---|---|---|---|---|---|
| Staphylococcus aureus 446 | 1 | 2 | 2 | 1 | 2 | 4 | 0.5 | 2 | 2 | 1 | 1 |
| Staphylococcus aureus 489 | 1 | 2 | 1 | 0.25 | 0.5 | 4 | 0.25 | 1 | 0.25 | 0.25 | 1 |
| Staphylococcus aureus 447 | 1 | 4 | 1 | 2 | 2 | 4 | 0.5 | 4 | 4 | 0.5 | 2 |
| Staphylococcus aureus X400 | 2 | 4 | 2 | 0.5 | 0.5 | 4 | 0.5 | 2 | 0.5 | 1 | 2 |
| Staphylococcus aureus X778 | 1 | 1 | 1 | 0.5 | 0.5 | 2 | 1 | 2 | 0.25 | 0.5 | 0.5 |
| Staphylococcus aureus 491 | 1 | 1 | 1 | 1 | 2 | 2 | 1 | 1 | 1 | 0.25 | 0.5 |
| Staphylococcus aureus S13E | 2 | 4 | 1 | 1 | 0.5 | 4 | 1 | 4 | 1 | 2 | 1 |
| Staphylococcus aureus SA1199 | 2 | 2 | 0.5 | 1 | 2 | 4 | 2 | 4 | 0.25 | 1 | 2 |
| Staphylococcus aureus SA1199A | 2 | 0.5 | ≦0.06 | ≦0.06 | ≦0.06 | 0.5 | ≦0.06 | 0.5 | ≦0.06 | ≦0.06 | 0.5 |
| Staphylococcus aureus SA1199B | 0.25 | 2 | 0.5 | 1 | 0.5 | 2 | 1 | 2 | 0.5 | 2 | 1 |
| Staphylococcus haemolyticus 105 | 1 | 1 | 4 | 16 | 8 | 16 | 16 | 8 | 8 | 4 | 2 |
| Staphylococcus haemolyticus 415 | 2 | 2 | 2 | 8 | 1 | 8 | 4 | 4 | 4 | 2 | 2 |
| Staphylococcus epidermidis 270 | 2 | 1 | 1 | 4 | 4 | 2 | 4 | 1 | 8 | 1 | 1 |
| Entercoccus faecium 180 | 1 | 0.5 | 1 | ≦0.06 | 8 | 2 | 0.25 | 0.5 | 4 | 0.25 | 2 |
| Entercoccus faecium 180-1 | 4 | 0.25 | ≦0.06 | ≦0.06 | ≦0.06 | 0.5 | 0.125 | 0.25 | 0.125 | ≦0.06 | 0.125 |
| Entercoccus faecalis 2041 | 0.5 | 1 | 0.5 | ≦0.06 | 0.25 | 2 | 0.25 | 1 | 0.125 | 0.5 | 2 |
| Entercoccus faecalis 276 | 1 | 2 | 2 | 0.5 | 0.5 | 2 | 1 | 2 | 0.125 | 1 | 1 |
| Entercoccus gallinarum 245 | 1 | 0.25 | 2 | 8 | 1 | 8 | 4 | 4 | 4 | 2 | 2 |
| Haemophilus influenzae RD | >64 | >64 | >64 | >64 | >64 | >64 | >64 | >64 | >64 | >64 | >64 |
| Escherichia coli EC14 | >64 | >64 | >64 | 65 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 | ≦0.06 | ≦0.06 | ≦0.06 | ≦0.06 |

| Organism | 272 | 273 | 274 | 275 | 276 | 277 | 278 | 279 | 280 | 281 |
|---|---|---|---|---|---|---|---|---|---|---|
| Staphylococcus aureus 446 | 0.25 | 2 | 8 | 0.25 | 1 | 64 | 1 | 0.5 | 2 | 64 |
| Staphylococcus aureus 489 | 0.125 | 2 | 2 | ≦0.06 | 1 | 16 | 0.5 | 0.125 | 1 | 32 |
| Staphylococcus aureus 447 | 0.25 | 4 | 16 | 1 | 4 | >64 | 2 | 1 | 8 | >64 |
| Staphylococcus aureus X400 | 0.125 | 2 | 8 | 0.25 | 2 | 32 | 0.25 | 0.25 | 1 | >64 |
| Staphylococcus aureus X778 | 0.125 | 2 | 4 | ≦0.06 | 1 | 32 | 0.5 | 0.25 | 0.5 | 16 |
| Staphylococcus aureus 491 | 0.25 | 4 | 4 | 1 | 1 | 8 | 1 | 0.25 | 2 | >64 |
| Staphylococcus aureus S13E | 0.125 | 4 | 4 | 0.125 | 2 | 16 | 1 | 0.25 | 2 | 32 |
| Staphylococcus aureus SA1199 | 0.25 | 4 | 2 | ≦0.06 | 1 | 16 | 0.25 | 0.5 | 2 | >64 |
| Staphylococcus aureus SA1199A | ≦0.06 | ≦0.06 | 1 | ≦0.06 | 0.25 | 1 | 1 | ≦0.06 | 0.5 | 4 |
| Staphylococcus aureus SA1199B | ≦0.06 | 2 | 2 | 0.125 | 1 | 16 | 0.5 | ≦0.06 | 0.5 | 32 |
| Staphylococcus haemolyticus 105 | 0.125 | 4 | >64 | 1 | 4 | >64 | 0.5 | 4 | >64 | >64 |
| Staphylococcus haemolyticus 415 | 0.5 | 8 | >64 | 4 | 4 | >64 | 2 | 2 | 32 | >64 |

TABLE 3-continued

In Vitro Activity of Formula I Compounds
MIC (mcg/ml)/Compound

| Staphylococcus epidermidis 270 | ≦0.06 | 2 | 16 | 1 | 4 | 16 | 1 | 1 | 8 | >64 |
|---|---|---|---|---|---|---|---|---|---|---|
| Entercoccus faecium 180 | 0.5 | 2 | >64 | 1 | 4 | 2 | 1 | ≦0.06 | 32 | >64 |
| Entercoccus faecium 180-1 | ≦0.06 | 0.25 | 0.5 | ≦0.06 | 0.25 | 0.5 | ≦0.06 | ≦0.06 | 0.25 | 4 |
| Entercoccus faecalis 2041 | 0.125 | 0.5 | 1 | ≦0.06 | 1 | 2 | 0.125 | ≦0.06 | 1 | 8 |
| Entercoccus faecalis 276 | 0.125 | 2 | 1 | ≦0.06 | 1 | 1 | 0.25 | 0.125 | 0.5 | 8 |
| Entercoccus gallinarum 245 | 0.5 | 8 | >64 | 4 | 4 | >64 | 2 | 2 | 32 | >64 |
| Haemophilus influenzae RD | >64 | >64 | >64 | >64 | >64 | >64 | >64 | >64 | >64 | >64 |
| Escherichia coli EC14 | >64 | >64 | >64 | >64 | >64 | >64 | >64 | >64 | >64 | >64 |
| Streptococcus pyogenes C203 | ≦0.06 | ≦0.06 | 0.125 | ≦0.06 | ≦0.06 | ≦0.06 | ≦0.06 | ≦0.06 | 0.125 | 0.5 |
| Streptococcus pneumoniae P1 | ≦0.06 | ≦0.06 | ≦0.06 | ≦0.06 | ≦0.06 | ≦0.06 | ≦0.06 | ≦0.06 | 0.125 | ≦0.06 |

| Organism | 282 | 283 | 284 | 285 | 286 | 287 | 288 |
|---|---|---|---|---|---|---|---|
| Staphylococcus aureus 446 | 32 | 16 | 8 | 4 | 1 | 1 | 2 |
| Staphylococcus aureus 489 | 8 | 8 | 2 | 1 | 2 | 0.5 | 2 |
| Staphylococcus aureus 447 | >64 | 32 | 8 | 32 | 8 | 4 | 2 |
| Staphylococcus aureus X400 | 16 | 16 | 4 | 4 | 2 | 0.5 | 2 |
| Staphylococcus aureus X778 | 16 | 8 | 1 | 1 | 4 | 0.5 | 2 |
| Staphylococcus aureus 491 | 16 | 4 | 2 | 4 | 2 | 1 | 2 |
| Staphylococcus aureus S13E | 16 | 4 | 4 | 1 | 4 | 1 | 2 |
| Staphylococcus aureus SA1199 | 16 | 32 | 8 | 2 | 2 | 0.5 | 2 |
| Staphylococcus aureus SA1199A | 1 | 4 | 0.25 | 0.25 | ≦0.06 | >64 | 1 |
| Staphylococcus aureus SA1199B | 16 | 32 | 4 | 1 | 4 | 0.25 | 1 |
| Staphylococcus haemolyticus 105 | >64 | >64 | 32 | 16 | 8 | 8 | 2 |
| Staphylococcus haemolyticus 415 | >64 | 32 | 32 | 16 | 4 | 16 | 4 |
| Staphylococcus epidermidis 270 | >64 | 16 | 16 | 8 | 4 | 4 | 1 |
| Entercoccus faecium 180 | 32 | 4 | 8 | 16 | 8 | 16 | 4 |
| Entercoccus faecium 180-1 | 1 | 0.125 | 0.5 | 0.25 | 0.25 | 0.125 | 1 |
| Entercoccus faecalis 2041 | 4 | 2 | 1 | 0.5 | 1 | 0.125 | 1 |
| Entercoccus faecalis 276 | 4 | 16 | 8 | 0.5 | 1 | 0.25 | 2 |
| Entercoccus gallinarum 245 | >64 | 32 | 32 | 16 | 4 | 0.5 | 2 |
| Haemophilus influenzae RD | >64 | >64 | >64 | >64 | >64 | >64 | >64 |
| Escherichia coli EC14 | >64 | >64 | >64 | >64 | >64 | >64 | >64 |
| Streptococcus pyogenes C203 | ≦0.06 | ≦0.06 | ≦0.06 | ≦0.06 | ≦0.06 | ≦0.06 | ≦0.06 |
| Streptococcus pneumoniae P1 | ≦0.06 | ≦0.06 | ≦0.06 | ≦0.06 | ≦0.06 | ≦0.06 | ≦0.06 |

The formula I compounds have also shown in vivo antimicrobial activity against experimentally-induced infections in laboratory animals. When two doses of test compound were administered to mice experimentally infected with the test organism, the activity observed was measured as an $ED_{50}$ value (effective dose in mg/kg to protect 50% of the test animals: see W. Wick et al., *J. Bacteriol.* 81, 233–235 (1961)). $ED_{50}$ values observed for illustrative compounds are given in Table 4.

TABLE 4

In Vivo Activity of Formula I Compounds ED50
(mg/kg/2)

| Compound | Stapylococcus aureus | Streptococcus pyogenes | Streptococcus pneumoniae |
|---|---|---|---|
| vancomycin | 1.2 | 0.8 | 1.1 |
| A82846A | 0.19 | 0.084 | 0.39 |
| A82846B | 0.25 | 0.12 | 0.18 |
| A82846C | 1.3 | 1.5 | 4.6 |
| 1 | 0.086 | 0.052 | 0.025 |
| 2 | 0.27 | 0.014 | 0.025 |
| 4 | 0.36 | 0.012 | 0.036 |
| 5 | 0.13 | 0.039 | 0.036 |
| 6 | 0.15 | 0.013 | 0.021 |
| 8 | 0.12 | >0.5 | 0.273 |
| 12 | 0.13 | >0.5 | >0.5 |
| 14 | 0.43 | 0.37 | >0.5 |
| 22 | 0.049 | >0.5 | >.05 |
| 25 | 0.16 | 0.087 | 0.088 |
| 29 | 0.088 | 0.1 | 0.054 |
| 32 | 0.055 | 0.034 | 0.039 |
| 36 | 0.19 | 0.28 | 0.31 |

TABLE 4-continued

In Vivo Activity of Formula I Compounds ED50
(mg/kg/2)

| Compound | Stapylococcus aureus | Streptococcus pyogenes | Streptococcus pneumoniae |
|---|---|---|---|
| 39 | 0.1 | 0.045 | <0.031 |
| 41 | n.d. | 0.082 | 0.087 |
| 46 | n.d. | 0.378 | 0.156 |
| 49 | 0.053 | 0.045 | <0.031 |
| 50 | 0.1 | 0.047 | 0.057 |
| 51 | 0.16 | 0.057 | 0.036 |
| 52 | 0.052 | 0.046 | 0.074 |
| 53 | 0.077 | 0.16 | 0.071 |
| 57 | 0.041 | 0.054 | 0.046 |
| 64 | n.d. | 0.044 | <0.031 |
| 87 | n.d. | 0.054 | 0.027 |
| 90 | n.d. | 0.058 | 0.049 |
| 93 | n.d. | 0.074 | 0.012 |
| 94 | n.d. | 0.16 | 0.049 |
| 97 | n.d. | 0.066 | 0.038 |
| 100 | n.d. | 0.062 | 0.046 |
| 104 | n.d. | 0.12 | 0.041 |
| 105 | n.d. | 0.12 | 0.041 |
| 106 | n.d. | 0.2 | 0.036 |
| 107 | n.d. | 0.27 | 0.092 |
| 108 | n.d. | 0.046 | 0.041 |
| 111 | n.d. | 0.099 | 0.084 |
| 114 | n.d. | 0.091 | 0.76 |
| 116 | n.d. | 0.89 | 0.058 |
| 118 | n.d. | 0.91 | 0.046 |
| 119 | n.d. | 0.16 | 0.08 |
| 120 | n.d. | 0.058 | 0.005 |
| 121 | n.d. | 0.041 | 0.047 |

TABLE 4-continued

In Vivo Activity of Formula I Compounds ED50 (mg/kg/2)

| Compound | Stapylococcus aureus | Streptococcus pyogenes | Streptococcus pneumoniae |
|---|---|---|---|
| 122 | n.d. | 0.23 | 0.31 |
| 123 | n.d. | 0.076 | 0.039 |
| 124 | n.d. | 0.092 | 0.041 |
| 131 | n.d. | <0.031 | 0.077 |
| 204 | n.d. | <0.031 | 0.046 |
| 211 | n.d. | <0.031 | 0.041 |
| 223 | n.d. | <0.031 | <0.031 |
| 229 | n.d. | 0.058 | 0.078 |
| 230 | n.d. | 0.046 | 0.078 | n.d = not done

One important aspect of the antimicrobial activity of many of the formula I compounds is their activity against vancomycin-resistant enterococci. This activity of illustrative in Table 5, which summarizes a comparison of the activity of illustrative compounds against representative vancomuycin-resistant and vancomycin-susceptible enterococci (*Enterococcus faecium* and *Enterococcus faecalis*, mean geometric MIC (mcg/mL)), as determined using the standard broth micro-dilution assay. End points were read after 24-hour incubation. Modification of the amino sugar of the disaccaride moiety provides improved activity against vancomycin-resistance strains over the parent glycopeptide antibiotic.

TABLE 5

| Compound No. | Vancomycin Resistant Strains | Vancomycin Sensitive Strains |
|---|---|---|
| vancomycin | 282 | 3.9 |
| A82846A | >64 | 1.7 |
| A82846B | 29 | 0.22 |
| A82846C | 353 | 1.3 |
| 1 | 0.25 | 0.0061 |
| 2 | 0.044 | 0.00038 |
| 3 | 2.8 | 0.11 |
| 4 | 0.50 | 0.062 |
| 5 | 0.50 | 0.072 |
| 6 | 1.2 | 0.14 |
| 7 | 2.8 | 0.43 |
| 8 | 1.0 | 0.57 |
| 9 | 11 | 0.38 |
| 10 | 3.4 | 3.5 |
| 11 | 6.7 | 0.22 |
| 12 | 1.7 | 1.1 |
| 13 | 19 | 0.76 |
| 14 | 0.50 | 0.76 |
| 15 | 6.7 | 0.14 |
| 16 | 9.5 | 0.67 |
| 17 | 9.5 | 0.38 |
| 18 | 6.7 | 0.38 |
| 19 | 4.8 | 0.22 |
| 20 | 4.8 | 0.38 |
| 21 | 5.7 | 4.3 |
| 22 | 1.0 | 1.5 |
| 23 | 5.7 | 2.0 |
| 24 | 54 | 0.67 |
| 25 | 4.0 | 0.22 |
| 26 | 54 | 0.66 |
| 27 | 45 | 1.5 |
| 28 | 4.7 | 0.71 |
| 29 | 0.21 | 0.031 |
| 30 | 4.7 | 0.071 |
| 31 | 9.5 | 1.2 |
| 32 | 0.50 | 0.089 |
| 33 | 2.8 | 0.18 |
| 34 | 4.0 | 3.4 |
| 35 | 5.6 | 0.25 |
| 36 | 0.25 | 0.21 |
| 37 | 2.4 | 0.25 |
| 38 | 4.0 | 0.42 |
| 39 | 1.2 | 0.09 |
| 40 | 0.50 | 0.31 |
| 41 | 0.84 | 0.21 |
| 42 | 1.7 | 0.089 |
| 43 | 13 | 1.1 |
| 44 | 13 | 0.50 |
| 45 | 2.0 | 0.50 |
| 46 | 0.71 | 0.50 |
| 47 | 4.7 | 0.57 |
| 48 | 4.8 | 0.50 |
| 49 | 0.71 | 0.083 |
| 50 | 0.12 | 0.054 |
| 51 | 0.84 | 0.22 |
| 52 | 0.59 | 0.11 |
| 53 | 0.35 | 0.25 |
| 54 | 1.7 | 0.56 |
| 55 | 13 | 1.7 |
| 56 | 19 | 1.0 |
| 57 | 0.36 | 0.041 |
| 58 | 5.7 | 0.76 |
| 59 | 51 | 0.42 |
| 60 | 19 | 3.0 |
| 61 | 16 | 0.65 |
| 62 | 9.5 | 0.22 |
| 63 | 54 | 0.66 |
| 64 | 0.71 | 0.077 |
| 65 | 2.4 | 0.20 |
| 66 | 16 | 0.76 |
| 67 | 1.7 | 0.16 |
| 68 | 6.7 | 0.25 |
| 69 | 13 | 0.44 |
| 70 | 2.0 | 0.092 |
| 71 | 11 | 0.57 |
| 72 | 4.7 | 0.28 |
| 73 | 11 | 0.25 |
| 74 | 11 | 0.33 |
| 75 | 16 | 0.50 |
| 76 | 8.0 | 0.29 |
| 78 | 16 | 0.76 |
| 79 | 0.84 | 0.042 |
| 80 | 1.7 | 0.25 |
| 81 | 1.0 | 0.042 |
| 82 | 22 | 0.50 |
| 83 | 54 | 1.7 |
| 84 | 23 | 0.66 |
| 85 | 3.4 | 0.11 |
| 86 | 1.4 | 0.036 |
| 87 | 0.71 | 0.047 |
| 88 | 1.7 | 0.055 |
| 89 | 11 | 0.44 |
| 90 | 0.71 | 0.041 |
| 91 | 2.8 | 0.11 |
| 92 | 1.7 | 0.082 |
| 93 | 0.42 | 0.042 |
| 94 | 0.50 | 0.041 |
| 95 | 1.7 | 0.054 |
| 96 | 1.4 | 0.11 |
| 97 | 0.71 | 0.054 |
| 98 | 2.4 | 0.095 |
| 99 | 72 | 0.76 |
| 100 | 0.71 | 0.042 |
| 101 | 4.0 | 0.25 |
| 102 | 2.0 | 0.13 |
| 103 | 4.0 | 0.33 |
| 104 | 1.2 | 0.062 |
| 105 | 0.84 | 0.062 |
| 106 | 0.71 | 0.034 |
| 107 | 0.59 | 0.082 |
| 108 | 0.84 | 0.04 |
| 109 | 72 | 0.22 |

TABLE 5-continued

| Compound No. | Vancomycin Resistant Strains | Vancomycin Sensitive Strains |
|---|---|---|
| 110 | 1.7 | 0.047 |
| 111 | 0.71 | 0.031 |
| 112 | 1.4 | 0.072 |
| 113 | 0.84 | 0.054 |
| 114 | 0.59 | 0.031 |
| 115 | 8.0 | 0.19 |
| 116 | 0.42 | 0.031 |
| 117 | 4.8 | 0.14 |
| 118 | 0.84 | 0.048 |
| 119 | 0.59 | 0.048 |
| 120 | 1.0 | 0.072 |
| 121 | 1.0 | 0.063 |
| 122 | 1.0 | 0.054 |
| 123 | 1.0 | 0.041 |
| 124 | 0.84 | 0.047 |
| 125 | 3.4 | 0.14 |
| 126 | 2.4 | 0.11 |
| 127 | 1.2 | 0.33 |
| 128 | 2.0 | 0.11 |
| 129 | 27 | 1.52 |
| 130 | 4.8 | 0.22 |
| 131 | 0.84 | 0.028 |
| 132 | 1.2 | 0.048 |
| 133 | 4.0 | 0.13 |
| 134 | 2.0 | 0.13 |
| 135 | 4.8 | 0.22 |
| 136 | 23 | 0.76 |
| 137 | 6.7 | 0.38 |
| 138 | 38 | 0.87 |
| 139 | 23 | 0.38 |
| 140 | 6.7 | 0.19 |
| 141 | 8.0 | 0.25 |
| 142 | 45 | 1.5 |
| 143 | 2.0 | 0.048 |
| 144 | 11 | 9.2 |
| 145 | 64 | 1.3 |
| 146 | 64 | 1.5 |
| 147 | 25 | 1.3 |
| 148 | 0.15 | 0.052 |
| 149 | 45 | 0.66 |
| 150 | 1.7 | 0.25 |
| 151 | 4.5 | 0.14 |
| 152 | 27 | 1.2 |
| 153 | 1.4 | 0.083 |
| 154 | 2.8 | 0.072 |
| 155 | 128 | 1.3 |
| 156 | 5.7 | 0.17 |
| 157 | 2.0 | 0.054 |
| 158 | 1.7 | 1.0 |
| 159 | 27 | 0.50 |
| 160 | 9.5 | 0.22 |
| 161 | 23 | 0.44 |
| 162 | 4.8 | 0.12 |
| 163 | 2.0 | 0.87 |
| 164 | 1.7 | 0.11 |
| 165 | 4.0 | 0.062 |
| 166 | 1.7 | 0.055 |
| 167 | 1.0 | 0.055 |
| 168 | 3.4 | 0.10 |
| 169 | 19 | 0.50 |
| 170 | 8.0 | 0.22 |
| 171 | 9.5 | 0.22 |
| 172 | 3.4 | 0.13 |
| 173 | 2.0 | 0.12 |
| 174 | 19 | 0.76 |
| 175 | 9.5 | 0.22 |
| 176 | 1.2 | 0.13 |
| 178 | 2.8 | 0.13 |
| 179 | 1.7 | 0.060 |
| 180 | >0.060 | 0.71 |
| 181 | 8.0 | 0.060 |
| 182 | 13 | 0.250 |
| 183 | 23 | 0.130 |
| 184 | 27 | 0.570 |
| 185 | 4.7 | 0.060 |
| 186 | 11 | 0.290 |
| 189 | 2.4 | 0.10 |
| 190 | 6.7 | 0.29 |
| 191 | 6.7 | 0.57 |
| 192 | 0.84 | 0.035 |
| 193 | 2 | 0.072 |
| 194 | 2.4 | 0.083 |
| 195 | 2.0 | 0.042 |
| 196 | 1.7 | 0.027 |
| 197 | 1.2 | 0.16 |
| 198 | 3.4 | 0.062 |
| 199 | 1.4 | 0.036 |
| 200 | 1.4 | 0.041 |
| 201 | 1.2 | 0.44 |
| 202 | 1.4 | 0.76 |
| 203 | 1.0 | 0.036 |
| 204 | 0.71 | 0.031 |
| 205 | 1 | 0.036 |
| 206 | 1.7 | 0.095 |
| 207 | 1.2 | 0.50 |
| 208 | 2.8 | 0.17 |
| 209 | 1.2 | 0.136 |
| 210 | 0.84 | 0.041 |
| 211 | 0.35 | 0.024 |
| 212 | 0.50 | 0.036 |
| 213 | 1.0 | 0.55 |
| 214 | 0.71 | 0.024 |
| 215 | 2.8 | 0.25 |
| 216 | 0.35 | 0.032 |
| 217 | 13 | 0.57 |
| 218 | 1.0 | 0.11 |
| 219 | 0.71 | 0.044 |
| 220 | 0.71 | 0.05 |
| 221 | 0.71 | 0.041 |
| 222 | 0.84 | 0.072 |
| 223 | 0.79 | 0.055 |
| 224 | 0.63 | 0.055 |
| 225 | 0.63 | 0.072 |
| 226 | 1.6 | 0.041 |
| 227 | 0.71 | 0.11 |
| 228 | 1.0 | 0.14 |
| 229 | 0.50 | 0.024 |
| 230 | 0.35 | 0.031 |
| 231 | 1.7 | 0.11 |
| 232 | 0.71 | 0.29 |
| 233 | 1.7 | 1.7 |
| 234 | 2 | 2 |
| 235 | 2.4 | 0.25 |
| 236 | 1.4 | 0.5 |
| 237 | 1.0 | 0.048 |
| 238 | 1.4 | 0.14 |
| 239 | 2.8 | 0.095 |
| 240 | 1.19 | 0.055 |
| 241 | 1.4 | 0.048 |
| 245 | 13 | 0.38 |
| 246 | 8 | 4 |
| 247 | 2.4 | 0.29 |
| 248 | 2 | 0.66 |
| 249 | 11 | 3.5 |
| 250 | 16 | 0.44 |
| 251 | 2 | 0.66 |
| 252 | 9.5 | 0.1 |
| 253 | 4.8 | 3 |
| 254 | 2 | 0.5 |
| 255 | 64 | 32 |
| 257 | 64 | 1 |
| 258 | 8 | 1 |
| 260 | 4.8 | 1.1 |
| 261 | >0.17 | 4.59 |
| 262 | 5.7 | 128 |
| 263 | 1.7 | 0.29 |
| 265 | 54 | 0.87 |
| 266 | 11 | 2.3 |
| 267 | 2.8 | 0.22 |
| 268 | 6.7 | 0.87 |

TABLE 5-continued

| Compound No. | Vancomycin Resistant Strains | Vancomycin Sensitive Strains |
|---|---|---|
| 269 | 38 | 1.1 |
| 270 | 2.8 | 0.66 |
| 271 | 5.7 | 0.33 |
| 272 | 4.75 | 0.072 |
| 273 | 2.8 | 0.38 |
| 274 | >128 | 9.2 |
| 275 | 16 | 0.33 |
| 276 | 23 | 1.3 |
| 277 | 32 | 1.1 |
| 278 | 8 | 0.29 |
| 279 | 2.4 | 0.11 |
| 280 | >128 | 7 |
| 281 | >128 | 37 |
| 282 | 45 | 2.6 |

TABLE 5-continued

| Compound No. | Vancomycin Resistant Strains | Vancomycin Sensitive Strains |
|---|---|---|
| 283 | 32 | 1.7 |
| 284 | 38 | 2.3 |
| 285 | 90 | 2.4 |
| 286 | 19 | 1.1 |
| 287 | 45 | 1.1 |
| 288 | 11 | 1.7 |

A number of the lactic acid bacteria including all Leuconostocs, all Pediococci, and some Lactobacilli, are intrinsically resistant to vancomycin. With the increased use of vancomycin, infections due to these bacteria have been reported with increasing frequency in immunocompromised patients (Handwerger et al., *Reviews of Infectious Disease* 12:602–610 (1990); Ruoff et al., *Journal of Clinical Microbiology* 26:2062–2068 (1988)). One important aspect of the antimicrobial activity of the formula I compounds is their activity against the vancomycin-resistant lactic acid bacteria. The compounds of the present are useful in inhibiting the growth of vancomycin- resistant lactic bacteria such as Leuconostoc, Pedicocci, and Lactobacilli and thus, controlling opportunistic infections by this group of bacteria. This activity is illustrated in Table 6, which summarizes a comparison of the activity of illustrative compounds against representative vancomycin-resistant lactic acid bacteria (*Pedicoccus acidilacti Pedicoccus pentosaceus, Leuconostoc lactis, Leuconostoc mesenteroides, Leuconostoc pseudomesenteroides, Leuconostoc citreum*, and *Lactobacillus confusus*, mean geometric MIC (mcg/mL)), as determined using a standard agar dilution assay on brain-heart infusion agar.

TABLE 6

In Vitro Activity of Formula I Compounds
MIC (mcg/ml)/Compound

| | Pediococcus acidilacti (mean of 10) | Pediococcus pentosaceus (mean of 2) | Leuconostoc lactis (mean of 2) | Leuconostoc mesenteroides (mean of 4) | Leuconostoc pseudomesenteroides | Leuconostoc citreum | Lactobacillus confusus |
|---|---|---|---|---|---|---|---|
| Vancomycin | 891 | 1024 | 1024 | 1024 | >1024 | >1024 | 1024 |
| A82846B | 141 | >256 | 64 | >256 | >256 | >256 | >256 |
| 1 | 18 | 23 | 23 | 64 | >128 | >128 | 64 |
| 2 | 5.9 | 11 | 4.0 | 16 | 32 | 64 | 16 |
| 4 | 7.5 | 16 | 16 | 16 | 32 | 128 | 32 |
| 5 | 2.8 | 8.0 | 8.0 | 8 | 16 | 64 | 16 |
| 6 | 4.3 | 8.0 | 8.0 | 9.5 | 16 | 64 | 16 |
| 14 | 3.7 | 5.7 | 8.0 | 11 | 32 | 64 | 32 |
| 29 | 4.0 | 8.0 | 5.7 | 6.7 | 16 | 32 | 8 |
| 32 | 12.1 | 16 | 16 | 16 | 32 | 64 | 16 |
| 36 | 9.2 | 16 | 16 | 16 | 32 | 32 | 32 |
| 39 | 26 | 32 | 32 | 32 | 64 | >64 | 32 |
| 41 | 71 | 91 | 91 | 91 | >128 | >128 | 64 |
| 49 | 55 | 64 | 64 | 64 | 128 | 128 | 64 |
| 50 | 51 | 64 | 64 | 64 | 128 | 128 | 64 |
| 51 | 87 | 91 | 64 | 76 | >128 | >128 | 64 |
| 52 | 55 | 64 | 64 | 76 | 64 | >128 | 64 |
| 58 | 55 | 64 | 64 | 64 | 128 | 128 | 64 |
| 108 | 12 | 23 | 8.0 | 10 | 32 | 64 | 16 |
| 118 | 16 | 16 | 11 | 13 | 32 | 64 | 16 |
| 122 | 24 | 16 | 16 | 16 | 32 | 64 | 16 |
| 124 | 20 | 16 | 16 | 16 | 64 | 64 | 16 |

Pharmaceutical formulations of the formula I compounds are also part of this invention, Thus, the compound, preferably in the form of a pharmaceutically acceptable salt, can be formulated for oral or parenteral administration for the therapeutic or prophylactic treatment of bacterial infections.

For example, the compound can be admixed with conventional pharmaceutical carriers and excipients and used in the form of tablets, capsules, elixirs, suspensions, syrups, wafers, and the like. The compositions comprising a formula I compound will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride, and alginic acid.

Disintegrators commonly used in the formulations of this invention include croscarmellose, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like canalso be used.

It may be desirable to add a coloring agent to make the dosage form more attractive in appearance or to help identify the product.

For intravenous (IV) use, a water soluble form of the antibiotic can be dissolved in one of the commonly used intravenous fluids and administered by infusion. Such fluids as, for example, physiological saline, Ringer's solution, or 5% dextrose solution can be used.

For intramuscular preparations, a sterile formulation of a suitable soluble salt form of the compound, for example the hydrochloride saly, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, for example, an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic, preferably in its salt form, in a suitable diluent in sterile, hermetically sealed ampoules. The concentration of the antibiotic in the unit dosage may vary, for example, from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The compounds of this invention are particularly useful in treating infections caused by methicillin-resistant staphylococci. Also, the compounds are useful in treating infection due to enterococci. Examples of such diseases are severe staphylococcal infections, for example, staphylococcal endocarditis and staphylococcal septicemia. The animal may be either susceptible to, or infected with, the microorganism. The method comprises administering to the animal an amount of a formula I compound which is effective for this purpose. In general, an effective amount of a formula I compound is a dose between about 0.5 and about 100 mg/kg. A preferred dose is from about 1 to about 60 mg/kg of active compound. A typical daily dose for an adult human is from about 50 mg to about 5 g.

In practicing this method, the antibiotic can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms in the infection.

A convenient method of practicing the treatment method is to administer the antibiotic via intravenous infusion. In this procedure a sterile formulation of a suitable soluble salt of the antibiotic is incorporated in a physiological fluid, such as 5% dextrose solution, and the resulting solution is infused slowly IV. Alternatively, the piggy-back method of IV infusion can also be used.

In order to illustrate more fully the operation of this invention, the following examples are provided, but are not to be construed as a limitation on the scope of the invention.

EXAMPLE 1

METHOD A

Preparation of Compound 2

A mixture of A82846B tricetate, (2.25 g, 1,27 mmol, 1.0 equivalents (eq)) in 1:1 DMF/methanol (140 mL) under an atmosphere of argon was treated with 4-biphenylcarboxaldehyde (331 mg, 2.12 mmol, 1.7 eq). The resulting mixture was heated to 70° C. and maintained as such for 1.75–2 hours. The solution was then treated with sodium cyanoborohydride (554 mg, 8.83 mmol, 6.9 eq). Heating at 70° C. was continued for an additional 1.75–2 hours after which the reaction mixture was cooled to room temperature, concentrated in vacuo, diluted with water (150 mL), and lyophilized to give a solid.

The solid was purified by preparative reverse-phase high performance liquid chromatography (HPLC) using a Waters 3×(40 ×100 mm) C18 Nova-Pak cartridge with Waters C18 Nova-pak guard insert and utilizing TEAP buffer system. The analytical method for analysis was: 0.2% TEA/phosphoric acid (TEAP), pH=3, the gradient system at time 0 was 5% $CH_3CN$/94.9% $H_2O$ with 0.2% TEAP held constant and at 20 minutes was 60% $CH_3CN$/39.8% $H_2O$ with 0.2% TEAP held constant. The UV wavelength used was 235 nm and the flow rate was 2 ml/minute. Analysis was done using a Waters Nova-pak C18 guard (8×100 mm) with a Nova-pak C18 guard insert. It is necessary to desalt the product after reverse phase purification when this HPLC method is used.

Desalting was accomplished by adding the purified product to 5–10 ml of $H_2O$. 1 N HCl was added dropwise with stirring to dissolve the sample. The pH at this point was approximately 1–3. The pH of the solution was then raised to 8.2 with 1 N NaOH. A white solid precipitated out of solution. The mixture was cooled, filtered, and dried under vacuum at room temperature for 8–15 hours to give the zwitter ion (or neutral compound) of the desired product, compound 2 (p-phenylbenzyl-A82846B), (1.02 g, 45%).

EXAMPLE 2

Preparation of Compound 4

A mixture of A82846B triacetate (1.5 g, 0.848 mmol, 1.0 eq) in methanol (100 mL) under an atmosphere of argon was treated with p-phenoxybenzaldehyde (298 mg, 1,51 mmol, 1.8 eq). The resulting mixture was heated to reflux and maintained as such for 2 hours. The solution was then treated with sodium cyanoborohydride (326 mg, 5.18 mmol, 6.1 eq). Heating at reflux was continued for an additional 2 hours after which the reaction mixture was cooled to room temperature and evaporated to dryness in vacuo.

The product was purified by reverse-phase HPLC with a TFA buffer. The analytical method for analysis was accomplished by using a Waters Nova-pak C18 RCM column (8×100 mm) with a Nova-pak C18 guard insert, eluting with a 2.0 ml/minute linear gradient of 15% acetonitrile/0.1% TFA at time zero to 80% acetonitrile/0.1% TFA at 15 minutes. The fractions containing the products were detected by ultraviolet scan at 235 nm. The organic solvent of the desired fractions was removed and the mixture was lyophilized to a white solid to give 0.618 mg of p-phenoxybenzyl.A82846B compound 4.tris(trifluroacetate) salt (20% yield). No desalting or further purification was necessary. This method is also especially useful in the preparation of Compound 2 wherein phenylbenzaldehyde is one of the starting materials.

EXAMPLE 3

Method B

Preparation of Compound 176

A mixture of A82846B.triacetate (280 mg, 0.157 mmol, 1.0 eq) in 1:1 DMF/methanol (30 mL) was treated with 8-phenyloctanal (59 mg, 0.29 mmol, 1.8 eq) and sodium cyanoborohydride (60 mg, 0.95 mmol, 6.1 eq). The resulting mixture was heated, under an atmosphere of nitrogen, to 70° C. and maintained as such for 1 hour. The reaction mixture was then cooled to room temperature and concentrated in vacuo to give a residue. Purification of the product was accomplished by reverse-phase preparative HPLC utilizing a Waters 2×(40×100 mm) C18 Nova-Pak cartridge with Waters C18 Nova-Pak guard insert. Elution was accomplished with a 30 minute linear gradient (time=0 minutes 95% TEAP (0.5% aqueous triethylamine adjusted to pH=3 with phosphoric acid)/5% $CH_3CN$ to t=30 minutes 20% TEAP/80% $CH_3CN$) with a flow rate of 40 mL/minute and UV detection at 280 nm. The desired fraction was concentrated in vacuo then desalted with a Waters Sep-Pak cartridge as described below. This afforded compound 176 in 22% yield (60 mg).

The resulting compound was desalted as follows. A Waters Sep-Pak cartridge was pre-wet with methanol (2–3 column volumes) then conditioned with water (2–3 column volumes). The sample, dissolved in a minimum volume of water, was loaded onto the Sep-Pak column which was then washed with water (2–3 column volumes) to remove the unwanted salts. The product was then eluted with an appropriate solvent system, typically 1:1 $CH_3CN/H_2O$, $CH_3CN$, and/or methanol. The organic solvent component was removed in vacuo and the resulting aqueous solution lyophilized to give the final product.

EXAMPLE 4

Preparation of Compound 229

A three liter 3-necked flask was fitted with a condenser, nitrogen inlet and overhead mechanical stirring apparatus. The flask was charged with pulverized A82846B acetate salt (20.0 g, $1.21 \times 10^{-3}$ mol) and methanol (1000 mL) under a nitrogen atmosphere. 4'-chlorobiphenylcarboxaldehyde (2.88 g, $1.33 \times 10^{-2}$ mol, 1.1 eq.) was added to this stirred mixture, followed by methanol (500 mL). Finally, sodium cyanoborohydride (0.84 g, $1.33 \times 10^{-2}$ mol, 1.1 eq.) was added followed by methanol (500 mL). The resulting mixture was heated to reflux (about 65° C.).

After 1 hour at reflux, the reaction mixture attained homogeneity. After 25 hours at reflux, the heat source was removed and the clear reaction mixture was measured with a pH meter (6.97 at 58.0° C.). 1 N NaOH (22.8 mL) was added dropwise to adjust the pH to 9.0 (at 54.7° C.). The flask was equipped with a distillation head and the mixture was concentrated under partial vacuum to a weight of 322.3 grams while maintaining the pot temperature between 40–45° C.

The distillation head was replaced with an addition funnel containing 500 mL of isopropanol (IPA). The IPA was added dropwise to the room temperature solution over 1 hour. After approximately ⅓ of the IPA was added, a granular precipitate formed. The remaining IPA was added at a faster rate after precipitation had commenced. The flask was weighed and found to hold 714.4 grams of the IPA/methanol slurry.

The flask was re-equipped with a still-head and distilled under partial vacuum to remove the remaining methanol. The resulting slurry (377.8 g) was allowed to chill in the freezer overnight. The crude product was filtered through a polypropylene pad and rinsed twice with 25 mL of cold IPA. After pulling dry on the funnel for 5 minutes, the material was placed in the vacuum oven to dry at 40° C. A light pink solid (22.87 g (theory =22.43 g)) was recovered. HPLC analysis versus a standard indicated 68.0% weight percent of Compound 229 (4-[4-chlorophenyl]benzyl-A82846B) in the crude solid, which translated into a corrected crude yield of 69.3%.

The products of the reaction were analyzed by reverse-phase HPLC utilizing a Zorbax SB-C18 column with ultraviolet light (UV; 330 nm) detection. A 20 minute gradient solvent system consisting of 95% aqueous buffer/5% $CH_3CN$ at time=0 minutes to 40% aqueous buffer/60% $CH_3CN$ at time=20 minutes was used, where the aqueous buffer was TEAP (5 ml $CH_3CN$, 3 ml phosphoric acid in 1000 ml water).

EXAMPLE 5

Preparation of Compound 252, 253, 254, 255

The following procedure is referred to herein as Method D. A 100 ml 3 necked flask was fitted with a condenser and charged with 0.75 g (0.45 mmol) of A82846B, 0.197 g (2 eqs., 0.91 mmol) of 4'-chloro-biphenylcarboxaldehyde, 0.086 g (3 eqs., 1.4 mmol) sodium cyanoborohydride, 25 ml methanol and 25 ml $H_2O$. The mixture was heated to reflux and monitored by HPLC. After 6.5 hours, heating was stopped and the mixture transferred to a single-neck recovery flask. Concentration in vacuo afforded 1.02 g of off-white solids. This material was subjected to preparative chromatography for isolation of the desired components.

The products of the reaction were analyzed by reverse-phase HPLC utilizing a Zorbax SB-C18 column with ultraviolet light (UV; 230 nm) detection. A 20 minute gradient solvent system consisting of 95% aqueous buffer/5% $CH_3CN$ at time=0 minutes to 40% aqueous buffer/60% $CH_3CN$ at time=20 minutes was used, where the aqueous buffer was TEAP (5 ml $CH_3CN$, 3 ml phosphoric acid in 1000 ml water). The resulting material was held for five minutes and then returned to 95% aqueous buffer/5% $CH_3CN$. The reaction yielded 9.19% starting material (A82846B), 14.93% Compound 229, 21.22% Compound 252, 10.53% Compound 253, 25.89% Compound 254, and 4.99% Compound 255.

In order to enrich for the formation of compounds 253, and 255, the following procedure, which is referred to herein as Method E, was utilized. A 100 ml, necked flask was charged with a condenser and nitrogen inlet. The flask was charged with 1 g (0.61 mmol) of A82846B, 0.394 g (3 eqs., 1.82 mmol) of 4'-chloro-biphenylcarboxaldehyde, 0.114 g (3 eqs., 1.8 mmol) sodium cyanoborohydride and 50 ml methanol). The mixture was heated to reflux and allowed to stir under nitrogen overnight. After 25 hours at reflux, heating was stopped and the mixture was transferred to a single-neck recovery flask and concentrated n vacuo. 1.42 g of off-white solids were recovered. Using the analytical HPLC method described above in this Example it was determined that the reaction yielded 5.19% of Compound 229, 25.14% of Compound 253, 10.15% of Compound 254, and 42.37% of Compound 255.

Preparative chromatography was used to isolate Compounds 252, 253, 254, 255. A 200 mg aliquot of either the preparation from Method D or E, above, was dissolved in 2.5 ml of 1:1 AcOH:methanol and injected into a waters Prep 3000 preparative chromatography unit with a Waters Nova-Pak C-18 reverse phase column (3×40mm ×100mm) using ultraviolet light (UV; 235 nm) detection. A 45 minute gradient solvent system consisting of 15% acetonitrile/75% water/10% of a 1% TFA aqueous buffer at time=0 minutes to 85% acetonitrile/15% water/10% of a 1% TFA aqueous buffer at time=45 minutes was used with a flow rate of 40 ml/min. Elution of the material was observed via a strip chart recorder. Fractions were collected. All fractions containing Compound 229 and/or mixtures were discarded. Fractions containing the pure components (Compounds 252, 253, 254, and 255) were combined, concentrated to remove organic solvents and lyophilized to afford the TFA salts of the derivatives. After re-analysis by HPLC to confirm purity, samples were submitted for FAB mass spectroscopy. Identification of the compounds was based upon the fragmentation patterns observed in the FAB spectra.

EXAMPLE 6

Table 7 summarizes the preparation and certain physical characteristics of the exemplified compounds. The yield of the product was calculated using the amount of the formula II compound as the limiting reagent. The following terms are found in Table 6 and are defined here. "Method" refers to the method of synthesis as described in Examples 1 and 2, or 3. "Reagent Equivalents" refers to the molar equivalents of the aldehyde and reducing agent relative to the formula II compound. "FAB-MS (M+3H)" refers to Fast atom bombardment-mass spectrometry.

TABLE 7

| Compound No. | Yield (%) | Method/ DMF: MeOH | Reagent Equivalents (aldehyde/ NaBH3CN) | FAB-MS (M + 3H) |
|---|---|---|---|---|
| 1 | 28 | A/1:1 | 1.7/6.9 | 1733* |
| 2 | 45 | A/1:1 | 1.7/6.9 | 1760 |
| 3 | 28 | A/1:1 | 1.8/7.6 | 1732** |
| 4 | 20 | A/0:1 | 1.8/6.1 | 1776*** |
| 5 | 30 | A/0:1 | 1.8/6.1 | 1790 |
| 6 | 10 | A/0:1 | 1.8/6.1 | 1768*** |
| 7 | 55 | A/0:1 | 1.8/6.1 | 1740*** |
| 8 | 16 | A/0:1 | 1.8/6.1 | 1826 |
| 9 | 32 | A/0:1 | 1.8/6.1 | 1764*** |
| 10 | 6 | A/0:1 | 1.8/6.1 | 1868 |
| 11 | 38 | A/0:1 | 1.8/6.1 | 1784 |
| 12 | 46 | A/0:1 | 1.8/6.1 | 1940 |
| 13 | 32 | A/0:1 | 1.8/6.1 | 1783** |
| 14 | 5.4 | A/1:1 | 1.9/4.2 | 1859 |
| 15 | 42 | A/0:1 | 1.8/6.1 | 1763 |
| 16 | 39 | A/0:1 | 1.8/6.1 | 1807** |
| 17 | 41 | A/0:1 | 1.8/6.1 | 1798 |
| 18 | 27 | A/0:1 | 1.8/6.1 | 1817 |
| 19 | 30 | A/0:1 | 1.8/6.1 | 1739 |
| 20 | 5 | A/1:1 | 1.8/1.8 | 1775* |
| 21 | 11 | A/1:1 | 1.8/1.8 | 1872* |
| 22 | 8 | A/1:1 | 1.8/1.8 | 1828** |
| 23 | ND | A/0:1 | 1.8/3.6 | 1888*** |
| 24 | 34 | A/0:1 | 1.7/2.5 | 1685 |
| 25 | 31 | A/0:1 | 1.8/6.1 | 1779 |
| 26 | 30 | A/0:1 | 1.7/2.5 | 1685 |
| 27 | 19 | A/0:1 | 1.8/2.5 | 1734** |
| 28 | 35 | A/0:1 | 1.6/1.6 | 1735 |
| 29 | 39 | A/0:1 | 1.6/1.6 | 1785** |
| 30 | 29 | A/0:1 | 1.6/1.6 | 1734** |
| 31 | 11 | A/0:1 | 1.7/2.5 | 1684** |
| 32 | 28 | A/0:1 | 1.5/1.6 | 1771** |
| 33 | ND | A/1:1 | 1.8/1.8 | 1789 |
| 34 | ND | A/1:1 | 1.8/1.8 | 1836 |
| 35 | ND | A/1:1 | 1.8/1.8 | 1785 |
| 36 | ND | A/1:1 | 1.8/1.8 | 1835 |
| 37 | 31 | A/0:1 | 1.5/1.5 | 1752*** |
| 38 | 16 | A/0:1 | 1.5/1.6 | 17.9 |
| 39 | 46 | A/0:1 | 1.5/1.5 | 1773 |
| 40 | 29 | A/1:1 | 1.8/1.8 | 1846* |
| 41 | 46 | A/0:1 | 1.5/1.5 | 1729 |
| 42 | 53 | A/0:1 | 1.5/1.5 | 1780 |
| 43 | 22 | A/0:1 | 1.1/1.5 | 1799*** |
| 44 | 42 | A/0:1 | 1.5/1.5 | 1749 |
| 45 | 50 | A/0:1 | 1.1/1.5 | 1841 |
| 46 | 38 | A/0:1 | 1.1/1.5 | 1850 |
| 47 | 40 | A/0:1 | 1.5/1.5 | 1687 |
| 48 | 22 | A/0:1 | 1.5/1.5 | 1728*** |
| 49 | 44 | A/0:1 | 1.5/1.5 | 1776*** |
| 50 | 32 | A/1:10 | 2.0/1.5 | 1774 |
| 51 | 32 | A/0:1 | 1.5/1.5 | 1820 |
| 52 | 31 | A/0:1 | 1.5/1.5 | 1819** |
| 53 | 43 | A/0:1 | 1.5/1.5 | 1896 |
| 54 | 4 | A/1:1 | 1.8/1.8 | 1789 |
| 55 | 21 | A/0:1 | 1.5/1.5 | 1767 |
| 56 | 20 | A/0:1 | 1.1/1.5 | 1741 |
| 57 | 29 | A/0:1 | 1.5/1.5 | 1820** |
| 58 | 22 | A/0:1 | 1.5/1.5 | 1727 |
| 59 | ND | A/1:1 | 1.8/1.8 | 1803 |
| 60 | 33 | A/0:1 | 1.1/1.5 | 1777** |
| 61 | 24 | A/0:1 | 1.1/1.5 | 1723 |
| 62 | ND | A/1:1 | 1.8/1.8 | 1789** |
| 63 | ND | A/1:1 | 1.8/1.8 | 1789** |
| 64 | 30 | A/0:1 | 1.5/1.5 | 1805 |
| 65 | 24 | A/0:1 | 1.1/1.5 | 1763 |
| 66 | 17 | A/0:1 | 1.1/1.5 | 1704*** |
| 67 | 22 | A/0:1 | 1.1/1.5 | 1766*** |
| 68 | ND | A/1:1 | 1.8/1.8 | 1802 |
| 69 | ND | A/1:1 | 1.8/1.8 | 1803 |
| 70 | 44 | A/0:1 | 1.1/1.5 | 1821 |
| 71 | 4 | A/0:1 | 1.1/1.5 | 1796*** |
| 72 | 32 | A/0:1 | 1.5/1.5 | 1750*** |
| 73 | ND | A/1:1 | 1.8/1.8 | 1753 |
| 74 | 17 | A/0:1 | 1.1/1.5 | 1815 |
| 75 | 23 | A/0:1 | 1.5/1.5 | 1806*** |
| 76 | 16 | A/1:1 | 1.8/1.8 | 1711 |
| 77 | ND | A/1:1 | 1.8/1.8 | 1742 |
| 78 | 5 | A/1:1 | 1.8/1.8 | 1728 |
| 79 | ND | A/1:1 | 1.8/1.8 | 1783** |
| 80 | 46 | A/0:1 | 1.5/1.5 | 1843**** |
| 81 | 52 | A/0:1 | 1.5/1.5 | 1844*** |
| 82 | 29 | A/0:1 | 1.5/1.5 | 1726*** |
| 83 | 7 | A/0:1 | 1.5/1.5 | 1798** |
| 84 | 8 | A/0:1 | 1.5/1.5 | 1700 |
| 85 | 30 | A/0:1 | 1.5/1.5 | 1775 |
| 86 | 45 | A/0:1 | 1.5/1.5 | 1809 |
| 87 | 42 | A/0:1 | 1.1/1.5 | 1854** |
| 88 | 36 | A/0:1 | 1.1/1.5 | 1854** |
| 89 | 43 | A/1:1 | 1.8/1.8 | 1711 |
| 90 | 13 | A/1:1 | 1.8/1.8 | 1787 |
| 91 | 20 | A/1:10 | 1.5/1.5 | 1759** |
| 92 | 23 | A/1:10 | 1.5/1.5 | 1777 |
| 93 | 42 | A/0:1 | 1.5/1.5 | 1823 |
| 94 | 41 | A/0:1 | 1.1/1.5 | 1854** |
| 95 | 49 | A/0:1 | 1.1/1.5 | 1789** |
| 96 | 34 | A/0:1 | 1.1/1.5 | 1832 |
| 97 | 42 | A/1:10 | 1.5/1.5 | 1773** |
| 98 | 31 | A/0:1 | 1/1.5 | 1805 |
| 99 | ND | A/1:1 | 1.8/1.8 | 1770** |

TABLE 7-continued

| Compound No. | Yield (%) | Method/ DMF: MeOH | Reagent Equivalents (aldehyde/ NaBH3CN) | FAB-MS (M + 3H) |
|---|---|---|---|---|
| 100 | ND | A/1:1 | 1.8/1.8 | 1787 |
| 101 | 34 | A/1:1 | 1.19/1.8 | 1761 |
| 102 | 41 | A/0:1 | 1.5/1.5 | 1805 |
| 103 | 37 | A/0:1 | 1/1.5 | 1788*** |
| 104 | 34 | A/0:1 | 1.1/1.5 | 1819** |
| 105 | ND | A/1:1 | 1.7/2.0 | 1838* |
| 106 | ND | A/1:1 | 1.7/2.0 | 1844 |
| 107 | ND | A/1:1 | 1.1/1.1 | 1802 |
| 108 | ND | A/0:1 | 1.8/1.8 | 1791** |
| 109 | ND | A/0:1 | 1.8/1.8 | 1789 |
| 110 | 15 | A/0:1 | 1.1/1.5 | 1881 |
| 111 | ND | A/1:1 | 1.8/1.8 | 1843 |
| 112 | 16 | A/1:1 | 1.8/1.8 | 1764 |
| 113 | 45 | A/0:1 | 1.1/1.5 | 1805** |
| 114 | 52 | A/0:1 | 1.1/1.5 | 1888** |
| 115 | 39 | A/0:1 | 1.1/1.5 | 1791 |
| 116 | ND | A/1:1 | 1.8/2.0 | 1834 |
| 117 | 29 | A/0:1 | 1.5/1.7 | 1803** |
| 118 | 28 | A/0:1 | 2/1.5 | 1765** |
| 119 | 41 | A/0:1 | 1/1.5 | 1843 |
| 120 | 38 | A/0:1 | 1.1/1.5 | 1757 |
| 121 | 41 | A/0:1 | 1.1/1.5 | 1799 |
| 122 | 24 | A/1:1 | 1.8/2.6 | 1863 |
| 123 | 55 | A/0:1 | 1.1/1.5 | 1795** |
| 124 | 17 | A/1:10 | 3/1.5 | 1781** |
| 125 | 36 | A/0:1 | 1.5/1.8 | 1841 |
| 126 | 26 | A/0:1 | 1.6/1.8 | 1818 |
| 127 | 54 | A/0:1 | 1.1/1.5 | 1810 |
| 128 | 34 | A/0:1 | 1.4/1.8 | 1831 |
| 129 | ND | A/1:1 | 1.4/1.8 | 1780 |
| 130 | 4 | A/0:1 | 1.1/1.5 | 1795** |
| 131 | 42 | A/0:1 | 1.1/1.5 | 1834** |
| 132 | 49 | A/0:1 | 1.1/1.5 | 1843 |
| 133 | 41 | A/0:1 | 1.1/1.5 | 1855 |
| 134 | 30 | A/0:1 | 1.1/1.5 | 1801** |
| 135 | ND | A/1:1 | 1.8/1.8 | 1779 |
| 136 | ND | A/1:1 | 1.8/1.8 | 1699 |
| 137 | ND | A/1:1 | 1.8/1.8 | 1760 |
| 138 | ND | A/1:1 | 1.8/1.8 | 1741 |
| 139 | 13 | A/1:10 | 2.4/1.5 | 1749** |
| 140 | 11 | A/1:10 | 2.9/1.5 | 1750* |
| 141 | ND | A/1:1 | 2.3/5.3 | 1742 |
| 142 | ND | A/1:1 | 2.5/5.4 | 1826 |
| 143 | ND | A/1:1 | 1.8/1.8 | 1861 |
| 144 | ND | A/1:1 | 1.5/1.5 | 1922 |
| 145 | ND | A/1:1 | 1.1/1.1 | 1716 |
| 146 | ND | A/1:1 | 1.35/1.8 | 1780* |
| 147 | ND | A/1:1 | 1.5/1.8 | 1769 |
| 148 | 31 | A/1:10 | 3/1.5 | 1857 |
| 149 | 18 | A/0:1 | 1.1/1.5 | 1777 |
| 150 | 22 | A/1:1 | 2/4.8 | 1803 |
| 151 | ND | A/1:1 | 1.8/1.8 | 1760 |
| 152 | ND | A/1:1 | 1.8/1.8 | 1826**** |
| 153 | 22 | A/1:10 | 2.5/1.6 | 1782 |
| 154 | ND | A/1:1 | 1.8/1.8 | 1780 |
| 155 | 13 | A/0:1 | 1.6/1.6 | 1768 |
| 156 | 41 | A/1:9 | 1.2/1.6 | 1788 |
| 157 | 9 | A/1:1 | 2.7/5.4 | 1810 |
| 158 | ND | A/1:1 | 1.8/4.1 | 1854 |
| 159 | 13 | A/1:9 | 1/1.6 | 1807 |
| 160 | 13 | A/1:9 | 0.95/1.6 | 1774 |
| 161 | ND | A/1:1 | 1.8/1.8 | 1690 |
| 162 | ND | A/1:1 | 3.1/6.9 | 1804 |
| 163 | ND | A/1:1 | 1.9/5.3 | 1854 |
| 164 | ND | A/1:1 | 1.8/1.8 | 1772 |
| 165 | 21 | A/1:1 | 2.0/4.9 | 1810 |
| 166 | 20 | A/1:1 | 2.0/6.2 | 1870 |
| 167 | 23 | A/1:1 | 1.8/4.1 | 1914 |
| 168 | ND | A/1:1 | 1.8/1.8 | 1737 |
| 169 | 15 | A/1:1 | 1.8/4.1 | 1700 |
| 170 | 39 | A/0:1 | 1.2/1.1 | 1728 |
| 171 | 32 | A/0:1 | 1.2/1.5 | 1729** |
| 172 | 11 | A/1:1 | 2.2/4.8 | 1755** |
| 173 | 51 | A/1:9 | 1.3/1.7 | 1909 |
| 174 | 35 | A/1:9 | 1.5/1.6 | 1816 |
| 175 | 22 | B/1:1 | 1.9/6.2 | 1742 |
| 176 | 21 | B/1:1 | 1.8/6.1 | 1782 |
| 177 | ND | A/1:1 | 3.6/1.8 | 1774 |
| 178 | 33 | A/1:9 | 1.4/1.7 | 1788** |
| 179 | 22 | B/1:1 | 1.8/3.8 | 1748 |
| 180 | 16 | A/1:1 | 1.1/1.3 | 1591*** |
| 181 | 14 | A/1:1 | 1.1/1.3 | 1617 |
| 182 | 17 | A/0:1 | 1.6/6.3 | 1725 |
| 183 | 17 | A/0:1 | 1.6/6.3 | 1691** |
| 184 | 8 | A/0:1 | 1.6/6.26 | 1707** |
| 185 | 21 | A/1:1 | 1.1/3.0 | 1725** |
| 186 | 8 | A/1:1 | 1.1/3.0 | 1630** |
| 187 | 16 | A/1:1 | 1.6/3.0 | 2110** |
| 188 | 6 | A/1:1 | 1.5/5.0 | 2976** |
| 189 | 20 | A/1:10 | 1/1.2 | 1747** |
| 190 | 9 | A/1:10 | 1.5/1.5 | 1716 |
| 191 | 18 | B/1:1 | 1.8/4.1 | 1771** |
| 192 | 11 | A/0:1 | ND/1.8 | 1738 |
| 193 | 24 | A/1:10 | 2.0/1.5 | 1820** |
| 194 | 27 | A/1:10 | 2.0/1.5 | 1821 |
| 195 | 18 | B/1:1 | 1.6/3.6 | 1798 |
| 196 | 18 | B/1:1 | 1.8/3.9 | 1754 |
| 197 | 35 | B/1:1 | 1.5/3.5 | 1810 |
| 198 | 14 | B/1:1 | 1.5/3.7 | 1784 |
| 199 | ND | B/1:1 | 1.5/2.8 | 1772 |
| 200 | 11 | B/1:1 | 1.5/3.7 | 1828 |
| 201 | 14 | B/1:1 | 1.8/6.3 | 1873** |
| 202 | 7 | B/1:1 | 1.3/5.9 | 1889** |
| 203 | 15 | A/0:1 | 1.1/1.1 | 1843 |
| 204 | 16 | B/1:1 | 2.0/5.6 | 1746 |
| 205 | 23 | B/1:1 | 1.8/3.7 | 1732 |
| 206 | 11 | A/0:1 | 1.1/1.1 | 1777 |
| 207 | 11 | B/1:1 | 1.6/4.2 | 1813** |
| 208 | 26 | B/1:1 | 1.9/3.9 | 1703 |
| 209 | 20 | A/1:1 | 1.0/1.6 | 1774 |
| 210 | 25 | A/0:1 | 1.0/1.0 | 1788 |
| 211 | 26 | A/0:1 | 1.3/1.8 | 1777 |
| 212 | 48 | A/1:1 | 1.1/3.1 | 1849** |
| 213 | 56 | A/1:1 | 1.0/3.6 | 1849** |
| 214 | 9 | B/1:1 | 1.9/1.9 | 1732 |
| 215 | 35 | A/0:1 | 1.3/1.8 | 1820*** |
| 216 | 31 | A/0:1 | 1.3/1.8 | 1828*** |
| 217 | 12 | B/1:1 | 2.0/2.1 | 1676 |
| 218 | 24 | A/1:10 | 1.2/1.5 | 1766*** |
| 219 | 24 | A/1:1 | 1.4/3.5 | 1860 |
| 220 | 21 | A/0:1 | 1.3/1.8 | 1785 |
| 221 | 42 | A/0:1 | 1.3/1.8 | 1787 |
| 222 | 20 | A/0:1 | 1.1/1.1 | 1787 |
| 223 | 32 | A/1:1 | 2.4/4.5 | 1817** |
| 224 | 36 | A/1:1 | 1.6/5.6 | 1773** |
| 225 | ND | A/0:1 | 1.1/1.1 | 1787 |
| 226 | 28 | A/1:1 | 1.5/3.0 | 1766* |
| 227 | 22 | A/1:1 | 1.2/3.7 | 1777** |
| 228 | 21 | A/0:1 | 1/1.1 | 1848** |
| 229 | 16 | A/0:1 | 1/1.2 | 1793 |
| 230 | 27 | A/0:1 | 1.3/1.8 | 1838*** |
| 231 | 36 | A/0:1 | 1.3/1.8 | 1785* |
| 232 | 32 | A/1:1 | 1.8/4.6 | 1806 |
| 233 | 5 | A/1:1 | 1.1/7.3 | 1878 |
| 234 | 7 | B/1:1 | 1.5/3.5 | 1836* |
| 235 | 15 | B/1:1 | 1.4/4.8 | 1750 |
| 236 | 4 | B/1:1 | 1.4/6.3 | 1819** |
| 237 | 14 | A/0:1 | 1.1/1.1 | 1787 |
| 238 | 25 | B/0:1 | 1.1/1.1 | 1771 |
| 239 | 22 | B/1:1 | 1.6/1.5 | 1810 |
| 240 | 4.7 | A/1:60 | 1.2/1.1 | 1810*** |
| 241 | 24 | B/1:1 | 1.1/2.5 | 1779** |
| 242 | N.D. | A/1:50 | 1.1/1.2 | 1787 |
| 243 | 20 | A/0:1 | 1.1/1.1 | 1790 |
| 244 | 24 | C/0:1 | 1.1/1.1 | 1808 |
| 245 | 5 | C/0:1 | 1.8/1.8 | 1864 |
| 246 | 3 | B/1:1 | 1.8/6.1 | 1969.7 |
| 247 | 41 | A/0:1 | 1.8/6.1 | 1957 |

TABLE 7-continued

| Compound No. | Yield (%) | Method/ DMF: MeOH | Reagent Equivalents (aldehyde/ NaBH3CN) | FAB-MS (M + 3H) |
|---|---|---|---|---|
| 248 | ND | E/0:1 | 3.0/3.0 | 1925** |
| 249 | ND | E/0:2 | 3.0/3.0 | 2091** |
| 250 | ND | D/0:3 | 2.0/3.0 | 1759** |
| 251 | ND | E/0:4 | 3.0/3.0 | 1925** |
| 252 | ND | D/0:5 | 2.0/3.0 | 1793** |
| 253 | ND | E/0:6 | 3.0/3.0 | 1991** |
| 254 | ND | E/0:7 | 3.0/3.0 | 1994***** |
| 255 | ND | E/0:8 | 3.0/3.0 | 2194***** |
| 256 | 2 | A/1:1 | 1.0/1.8 | 1805.5 |
| 257 | 2 | A/1:1 | 1.0/1.8 | 1699.4 |
| 258 | 2 | A/1:1 | 1.0/1.8 | 1878.7 |
| 259 | 2 | A/1:9 | 1.0/1.8 | 1734.6** |
| 260 | 16 | A/0:1 | 1.4/1.7 | 1983** |
| 261 | 4 | A/1:9 | 1.6/1.6 | 1943***** |
| 262 | 11 | A/0:1 | 1.2/1.6 | 1982*** |
| 263 | 15 | A/0:1 | 1.5/1.5 | 2015** |
| 264 | 11 | A/0:1 | 1.5/1.5 | 1974 |
| 265 | 18 | A/0:1 | 1.5/1.5 | 1862 |
| 266 | 22 | A/0:1 | 1.5/1.5 | 2047*** |
| 267 | 6 | A/0:1 | 1.5/1.5 | 2048 |
| 268 | 7 | A/0:1 | 1.5/1.5 | 2046 |
| 269 | 18 | A/0:1 | 1.5/1.5 | 1860* |
| 270 | 19 | A/1:10 | 2/1.5 | 1954 |
| 271 | 14 | A/0:1 | 1.5/1.5 | 1958 |
| 272 | 7 | A/0:1 | 1.5/1.5 | 1909** |
| 273 | 15 | A/0:1 | 1.5/1.5 | 1954 |
| 274 | 18 | A/0:1 | 1.7/2.5 | 1775** |
| 275 | 24 | A/0:1 | 1.6/1.6 | 1875** |
| 276 | 50 | A/0:1 | 1.8/6.1 | 1885** |
| 277 | 6 | A/0:1 | 1.1/1.5 | 2088 |
| 278 | 20 | A/0:1 | 1.5/1.5 | 1865** |
| 279 | 4 | A/0:1 | 1.5/1.6 | 1949** |
| 280 | 19 | A/0:1 | 1.7/2.5 | 1775** |
| 281 | 41 | A/0:1 | 1.7/2.5 | 1775** |
| 282 | 22 | A/0:1 | 1.8/6.1 | 1932* |
| 283 | 5 | A/0:1 | 1.8/6.1 | 2002 |
| 284 | 9 | A/0:1 | 1.8/6.1 | 1973** |
| 285 | 15 | A/0:1 | 1.6/1.6 | 1875** |
| 286 | 14 | A/0:1 | 1.8/1.6 | 1962* |
| 287 | 21 | A/0:1 | 1.5/1.5 | 1781** |
| 288 | ND | C | 1.8/1.8 | 2006 |

N.D. = not determined
*M + H
**M + 2H
***M + 4H
****M + 6H
*****M + 5H

EXAMPLE 7

Capsule Formulation

Capsules containing 250 mg of Compound 2 are prepared using the following ingredients:

| Ingredient | Weight |
|---|---|
| Compound 2 HCl salt | 255.4 mg |
| Corn starch flowable powder | 150 mg |
| Corn starch | 144.6 mg |

Compound 2 (HCl salt form, 255.4 mg), corn starch flowable powder (150 mg) and corn starch (144.6 mg) are blended in a suitable mixer until homogenous. The mixture is used to fill a hard gelatin capsule to a net fill weight of 550 mg.

EXAMPLE 8

Capsule Formulation

Capsules containing 250 mg of Compound 229 are prepared using the following ingredients:

| Ingredient | Weight |
|---|---|
| Compound 229 HCl salt | 255.4 mg |
| Corn starch flowable powder | 150 mg |
| Corn starch | 144.6 mg |

Compound 2 (HCl salt form, 255.4 mg), corn starch flowable powder (150 mg) and corn starch (144.6 mg) are blended in a suitable mixer until homogenous. The mixture is used to fill a hard gelatin capsule to a net fill weight of 550 mg.

EXAMPLE 9

Suspension Formulation

A sterile insoluble form of compound 2 is milled or screened to a particle size suitable for suspension. This particulate material is suspended in the following vehicle:

| Ingredient | Weight |
|---|---|
| Lecithin | 1% |
| Sodium citrate | 2% |
| Propylparaben | 0.015% |
| Distilled water | q.s. to desired volume |

EXAMPLE 10

Suspension Formulation

A sterile insoluble form of compound 229 is milled or screened to a particle size suitable for suspension. This particulate material is suspended in the following vehicle:

| Ingredient | Weight |
|---|---|
| Lecithin | 1% |
| Sodium citrate | 2% |
| Propylparaben | 0.015% |
| Distilled water | q.s. to desired volume |

EXAMPLE 11

Tablet Formulation

Tablets containing 250 mg of compound 2 are prepared with the following composition:

| Ingredient | Weight |
|---|---|
| Lecithin | 1% |
| Sodium citrate | 2% |
| Propylparaben | 0.015% |
| Distilled water | q.s. to desired volume |

EXAMPLE 12

Tablet Formulation

Tablets containing 250 mg of compound 229 are prepared with the following composition:

| Ingredient | Weight |
| --- | --- |
| Lecithin | 1% |
| Sodium citrate | 2% |
| Propylparaben | 0.015% |
| Distilled water | q.s. to desired volume |

EXAMPLE 13

Tablet Formulation

Tablets containing 250 mg of compound 2 are prepared with the following composition:

| Ingredient | Weight |
| --- | --- |
| Compound 2 HCl salt | 255.4 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 ml |

EXAMPLE 14

Tablet Formulation

Tablets containing 250 mg of compound 229 are prepared with the following composition:

| Ingredient | Weight |
| --- | --- |
| Compound 229 HCl salt | 255.4 mg |
| Microcrystalline cellulose | 101.1 mg |
| Croscarmellose sodium | 12.0 mg |
| Providone | 12.0 mg |
| Magnesium stearate | 3.0 mg |
| Stearic acid | 4.0 mg |
| Purified water | 0.16 ml |

We claim:

1. A compound of the formula:

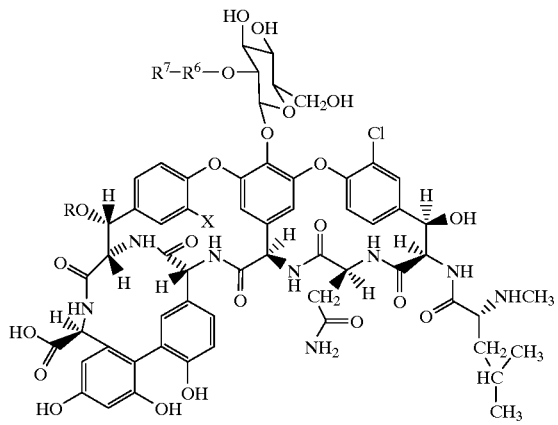

wherein X is hydrogen or chloro; R and $R^6$ are 4-epi-vancosaminyul; $R^7$ is $(C_1-C_{12}$ alkyl)-$R^8$ and is attached to the amino group of $R^6$; and $R^8$ is a group of the formula

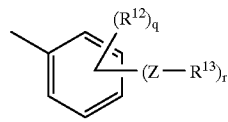

wherein q is 0 to 4;

$R^{12}$ is independently selected from the group consisting of:
(i) halo,
(ii) nitro,
(iii) $(C_1-C_6)$alkyl,
(iv) $(C_1-C_6)$alkoxy,
(v) halo-$(C_1-C_6)$alkyl,
(vi) halo-$(C_1-C_6)$alkoxy,
(vii) hydroxy, and
(vii) $(C_1-C_6)$thioalkyl;

r is 1 to 5; provided that the sum of q and r is no greater than 5;

Z is selected from the group consisting of:
(i) a single bond,
(ii) divalent $(C_1-C_6)$alkyl unsubstituted or substituted with hydroxy, $(C_1-C_6)$alkyl, or $(C_1-C_6)$alkoxy,
(iii) divalent $(C_2-C_6)$alkenyl,
(iv) divalent $(C_2-C_6)$alkynyl, or
(v) a group of the formula —$(C(R^{14})_2)_s$—$R^{15}$— or —$R^{15}$—$(C(R^{14})_2)_s$—, wherein s is 0–6; wherein each $R^{14}$ substituent is independently selected from hydrogen, $(C_1-C_6)$-alkyl, or $(C_4-C_{10})$ cycloalkyl; and $R^{15}$ is selected from —O—, —S—, —SO—, —$SO_2$—, —$SO_2O$—, —C(O)—, —OC(O)—, —C(O)O—, —NH—, —N($C_1-C_6$ alkyl)-, —C(O)NH—, —NHC(O)—, and N=N;

$R^{13}$ is independently selected from the group consisting of:
(i) $(C_4-C_{10})$heterocyclyl,
(ii) heteroaryl,
(iii) $(C_4-C_{10})$cycloalkyl unsubstituted or substituted with $(C_1-C_6)$alkyl, and
(iv) phenyl unsubstituted or substituted with 1 to 5 substituents independently selected from: halo, hydroxy, nitro, $(C_1-C_{10})$ alkyl, $(C_1-C_{10})$alkoxy, halo-$(C_1-C_3)$alkoxy, halo-$(C_1-C_3)$alkyl, $(C_1-C_3)$ alkoxyphenyl, phenyl, phenyl-$(C_1-C_3)$alkyl, $(C_1-C_6)$alkoxyphenyl, phenyl-$(C_2-C_3)$alkynyl, and $(C_1-C_6)$alkylphenyl; or a salt thereof.

2. A compound of claim 1 wherein $R^7$=—$CH_2$—$R^8$.

3. A compound of claim 2 wherein $R^{13}$=heteroaryl.

4. The compound of claim 3 which is 4-(2-thienyl)benzyl A82846B or a salt thereof.

5. A compound of claim 2 wherein $R^{13}$=phenyl or substituted phenyl as defined.

6. A compound of claim 2 selected from the group consisting of:
chlorophenylbenzyl-A82846B,
phenylbenzyl-A82846B,
benzylbenzyl-A82846B,
methylphenylbenzyl-A82846B,
pentylphenylbenzyl-A82846B,
methoxyphenylbenzyl-A82846B,
pentoxyphenylbenzyl-A82846B,
nitrophenoxybenzyl-A82846B,
fluorophenylbenzyl-A82846B,
phenyl-ethynylbenzyl-A82846B,
phenoxybenzyl-A82846B, benzyloxybenzyl-A82846B,
nitrophenylbenzyl-A82846B,
chlorophenoxybenzyl-A82846B,
chlorobenzyloxybenzyl-A82846B,
butylphenoxybenzyl-A82846B,
trifluoromethylphenoxybenzyl-A82846B,
dichlorophenoxybenzyl-A82846B,
nitrobenzyloxybenzyl-A82846B,
benzoyloxybenzyl-A82846B,
cyclohexyloxybenzyl-A82846B,
cyclohexanoyloxybenzyl-A82846B,
thiophenylbenzyl-A82846B,
chlorophenylsulfonylbenzyl-A82846B,
cyclohexylbenzyl-A82846B,
trifluoromethylphenylbenzyl-A82846B,
butylphenylthiobenzyl-A82846B, and
bromophenylbenzyl-A82846B,
or a salt thereof.

7. The compound of claim 1 which is 4-phenylbenzyl A82846B or a salt thereof.

8. A pharmaceutical composition comprising a compound of claim 1, associated with one or more pharmaceutically acceptable carriers therefor.

9. A pharmaceutical composition comprising a compound of claim 2, associated with one or more pharmaceutically acceptable carriers therefor.

10. A pharmaceutical composition comprising a compound of claim 3, associated with one or more pharmaceutically acceptable carriers therefor.

11. A pharmaceutical composition comprising a compound of claim 4, associated with one or more pharmaceutically acceptable carriers therefor.

12. A pharmaceutical composition comprising a compound of claim 5, associated with one or more pharmaceutically acceptable carriers therefor.

13. A pharmaceutical composition comprising a compound of claim 6, associated with one or more pharmaceutically acceptable carriers therefor.

14. A pharmaceutical composition comprising a compound of claim 7, associated with one or more pharmaceutically acceptable carriers therefor.

15. A method of treating a susceptible bacterial infection which comprises administering an antibacterially effective amount of a composition of claim 8, to a host in need of such treatment.

16. A method of treating a susceptible bacterial infection which comprises administering an antibacterially effective amount of a composition of claim 9, to a host in need of such treatment.

17. A method of treating a susceptible bacterial infection which comprises administering an antibacterially effective amount of a composition of claim 10, to a host in need of such treatment.

18. A method of treating a susceptible bacterial infection which comprises administering an antibacterially effective amount of a composition of claim 11, to a host in need of such treatment.

19. A method of treating a susceptible bacterial infection which comprises administering an antibacterially effective amount of a composition of claim 12, to a host in need of such treatment.

20. A method of treating a susceptible bacterial infection which comprises administering an antibacterially effective amount of a composition of claim 13, to a host in need of such treatment.

21. A method of treating a susceptible bacterial infection which comprises administering an antibacterially effective amount of a composition of claim 14, to a host in need of such treatment.

22. A method of claim 15 wherein the bacterial infection comprises vancomycin-resistant enterococci.

23. The method of claim 16 wherein the bacterial infection comprises vancomycin-resistant enterococci.

24. The method of claim 17 wherein the bacterial infection comprises vancomycin-resistant enterococci.

25. The method of claim 18 wherein the bacterial infection comprises vancomycin-resistant enterococci.

26. The method of claim 19 wherein the bacterial infection comprises vancomycin-resistant enterococci.

27. The method of claim 20 wherein the bacterial infection comprises vancomycin-resistant enterococci.

28. The method of claim 21 wherein the bacterial infection comprises vancomycin resistant enterococci.

29. A process for the preparation of a compound of claim 1 which comprises:

(a) reacting a compound of the formula

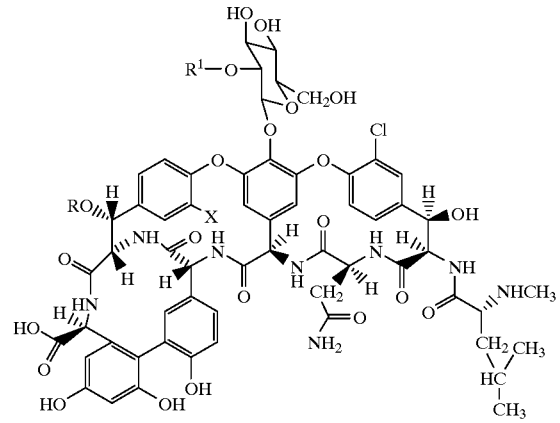

wherein X is hydrogen or chloro, and R and $R^1$ are 4-epi-vancosaminyl, with an aldehyde corresponding to the group $R^7$ as defined in claim 1, in methanol at about 25° C. to about 100° C.;

(b) continuing the reaction until formation of a Schiff's base; and (c) reducing the Schiff's base by addition of a metal borohydride to the mixture at about 25° C. to about 100° C.

30. The process of claim 29, wherein the aldehyde is p-phenoxybenzaldehyde.

31. The process of claim 29 wherein the aldehyde is p-phenylbenzaldehyde.

32. A process for the preparation of a compound of claim 1 which comprises reacting in a polar solvent at about 25° C. to about 100° C.:

i) a glycopeptide antibiotic of the formula:

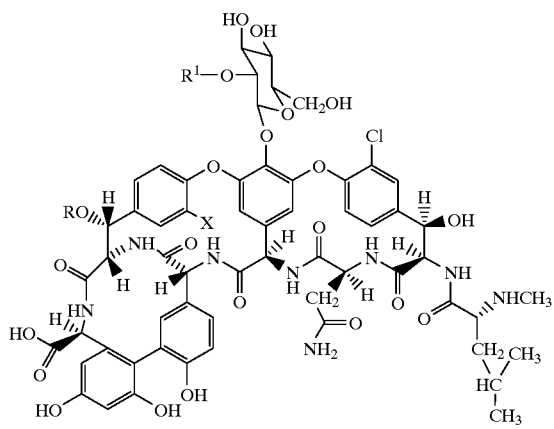

wherein X is hydrogen or chloro and R and $R^1$ are 4-epi-vancosaminyl, with ii) an aldehyde corresponding to the group $R^7$ as defined in claim 1, in the presence of iii) a reducing agent selected from a metal borohydride, and a homogeneous or heterogeneous catalytic hydrogenation agent or agents;

for a time sufficient to produce a compound of claim 1.

33. The process of claim 32 wherein the reaction is carried out for about 20 to 28 hours at a temperature of about 60° C. to about 70° C., and the reducing agent is sodium cyanoborohydride.

34. The process of claim 32 wherein the glycopeptide antibiotic is A82846B.

* * * * *